(12) United States Patent
Singh et al.

(10) Patent No.: US 7,985,755 B2
(45) Date of Patent: *Jul. 26, 2011

(54) 2,4-DIAMINOQUINAZOLINES FOR SPINAL MUSCULAR ATROPHY

(75) Inventors: Jasbir Singh, Naperville, IL (US); Mark E. Gurney, Grand Rapids, MI (US)

(73) Assignee: Families of Spinal Muscular Atrophy, Libertyville, IL (US)

( * ) Notice: Subject to any disclaimer, the term of this patent is extended or adjusted under 35 U.S.C. 154(b) by 69 days.

This patent is subject to a terminal disclaimer.

(21) Appl. No.: 11/832,255

(22) Filed: Aug. 1, 2007

(65) Prior Publication Data

US 2009/0042900 A1 Feb. 12, 2009

Related U.S. Application Data

(60) Provisional application No. 60/821,088, filed on Aug. 1, 2006, provisional application No. 60/882,355, filed on Dec. 28, 2006.

(51) Int. Cl.
*A61K 31/517* (2006.01)

(52) U.S. Cl. ............... 514/266.4; 544/291; 544/359; 546/199; 546/268.1; 548/240; 548/335.1; 548/560; 549/59; 549/356; 549/398; 549/505

(58) Field of Classification Search ............... 514/266.4; 544/291, 359; 546/199, 268.1; 548/240, 548/335.1, 560; 549/59, 356, 398, 505
See application file for complete search history.

(56) References Cited

U.S. PATENT DOCUMENTS

| | | | |
|---|---|---|---|
| 5,064,833 | A | 11/1991 | Ife |
| 5,534,518 | A | 7/1996 | Henrie |
| 5,616,718 | A | 4/1997 | Henrie, II |
| 5,760,230 | A | 6/1998 | Schohe-Loop |
| 5,874,438 | A | 2/1999 | Schohe-Loop |
| 5,874,579 | A | 2/1999 | Henrie, II et al. |
| 6,096,499 | A | 8/2000 | Kozlowski et al. |
| 6,204,267 | B1 | 3/2001 | Tang et al. |
| 6,248,771 | B1 | 6/2001 | Shenoy et al. |
| 6,492,389 | B1 | 12/2002 | Huang et al. |
| 6,635,651 | B2 | 10/2003 | Uckun |
| 6,911,446 | B2 | 6/2005 | Tang |
| 2005/0065173 | A1 | 3/2005 | Jarecki |

FOREIGN PATENT DOCUMENTS

| | | | |
|---|---|---|---|
| WO | WO9418980 | | 9/1994 |
| WO | WO9838984 | | 9/1998 |
| WO | WO9850370 | | 11/1998 |
| WO | WO0059884 | | 10/2000 |
| WO | WO03097615 | | 11/2003 |
| WO | WO2004002961 | | 1/2004 |
| WO | WO2004069255 | | 8/2004 |
| WO | WO2004113305 | | 12/2004 |
| WO | 2005123724 | | 12/2005 |
| WO | WO 2005/123724 | * | 12/2005 |

OTHER PUBLICATIONS

Cartegni L and Krainer AR, Disruption of an SF2/ASF-dependent exonic splicing enhancer in SMN2 causes spinal muscular atrophy in the absence of SMN1, Nature Genetics, 2002, pp. 377-384, vol. 30, No. 4.

Brichta L et al, Valproic acid increases the SMN2 protein level: a well-known drug as a potential therapy for spinal muscular atrophy, Human Molecular Genetics, 2003, pp. 2481-2489, vol. 12, No. 9.

Sumner CJ et al., Valproic acid increases SMN levels in spinal muscular atrophy patient cells, Annals of Neurology, 2003, pp. 647-654, vol. 54, No. 5.

Chang JG et al., Treatment of spinal muscular atrophy by sodium butyrate, PNAS, 2001, pp. 9808-9813, vol. 98, No. 17.

Andreassi C et al., Phenylbutyrate increases SMN expression in vitro: relevance for treatment of spinal muscular atrophy, Eur J Human Genetics, 2004, pp. 59-65, vol. 12.

Remenar JF et al., Crystal engineering of novel cocrystals of a triazole drug with 1,4-dicarboxylic acids, J Am Chem Soc, 2003, pp. 8456-8457, vol. 125.

Amrollahibiyouki MA et al., Hydroxymethylation and carbamoylation of di-and tetramethylpyridines using radical substitution (minisci) reactions, Synthetic Communications, 1998, pp. 3817-3825, vol. 28, No. 20.

Zlokarnik G et al., Quantitation of transcription and clonal selection of single living cells with B-lactamase as reporter, Science, 1998, pp. 84-88, vol. 279.

Appleman JR et al., Role of aspartate 27 in the binding of methotrexate to dihydrofolate reductase from *Escherichia coli*, J Biol Chem, 1988, pp. 9187-9198, vol. 263, No. 19.

Nelson RG and Rosowsky A, Dicyclic and tricyclic diaminopyrimidine derivatives as potent inhibitors of cryptosporidium parvum dihydrofolate reductase: structure-activity and structure-selectivity correlations, Antimicrobial Agents and Chemotherapy, 2001, pp. 3293-3303, vol. 45, No. 12.

(Continued)

*Primary Examiner* — James O Wilson
*Assistant Examiner* — Douglas M Willis
(74) *Attorney, Agent, or Firm* — Fish & Richardson P.C.

(57) ABSTRACT

2,4-Diaminoquinazolines of formula (I)

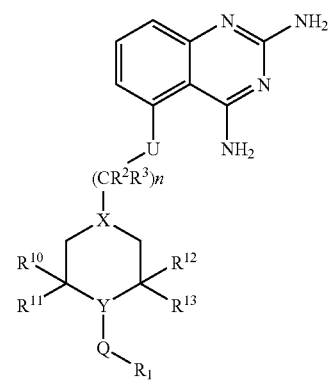

are provided herein and are useful for treating spinal muscular atrophy (SMA).

53 Claims, No Drawings

OTHER PUBLICATIONS

Pitman MC et al., Flashflood: A 3D field-based similarity search and alignment method for flexible molecules, J Computer-Aided Molecular Design, 2001, pp. 587-612, vol. 15.

Rosowsky A et al., 2,4-diamino-5-substituted-quinazolineass inhibitors of a human dihydrofolate reductase with a site-directed mutation at position 22 and of the dihydrofolate reductases from pneumocystis carinii and toxoplasma gondii, J Med Chem, 1995, pp. 745-752, vol. 38.

Harris NV et al., Antifolate and antibacterial activities of 5-substituted 2,4-diaminoquinazolines, J Med Chem, 1990, pp. 434-444, vol. 33, No. 1.

Ghose AK and Crippen GM, General distance geometry three-dimensional receptor model for diverse dihydrofolate reductase inhibitors, J Med Chem, 1998, pp. 901-914, vol. 27.

Gohda K et al., Identification of Novel Potent Inhibitors for ATP-Phosphoribosyl Transferase Using Three-Dimensional Structural Database Search Technique, Quantitative Structure-Activity Relationships, 2001, pp. 143-147, vol. 20, No. 2.

Zolli-Juran M et al., High throughput screening identifies novel inhibitors of *Escherichia coli* dihydrofolate reductase that are competitive with dihydrofolate, Bioorganic & Medicinal Chemistry Letters, 2003, pp. 2493-2496, vol. 13, No. 15.

Jagdmann EG et al., Synthesis of 5-(4-substituted benzyl)-2,4-diaminoquinazolines as inhibitors of *Candida albicans* dihydrofolate reductase, Journal of Heterocyclic Chemistry, 1995, pp. 1461-1465, vol. 32, No. 5.

International Search Report dated Oct. 29, 2007 in connection with International Patent Application No. PCT/US2007/074971.

International Search Report dated Jun. 6, 2005 in connection with International Patent Application No. PCT/US2005/019753.

Restriction Requirement in U.S. Appl. No. 11/147,127, pp. 1-7, dated Mar. 11, 2008.

Fish and Richardson P.C., Response to Restriction Requirement in U.S. Appl. No. 11/147,127, pp. 1-4, filed Sep. 11, 2008.

Non-Final Office Action in U.S. Appl. No. 11/147,127, pp. 1-9, dated Nov. 25, 2008.

Fish and Richardson P.C., Amendment and Reply under 37 C.F.R. § 1.111 in U.S. Appl. No. 11/147,127, pp. 1-27, filed May 26, 2009.

Final Office Action in U.S. Appl. No. 11/147,127, pp. 1-8, dated Sep. 3, 2009.

Fish and Richardson P.C., Petition under 37 C.F.R. § 1.181—Premature Final Rejection in U.S. Appl. No. 11/147,127, pp. 1-4, filed Nov. 3, 2009.

Fish and Richardson P.C., Amendment and Reply to the Final Office Action Dated Sep. 3, 2009 in U.S. Appl. No. 11/147,127, pp. 1-23, filed Jan. 4, 2010.

Technology Center Director Remy Yucel, Petition Decision in U.S. Appl. No. 11/147,127, pp. 1-3, dated Jan. 8, 2010.

Interview Summary in U.S. Appl. No. 11/147,127, 4 pages, dated Jan. 14, 2010.

\* cited by examiner

2,4-DIAMINOQUINAZOLINES FOR SPINAL MUSCULAR ATROPHY

RELATED APPLICATIONS

This application claims priority to U.S. Provisional Application No. 60/821,088 filed Aug. 1, 2006 and U.S. Provisional Application No. 60/882,355 filed Dec. 28, 2006, each of which is incorporated herein by reference in its entirety.

FIELD OF THE INVENTION

The invention relates to a genus of 2,4-diaminoquinazolines that are useful for treating spinal muscular atrophy (SMA).

BACKGROUND

Spinal muscular atrophy (SMA) is a currently untreatable, autosomal recessive genetic disease caused by a deficiency of full-length survival motor neuron (SMN) protein. The symptoms are the result of progressive degeneration of motor neurons in the anterior horn of the spinal cord resulting in weakness and wasting of the voluntary muscles.

Type I (Acute) SMA is also called Werdnig-Hoffmann Disease. SMA type I is evident before birth or within the first few months of life. There may be a reduction in fetal movement in the final months of pregnancy. There is a general weakness in the intercostals and accessory respiratory muscles. The chest may appear concave. Symptoms include floppiness of the limbs and trunk, feeble movements of the arms and legs, swallowing and feeding difficulties, and impaired breathing. Affected children never sit or stand and usually die before the age of 2.

Type II (Chronic) SMA is usually diagnosed by 15 months. Children may have respiratory problems, floppy limbs, decreased or absent deep tendon reflexes, and twitching of arm, leg, or tongue muscles. These children may learn to sit but cannot stand or walk. Life expectancy varies. Feeding and swallowing problems are not usually characteristic of Type II, although in some patients a feeding tube may become necessary. Tongue fasciculations are less often found in children with Type II but a fine tremor in the outstretched fingers is common.

Type III (Mild) SMA, often referred to as Kugelberg-Welander or Juvenile Spinal Muscular Atrophy, is usually diagnosed between 2 and 17 years of age. Symptoms include abnormal manner of walking; difficulty running, climbing steps, or rising from a chair; and slight tremor of the fingers. The patient with Type III can stand alone and walk; tongue fasciculations are seldom seen. Types I, II and III progress over time, accompanied by deterioration of the patient's condition.

Type IV (Adult Onset) typically begins after age 35. Adult SMA is characterized by insidious onset and very slow progression. The bulbar muscles are rarely affected in Type IV. It is not clear that Type IV SMA is etiologically related to the Type I-III forms. There is a second type of Adult Onset X-Linked SMA, known as Kennedy's Syndrome or Bulbo-Spinal Muscular Atrophy. It occurs only in males, and, unlike the other forms of SMA, it is associated with a mutation in the gene that codes for part of the androgen receptor. The facial and tongue muscles are noticeably affected. The course of the Adult Onset disease is variable, but in general it tends to be slowly progressive or nonprogressive.

Type I, II and III SMA are caused by a mutation in a part of the DNA called the survival motor neuron (SMN1) gene, which normally produces a protein called SMN. Because of their gene mutation, people with SMA make less SMN protein, which results in the loss of motor neurons. SMA symptoms may be improved by increasing the levels of SMN protein. Normally the SMN1 gene provides instructions for making a protein called Survival of Motor Neuron 1. The SMN1 protein helps to assemble the cellular machinery needed to process pre-mRNA. More than 90 percent of individuals with spinal muscular atrophy lack part or all of both copies of the SMN1 gene. A small percentage of people with this condition lack one copy of the SMN1 gene and have a small type of mutation in the remaining copy. About 30 different mutations have been identified. The most frequent of these mutations replaces the amino acid tyrosine with cysteine at position 272 in the SMN1 protein. Other mutations replace amino acids at different positions or produce an abnormally short protein. As a result of these missing or altered genes, cells have a shortage of functional SMN1 protein. It remains unclear why motor neurons are particularly vulnerable to a shortage of this protein. Loss of the SMN1 protein from motor neurons results in the degeneration of these nerve cells, leading to the signs and symptoms of spinal muscular atrophy.

In some cases of spinal muscular atrophy, particularly the milder cases, the SMN1 gene is replaced by an almost identical gene called SMN2. Typically, people who do not have spinal muscular atrophy have two copies of the SMN2 gene. In some affected individuals, however, the SMN2 gene replaces the SMN1 gene, and as a result, the number of SMN2 genes increases from two to three or more (and the number of SMN1 genes decreases). On a limited basis, extra SMN2 genes can help replace the protein needed for the survival of motor neurons. In general, symptoms are less severe and begin later in life in affected individuals with three or more copies of the SMN2 gene. The SMN2 gene provides instructions for making a protein called survival of motor neuron 2. This protein is made in four different versions, but only isoform d is full size and functional and appears to be identical to the SMN1 protein. The other isoforms (a, b, and c) are smaller and may not be fully functional. It appears that only a small amount of the protein made by the SMN2 gene is isoform d. Among individuals with spinal muscular atrophy (who lack functional SMN1 genes), additional copies of the SMN2 gene can modify the course of the disorder. On a limited basis, the extra SMN2 genes can help replace the protein needed for the survival of motor neurons. Spinal muscular atrophy still occurs, however, because most of the proteins produced by SMN2 genes are isoforms a, b, and c, which are smaller than the SMN1 protein and cannot fully compensate for the loss of SMN1 genes. A recent article by Cartegni and Kramer [*Nature Genetics* 30, 377-384 (2002)] suggests that the molecular basis for the failure of the nearly identical gene SMN2 to provide full protection against SMA stems from inefficient recognition of an exonic splicing enhancer by the splicing factor SF2/ASF. Even so, the small amount of full-sized protein produced from three or more copies of the SMN2 gene can delay onset and produce less severe symptoms, as seen in spinal muscular atrophy, types II and III.

One of the first studies on pharmaceutical therapy for spinal muscular atrophy has demonstrated that, in cultured cells, valproic acid increases production of normal protein produced by the SMN2 gene. While preliminary, these studies [Britcha et al. Human Molecular Genetics, 12, 2481-2489 (2003); Sumner et al. *Annals of Neurology*, 54, 647-654 (2003)], suggest that valproic acid or related drugs may be able to halt or even reverse the course of SMA. The study used cultured cells taken from patients with SMA type I, and demonstrated a dose-related increase in gene activity, increasing production of functional SMN protein by 30 to 50 percent. Unfortunately, treatment with valproic acid can lead to liver toxicity, especially in children under 2 years of age, and safe doses of the drug may not be able to increase the amount of SMN protein enough to reduce symptoms of the disease. However, valproic acid belongs to a class of drugs known as histone deacetylase (HDAC) inhibitors, and persons of skill in the art believe that other HDAC inhibitors may be useful for treating SMA. For example, two other HDAC inhibitor, sodium butyrate and phenylbutyrate have also been shown to increase SMN expression [Chang et al. PNAS, 98, 9808-9813 (2001); Andreassi et al. European Journal of Human Genetics, 12, 59-65. The National Institute of Neurological Disorders and Stroke (NINDS) is currently undertaking studies to support this hypothesis.

It would be useful to have compounds that promote SMN2 without the adverse side effects of valproic acid. It would be further useful to have compounds that increase the total SMN1 protein or that alter the splicing to provide increase in full length to Δ7 SMN transcripts ratio in favor of full length protein or that do both.

SUMMARY OF THE INVENTION

It has now been found that certain 2,4-diaminoquinazolines are useful for treating SMA.

In one aspect, the invention relates to novel 2,4-diaminoquinazoline compounds having formula I:

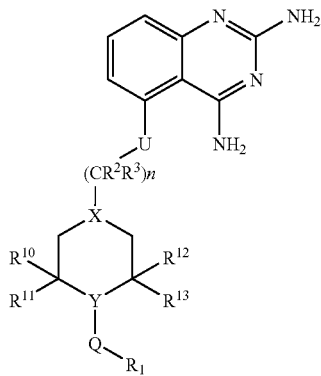

I wherein
U is chosen from O and a bond;
$R^2$ and $R^3$ are independently chosen in each occurrence from H and lower alkyl;
n=0, 1, 2, or 3;
X is chosen from N and CH;
Y is chosen from N, CH, C(OH) and N→O;
$R^{10}$, $R^{11}$, $R^{12}$ and $R^{13}$ are independently selected from H and lower alkyl or, taken together, $R^{10}$ and $R^{11}$ or $R^{12}$ and $R^{13}$ are =O;
Q is chosen from —$CH_2$—, —C(=O)—, —$CH_2$C(=O)—, —$SO_2$—, —$CR^{14}R^{15}$—, —C(=O)$CH_2$S— and a direct bond, wherein $R^{14}$ and $R^{15}$ are independently selected from hydrogen and lower alkyl; and
$R^1$ is selected from the group consisting of H, alkyl, alkoxy, carbocycle, heterocyclyl, fluoroalkyl, alkoxyalkyl, substituted carbocycle and substituted heterocyclyl.

In an embodiment, X is CH and Y is N when U is oxygen or a bond, forming a piperidine or piperidinone; in certain embodiments, $R^{10}$, $R^{11}$, $R^{12}$ and $R^{13}$ are H, forming a piperidine, and $R^2$ and $R^3$ are H and n is 1; in other embodiments, $R^{10}$ and $R^{11}$ are =O and $R^{12}$ and $R^{13}$ are hydrogen, forming a piperidinone; in another embodiment, $R^{10}$ and $R^{11}$ are =O and $R^{12}$ and $R^{13}$ are =O, forming a glutarimide.

In certain embodiments, when U is O, $R^2$ and $R^3$ are H, n=1 or 2, and X and Y are both CH, forming a cyclohexane; in some embodiments, $R^{10}$, $R^{11}$, $R^{12}$ and $R^{13}$ are H, Q is $CH_2$ or a bond, and $R^1$ is carbocycle, substituted carbocycle or fluoroalkyl; in certain embodiments, the substituted carbocycle is monosubstituted or disubstituted phenyl, and the compound can be chosen from:
5-[4-(2-Chlorobenzyl)cyclohexylmethoxy]quinazoline-2,4-diamine;
5-[4-(3-Chlorobenzyl)cyclohexylmethoxy]quinazoline-2,4-diamine;
5-[4-(2-Fluorobenzyl)cyclohexylmethoxy]quinazoline-2,4-diamine; and
5-[4-(4-Chlorophenyl)cyclohexylmethoxy]quinazoline-2,4-diamine.

In another embodiment, when U is —O— and $R^2$ and $R^3$ are H, $R^{10}$, $R^{11}$, $R^{12}$ and $R^{13}$ are H, n is 1, then Q is a direct bond or $CH_2$ and $R^1$ is carbocycle, substituted carbocycle or fluoroalkyl, with the proviso that the compound is not 5-[1-(3,4-dichlorobenzyl)-piperidin-4-ylmethoxy]-quinazoline-2,4-diamine.

In still other embodiments, when U is oxygen or a bond, X and Y are N, $R^{10}$, $R^{11}$, $R^{12}$ and $R^{13}$ are H; in certain embodiments, U is a bond and n is zero, Q is $CH_2$, C(=O), $SO_2$ or direct bond, and $R^1$ is carbocycle or substituted carbocycle, and the compound is chosen from:
5-(4-Benzyl-piperazin-1-yl)-quinazoline-2,4-diamine;
5-(4-Naphthalen-1-ylmethyl-piperazin-1-yl)-quinazoline-2,4-diamine;
[4-(2,4-Diamino-quinazolin-5-yl)-piperazin-1-yl]-naphthalen-1-yl-methanone; and
5-[4-(Naphthalene-2-sulfonyl)-piperazin-1-yl]-quinazoline-2,4-diamine;
in some embodiments the substituted carbocycle is monosubstituted or disubstituted phenyl, and the compound is chosen from:
5-[4-(2-Methyl-benzyl)-piperazin-1-yl]-quinazoline-2,4-diamine;
5-[4-(2,4-Dichloro-benzyl)-piperazin-1-yl]-quinazoline-2,4-diamine;
[4-(2,4-Diamino-quinazolin-5-yl)-piperazin-1-yl]-p-tolyl-methanone;
5-[4-(Toluene-3-sulfonyl)-piperazin-1-yl]-quinazoline-2,4-diamine; and
[4-(2,4-Diamino-quinazolin-5-yl)-piperazin-1-yl]-(2,4-dichloro-phenyl)-methanone.

In certain embodiments, a 2,4-diaminoquinazoline compound is chosen from among Examples 1-227; in other embodiments, a 2,4-diaminoquinazoline compound is chosen from a compound of Formula (I), with the proviso that the compound is not chosen from among the following compounds:
5-[1-(3,4-dichlorobenzyl)-piperidin-4-ylmethoxy]-quinazoline-2,4-diamine;
5-(Cyclohexylmethoxy)quinazoline-2,4-diamine;
5-(1-Cyclohexyl-ethoxy)-quinazoline-2,4-diamine;
5-(1-Cyclohexylpropoxy)-quinazoline-2,4-diamine;
5-(1-Cyclohexyl-butoxy)-quinazoline-2,4-diamine;
5-(Piperidin-1-yl)quinazoline-2,4-diamine;
5-(Piperidin-4-ylmethoxy)-quinazoline-2,4-diamine;
4-(2,4-diamino-quinazolin-5-yloxymethyl)-piperidin-1-carboxylic acid tert-butyl ester;

(4-Chlorophenyl)-[4-(2,4-diamino-quinazolin-5-yloxymethyl)piperidin-1-yl]-methanone;

(2-Chlorophenyl)-[4-(2,4-diamino-quinazolin-5-yloxymethyl)piperidin-1-yl]-methanone;

(3-Chlorophenyl)-[4-(2,4-diamino-quinazolin-5-yloxymethyl)piperidin-1-yl]-methanone;

[4-(2,4-Diaminoquinazolin-5-yloxymethyl)piperidin-1-yl]-(3-iodophenyl)methanone;

[4-(2,4-Diaminoquinazolin-5-yloxymethyl)piperidin-1-yl]-(4-iodophenyl)methanone; and

[4-(2,4-Diaminoquinazolin-5-yloxymethyl)piperidin-1-yl]-(2-iodophenyl)methanone.

In another aspect, 2,4-diaminoquinazoline compounds according to formula:

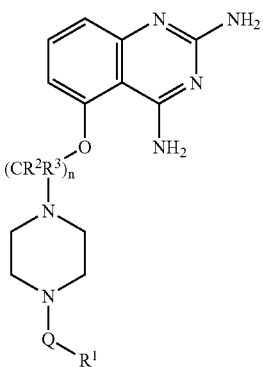

(II)

are provided, wherein Q is selected from the group consisting of: —$CH_2$—; $C(=O)$—; —$SO_2$—; —$CH_2C(=O)$—; —$C(=O)CH_2S$—; and a direct bond, $R^1$ is selected from the group consisting of: H; alkyl; alkoxy; carbocycle; heterocyclyl, substituted carbocycle; substituted heterocyclyl; and fluoroalkyl; $R^2$ or $R^3$ are independently chosen from H or lower alkyl; and n=2 or 3.

In an embodiment of a compound of formula (II), $R^2$ and $R^3$ are H when n is 1; in another embodiment, $R^2$ is H and $R^3$ is H or $CH_3$ when n is 2; in some embodiments, Q is $CH_2$ or —$C(=O)$—, and $R^1$ carbocycle; in some embodiments, the carbocycle is other than phenyl or halophenyl.

In another embodiment of a compound of formula (II), Q is —$SO_2$— or —$C(=O)$—, $R^2$ and $R^3$ are H and n is 2; in some embodiments, $R^1$ is carbocycle or substituted carbocycle, and the compound is Benzo[1,3]dioxol-5-yl-{4-[2-(2,4-diamino-quinazolin-5-yloxy)-ethyl]-piperazin-1-yl}-methanone; in certain embodiments, the substituted carbocycle is monosubstituted or disubstituted phenyl, and the compound is chosen from:

5-{2-[4-(2-Fluoro-benzenesulfonyl)-piperazin-1-yl]-ethoxy}-quinazoline-2,4-diamine;

5-{2-[4-(2,4-Difluoro-benzenesulfonyl)-piperazin-1-yl]-ethoxy}-quinazoline-2,4-diamine; and 5-{2-[4-(3,4-Dichloro-benzenesulfonyl)-piperazin-1-yl]-ethoxy}-quinazoline-2,4-diamine.

In another aspect, 2,4-diaminoquinazoline compounds according to formula:

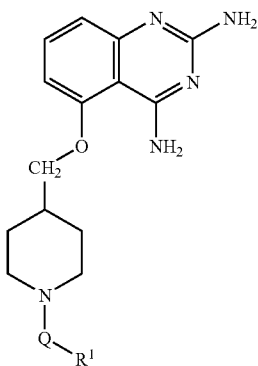

(III)

are provided, wherein Q is chosen from —$CH_2$—, —$C(=O)$—, —$SO_2$—, —$CH_2C(=O)$— and —$SCH_2C(=O)$—; $R^1$ is selected from the group consisting of H, alkyl, alkoxy, carbocycle, heterocyclyl, and substituted heterocyclyl.

In an embodiment of a compound of formula (III), Q is $CH_2$ and $R^1$ is chosen from alkyl, carbocycle, heteroaryl and substituted heteroaryl; in an embodiment the heteroaryl is a pyridine, and the compound is 5-[(1-(pyridine-3-ylmethyl)piperidin-4-ylmethoxy]quinazoline-2,4-diamine.

In other embodiments of a compound of formula (III), Q is chosen from —$CH_2$—$C(=O)$—, —$SO_2$—, —$CH_2C(=O)$— and —$SCH_2C(=O)$—; $R^1$ is selected from the group consisting of H, alkyl, alkoxy, carbocycle, heterocyclyl, substituted carbocycle and substituted heterocyclyl, with the proviso that when $R^1$ is a substituted carbocycle it is a mono substituted phenyl or a 2,6-dihalo substituted phenyl; in certain embodiments, Q is —$CH_2$— and $R^1$ is chosen from alkyl, carbocycle, substituted carbocycle, heteroaryl and substituted heteroaryl; in some embodiments, $R^1$ is substituted carbocycle, and the compound is chosen from:

5-[(1-(2-Fluorobenzyl)piperidin-4-ylmethoxy]quinazoline-2,4-diamine;

5-[1-(2-Chloro-6-fluorobenzyl)piperidin-4-ylmethoxy]quinazoline-2,4-diamine; and 5-[1-(2,6-dichlorobenzyl)piperidin-4-ylmethoxy]quinazoline-2,4-diamine;

in an embodiment, the substituted carbocycle is other than 3-halo substituted phenyl; in another embodiment, the substituted carbocycle is preferably 2-halo substituted phenyl or 2,6-dihalo substituted phenyl, wherein the compound possesses 50% inhibitory concentration (IC50) as measured by human recombinant dihydrofolate reductase assay of 20-100 μM; in other embodiments, the compound possesses 50% inhibitory concentration (IC50) as measured by human recombinant dihydrofolate reductase assay of greater than 100 μM.

In another embodiment of a compound of formula (III), Q is chosen from —$CH_2$—, —$C(=O)$—, —$SO_2$—, —$CH_2C(=O)$— and —$SCH_2C(=O)$—; $R^1$ is selected from the group consisting of H, alkyl, alkoxy, aryl, carbocycle, cycloalkyl, heterocyclyl, substituted cycloalkyl, substituted aryl, substituted carbocycle and substituted heterocyclyl, with the proviso that when $R^1$ is substituted carbocycle it is not a 3,4-dichlorophenyl.

In another aspect, pharmaceutically acceptable salts of any of the compounds disclosed herein, in any stereoisomeric or tautomeric form, and mixtures of any such compounds in any ratio, are provided.

In another aspect, pharmaceutical compositions useful for treating SMA containing a pharmaceutically acceptable carrier and a compound of formula I are provided.

In an embodiment, a 2,4-diaminoquinazoline compound is chosen from any of the compounds disclosed herein, and can be formulated alone or in combination with a therapeutically effective amount of a second drug that improves SMA; in certain embodiments, the second drug that improves SMA is chosen from histone deacetylase inhibitors and methylase inhibitors.

In another aspect, methods of treating SMA by administering a therapeutically effective amount of a 2,4-diaminoquinazoline compound of formula I to a patient are provided.

In an embodiment, a 2,4-diaminoquinazoline compound is chosen from any of the compounds disclosed herein, and can be administered alone or in combination with a therapeutically effective amount of a second drug that improves SMA; in certain embodiments, the second drug that improves SMA is chosen from histone deacetylase inhibitors and methylase inhibitors.

DETAILED DESCRIPTION OF THE INVENTION

As summarized above, the invention relates to 2,4-diaminoquinazoline compounds having formula I, which are useful in the treatment of SMA. The present invention includes a method for treating SMA by administering to a patient suffering from or disposed to SMA a therapeutically effective amount of a 2,4-diaminoquinazoline compound having formula I

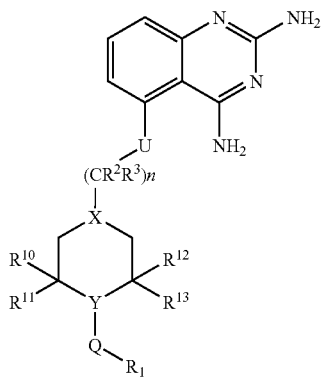

I

In one embodiment, U is oxygen or a bond and X is CH and Y is N, forming a piperidine or piperidinone. In another embodiment, the piperidine can form a glutarimide when $R^{10}$ and $R^{11}$ are =O and $R^{12}$ and $R^{13}$ are =O. In another embodiment, both X and Y can be N, forming a piperazine. In still another embodiment, both X and Y can be CH, forming a cyclohexane. In certain embodiments $R^1$ can be H, alkoxy, carbocycle, substituted carbocycle, heteroaryl or substituted heteroaryl, heterocyclyl or substituted heterocyclyl, fluoroalkyl, and alkoxyalkyl, with the proviso that when $R^1$ is a substituted carbocycle it is not a 3,4-dichlorophenyl. Substituted carbocycles, such as monosubstituted or 2,6-dihalo substituted phenyls, are preferred. In another embodiment, $R^1$ is alkyl, particularly fluoroalkyl.

In another embodiment, the invention provides 2,4-diaminoquinazoline compounds of formula (II):

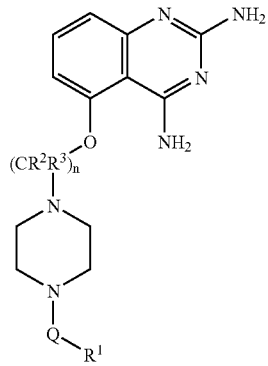

(II)

wherein
Q is selected from the group consisting of: —CH$_2$—; —C(=O)—; —SO$_2$—, CH$_2$C(=O)—; —C(=O)CH$_2$S—; and a direct bond;
$R^1$ is selected from the group consisting of: H; alkyl; alkoxy; carbocycle; heterocyclyl; substituted carbocycle; substituted heterocyclyl; and fluoroalkyl;
$R^2$ or $R^3$ are independently chosen from H or lower alkyl; and n=2 or 3.

In yet another embodiment, the invention provides 2,4-diaminoquinazoline compounds of formula (III)

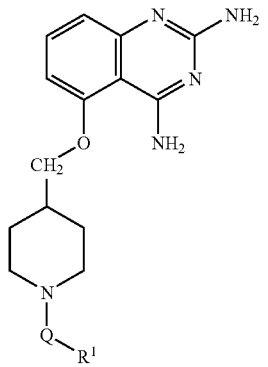

(III)

wherein
Q is chosen from —CH$_2$—, —C(=O)—, —SO$_2$—, —CH$_2$C(=O)— and —SCH$_2$C(=O)—; and
$R^1$ is selected from the group consisting of H, alkyl, alkoxy, carbocycle, heterocyclyl, and substituted heterocyclyl.

In still another embodiment, the invention provides 2,4-diaminoquinazoline compounds of formula:

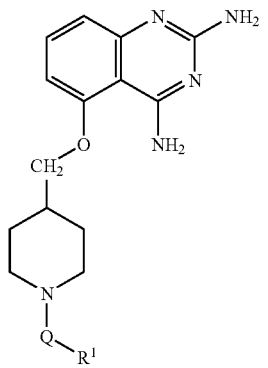

(III)

wherein

Q is chosen from —CH$_2$—, —C(=O)—, —SO$_2$—, —CH$_2$C(=O)— and —SCH$_2$C(=O)—;

R$^1$ is selected from the group consisting of H, alkyl, alkoxy, carbocycle, heterocyclyl, substituted carbocycle and substituted heterocyclyl, with the proviso that when R$^1$ is a substituted carbocycle it is a monosubstituted phenyl or a 2,6-dihalo substituted phenyl.

In another embodiment, the invention provides 2,4-diaminoquinazoline compounds of formula:

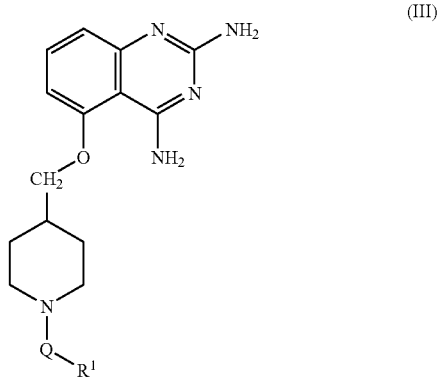

(III)

wherein

Q is chosen from —CH$_2$—, —C(=O)—, —SO$_2$—, —CH$_2$C(=O)— and —SCH$_2$C(=O)—;

R$^1$ is selected from the group consisting of H, alkyl, alkoxy, aryl, carbocycle, cycloalkyl, heterocyclyl, substituted cycloalkyl, substituted aryl, substituted carbocycle and substituted heterocyclyl, with the proviso that when R$^1$ is substituted carbocycle it is not a 3,4-dichlorophenyl.

Various embodiments of the 2,4-diaminoquinazoline compounds disclosed herein exclude compounds of formula I when U is O, n is 1, X and Y are each CH, R$^{10}$-R$^{13}$ are each H, one of R$^2$ and R$^3$ is H and the other is H or lower alkyl, Q is a bond, and R$^1$ is H; in some embodiments, R$^1$ is H or lower alkyl; in certain embodiments, R$^1$-R$^3$ and R$^{10}$-R$^{13}$ are each H or lower alkyl.

Various other embodiments of the 2,4-diaminoquinazoline compounds disclosed herein exclude compounds of formula I when U is O or a bond, n is 1 or 0, one of X and Y is CH and the other is N, R$^1$-R$^3$ and R$^{10}$-R$^{13}$ are each H, and Q is a bond; in some embodiments, R$^1$ is H or lower alkyl; in certain embodiments, R$^1$-R$^3$ and R$^{10}$-R$^{13}$ are each H or lower alkyl.

Various other embodiments of the 2,4-diaminoquinazoline compounds disclosed herein exclude compounds of the following structural formula:

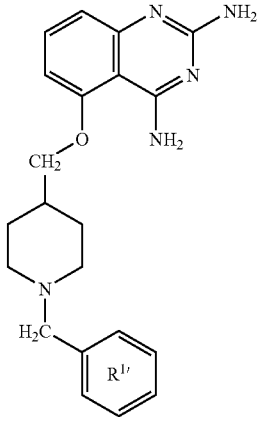

wherein ring R$^{1'}$ includes, as substituents located ortho, meta and para (o, m, p) relative to its benzylic position, m-Cl, p-Cl, and two o-H. In some embodiments of these excluded compounds, substituents of ring R$^{1'}$ include: m-Cl and p-Cl; m-Cl and two o-H; m-(Cl, Br, or I) and two o-H; m-halo and two o-H; m-Cl, p-halo, and two o-H; m-(Cl, Br, or I), p-halo, and two o-H; m-halo, p-halo, and two o-H; m-Cl and p-halo; m-(Cl, Br, or I) and p-halo; m-halo and p-halo; m-Cl; m-Cl, Br, or I; and m-halo.

Various other embodiments of the 2,4-diaminoquinazoline compounds disclosed herein exclude compounds of the following structural formula:

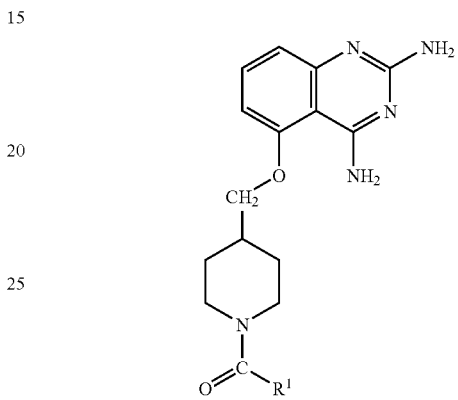

wherein R$^1$ is t-butyloxy or phenyl monosubstituted with Cl or I. In some embodiments of these excluded compounds, R$^1$ is lower alkoxy, or phenyl that is mono substituted with halogen; in certain embodiments, R$^1$ is alkoxy, or phenyl substituted with halogen.

Accordingly, the compounds listed immediately below are exemplary compounds that are excluded from the various embodiments of the 2,4-diaminoquinazoline compounds disclosed herein:

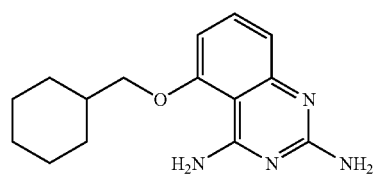

5-(Cyclohexylmethoxy)quinazoline-2,4-diamine

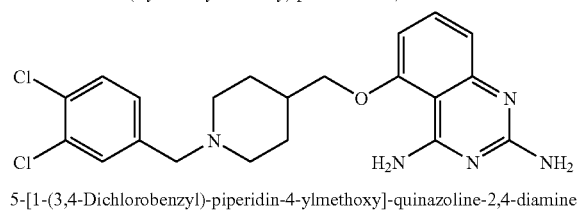

5-[1-(3,4-Dichlorobenzyl)-piperidin-4-ylmethoxy]-quinazoline-2,4-diamine

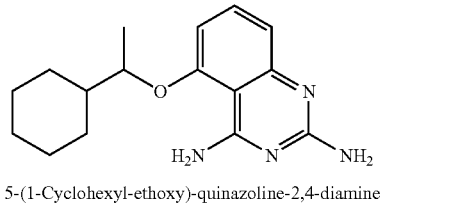

5-(1-Cyclohexyl-ethoxy)-quinazoline-2,4-diamine

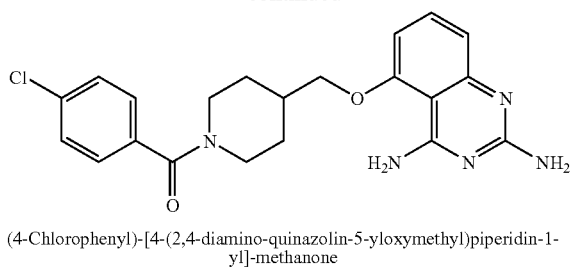

(4-Chlorophenyl)-[4-(2,4-diamino-quinazolin-5-yloxymethyl)piperidin-1-yl]-methanone

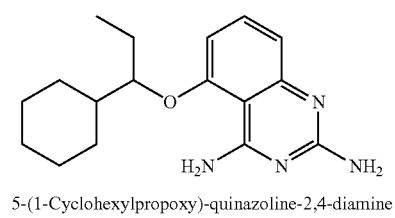

5-(1-Cyclohexylpropoxy)-quinazoline-2,4-diamine

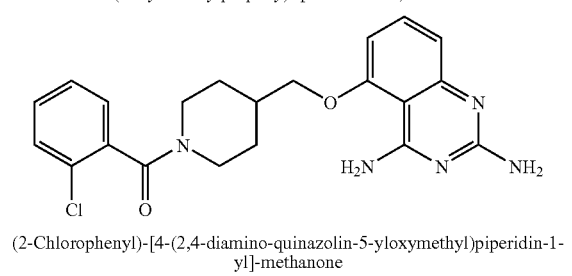

(2-Chlorophenyl)-[4-(2,4-diamino-quinazolin-5-yloxymethyl)piperidin-1-yl]-methanone

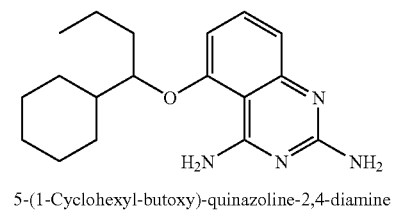

5-(1-Cyclohexyl-butoxy)-quinazoline-2,4-diamine

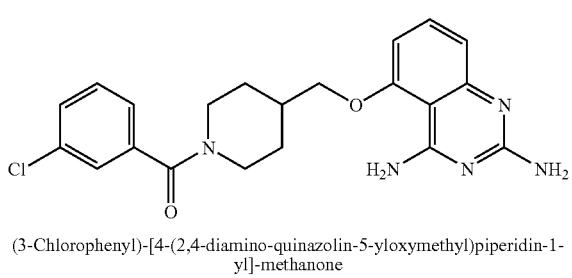

(3-Chlorophenyl)-[4-(2,4-diamino-quinazolin-5-yloxymethyl)piperidin-1-yl]-methanone

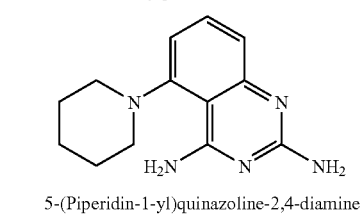

5-(Piperidin-1-yl)quinazoline-2,4-diamine

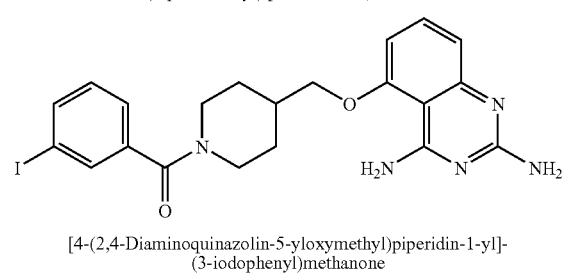

[4-(2,4-Diaminoquinazolin-5-yloxymethyl)piperidin-1-yl]-(3-iodophenyl)methanone

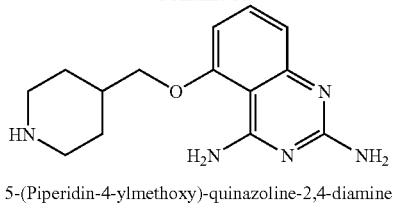

5-(Piperidin-4-ylmethoxy)-quinazoline-2,4-diamine

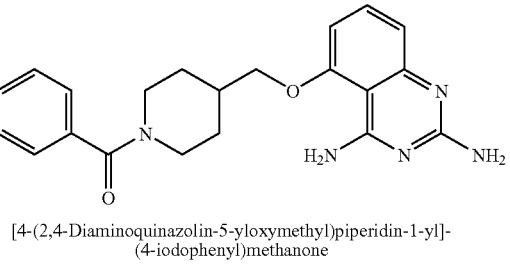

[4-(2,4-Diaminoquinazolin-5-yloxymethyl)piperidin-1-yl]-(4-iodophenyl)methanone

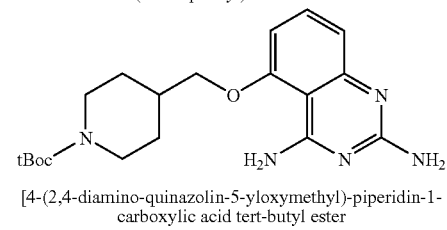

[4-(2,4-diamino-quinazolin-5-yloxymethyl)-piperidin-1-carboxylic acid tert-butyl ester

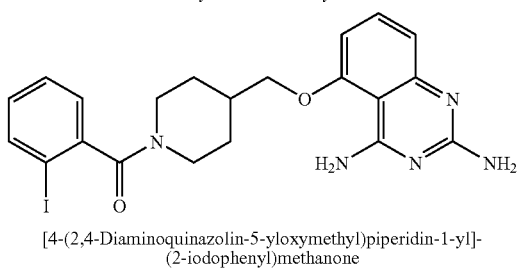

[4-(2,4-Diaminoquinazolin-5-yloxymethyl)piperidin-1-yl]-(2-iodophenyl)methanone

DEFINITIONS

Throughout this specification the terms and substituents retain their definitions.

A comprehensive list of abbreviations utilized by organic chemists (i.e. persons of ordinary skill in the art) appears in the first issue of each volume of the *Journal of Organic Chemistry*. The list, which is typically presented in a table entitled "Standard List of Abbreviations," is incorporated herein by reference.

Alkyl is intended to include linear, branched, or cyclic hydrocarbon structures and combinations thereof. Lower alkyl refers to alkyl groups of from 1 to 6 carbon atoms. Examples of lower alkyl groups include methyl, ethyl, propyl, isopropyl, butyl, s- and t-butyl and the like. Preferred alkyl groups are those of $C_{20}$ or below. Cycloalkyl is a subset of alkyl and includes cyclic hydrocarbon groups having from 3 to 8 carbon atoms, as well as polycyclic hydrocarbons having 7 to 10 carbon atoms. Examples of cycloalkyl groups include c-propyl, c-butyl, c-pentyl, and the like. Examples of $C_7$ to $C_{10}$ polycyclic hydrocarbons include ring systems such as norbornyl and adamantyl.

$C_1$ to $C_{20}$ Hydrocarbon includes alkyl, cycloalkyl, cycloalkenyl, alkenyl, alkynyl, aryl and combinations thereof. Examples include phenethyl, cyclohexylmethyl, camphoryl and naphthylethyl. Examples of cycloalkenyls include cyclohexenyl, nobornenyl, and the like.

"Alkenyl" or "alkenylene" is intended to include hydrocarbon chains of either a straight or branched configuration having the specified number of carbon atoms and one or more unsaturated carbon-carbon bonds which may occur in any stable point along the chain. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either a straight or branched configuration and one or more carbon-carbon triple bonds which may occur in any stable point along the chain, such as ethynyl, propynyl, butynyl, pentynyl, hexynyl and the like.

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Loweralkoxy refers to groups containing one to four carbons.

Oxaalkyl refers to alkyl residues in which one or more carbons has been replaced by oxygen. Examples include methoxypropoxy, 3,6,9-trioxadecyl and the like.

Acyl refers to groups of from 1 to 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to four carbons.

Aryl and heteroaryl mean a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Heterocycle means a cycloalkyl or aryl residue in which from one to three carbons is replaced by a heteroatom selected from the group consisting of N, O and S. The nitrogen and sulfur heteroatoms may optionally be oxidized, and the nitrogen heteroatom may optionally be quaternized. Examples of heterocycles that fall within the scope of the invention include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. It is to be noted that heteroaryl is a sub set of heterocycle in which the heterocycle is aromatic. Examples of heterocyclyl residues additionally include piperazinyl, 2-oxopiperazinyl, 2-oxopiperidinyl, 2-oxo-pyrrolidinyl, 2-oxoazepinyl, azepinyl, 4-piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl, benzothienyl, thiamorpholinyl, thiamorpholinylsulfoxide, thiamorpholinylsulfone, oxadiazolyl, triazolyl and tetrahydroquinolinyl.

Carbocycle is the complement of heterocycle. Carbocycle as used herein means a cycloalkyl or aryl residue in which all of the ring elements are carbon. It includes polycyclic (i.e., two or more rings in which two or more carbons are common to two adjoining rings, e.g., the rings are "fused rings". Examples include cyclohexane, benzene, cyclopentadiene, naphthalene, phenanthrene, fluorene, norbornane, bicycloheptadiene, indane and bicyclooctane.

Substituted alkyl, aryl, cycloalkyl, heterocyclyl, etc. refer to alkyl, aryl, cycloalkyl, or heterocyclyl, etc. wherein up to three H atoms in each residue are replaced with halogen, haloalkyl, hydroxy, lower alkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, halobenzyl, heteroaryl, phenoxy, benzyloxy, heteroaryloxy, benzoyl, halobenzoyl, or lower alkylhydroxy.

The term "halogen" means fluorine, chlorine, bromine or iodine.

It will be understood that "substitution", "substituted" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, and as would be understood by the person of skill in the art, the recitation of "a compound" is intended to include salts, solvates, co-crystals and inclusion complexes of that compound.

The term "solvate" refers to a compound of Formula I in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions. Co-crystals are combinations of two or more distinct molecules arranged to create a unique crystal form whose physical properties are different from those of its pure constituents. Pharmaceutical co-crystals have recently become of considerable interest for improving the solubility, formulation and bioavailability of such drugs as itraconazole [see Remenar et al. J. Am. Chem. Soc. 125, 8456-8457 (2003)] and fluoxetine. Inclusion complexes are described in Remington: The Science and Practice of Pharmacy 19$^{th}$ Ed. (1995) volume 1, page 176-177, which is incorporated herein by reference. The most commonly employed inclusion complexes are those with cyclodextrins, and all cyclodextrin complexes, natural and synthetic, are specifically encompassed within the claims.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. When the compounds contain an acidic side chain, suitable pharmaceutically acceptable base addition salts for the compounds of the present invention include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine.

As used herein, reference to "treatment" of a patient is intended to include palliation and prophylaxis. The term "method of treating" when used herein means amelioration, prevention or relief from the symptoms and/or effects associated with SMA. The term "preventing" as refers to administering a medicament beforehand to forestall or obtund an attack. The person of ordinary skill in the medical art (to which the present invention is directed) recognizes that the term "prevent" is not an absolute term. In the medical art it is understood to refer to the prophylactic administration of a drug to substantially diminish the likelihood or seriousness of a condition, and this is the sense intended when the term is used herein.

The compounds of the invention may also be broadly protective in other motor neuron disorders, such as primary lateral sclerosis, amyotrophic lateral sclerosis and peripheral motor neuron axonopathy as well as neurodegenerative disorders involving other classes of neurons, such as Huntington's disease, Parkinson's disease and Alzheimer's disease.

Compounds described herein may contain one or more asymmetric centers and may thus give rise to enantiomers, diastereomers, and other stereoisomeric forms that may be defined, in terms of absolute stereochemistry, as (R)— or (S)—. The present invention is meant to include all such possible isomers, as well as their racemic and optically pure forms and mixtures thereof in any range or proportion. Optically active (R)— and (S)— forms may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. The configuration of any carbon-carbon double bond appearing herein is selected for convenience only and is not intended to designate a particular configuration; thus a carbon-carbon double bond depicted arbitrarily herein as trans may be cis, trans, or a mixture of the two in any proportion. Likewise, all polymorphs and tautomeric forms are also intended to be included.

Terminology related to "protecting", "deprotecting" and "protected" functionalities occurs throughout this application. Such terminology is well understood by persons of skill in the art and is used in the context of processes which involve sequential treatment with a series of reagents. In that context a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups". Suitable groups for that purpose are discussed in standard textbooks in the field of chemistry, such as *Protective Groups in Organic Synthesis* by T. W. Greene [John Wiley & Sons, New York, 1991], which is incorporated herein by reference.

The 2,4-diaminoquinazoline derivative functionalized at the C5 position may be prepared via the general scheme described by Harris et. al. (J. Med. Chem. 1990, 33, 434-444). Alternatively, a more efficient route may be via reaction of an alcohol (primary, secondary or tertiary), represented by G1a, with 2,6 difluorobenzonitrile, providing the intermediate G2, which upon reaction with guanidine carbonate leads to the C5 functionalized 2,4-diaminoquinazoline, the desired product G3 (Scheme 1). General reaction scheme 1 yields the desired compounds, which bear a heteroatom, oxygen in the examples shown here, at the C5-position of the 2,4-diaminoquinazoline core.

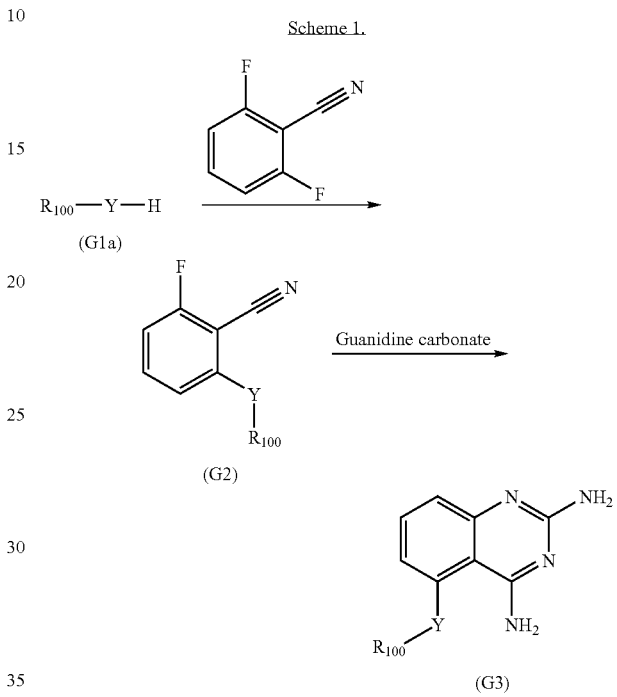

The starting material G1a may either be obtained from commercial sources or may be prepared from numerous procedures outlined in the literature. For example, alcohols may be obtained via reduction of a carboxylic acid, an ester, an aldehyde or a ketone; from olefin via hydroboration or osmylation. The reduction of a ketone with a chiral reducing agent either in catalytic mode or with equimolar use of a chiral reagent provides an alcohol of known chirality with very high % ee.

The heterocyclic intermediates may contain multiple types of functional groups. For example, amino-alcohols (G4) may provide such a key intermediates. A linking heteroatom (Y=O, for example, in G1a) may be reacted first and then the second functional group may be derivatized with an appropriate reagent (G10, where Z=CH2, CHR, C(=O), SO2, CH2-C(=O) etc.) either before construction of the 2,4-diaminoquinazoline core (G7->G13->G11) or after the 2,4 diaminoquinazoline core is constructed (G9->G11). Examples of these approaches are shown in Scheme 2. Functional group(s) may also be introduced after the formation of the 2,4-diaminoquinazoline core.

Synthetic route(s) to the piperazine, piperizone, pyridone, and cycloalkyl analogs is shown in schemes 3, 4, 6a and 6b. The substituted piperidine analogs can be prepared by routes shown in scheme 5 and/or 7. Scheme 7 specifically shows the route for the dimethyl analog starting with commercially available dimethylpyridine N-oxide, which is transformed to the alcohol G1x using the literature procedure (Synth. Comm. (1998), 28(20), 3817-25). The pyridine analog G1y is then reduced (hydrogenated) with rhodium on alumina in ethanol and the piperidine nitrogen is functionalized or protected as shown in schemes above and then elaborated to the final desired products as detailed in generic scheme above and exemplified by specific examples below.

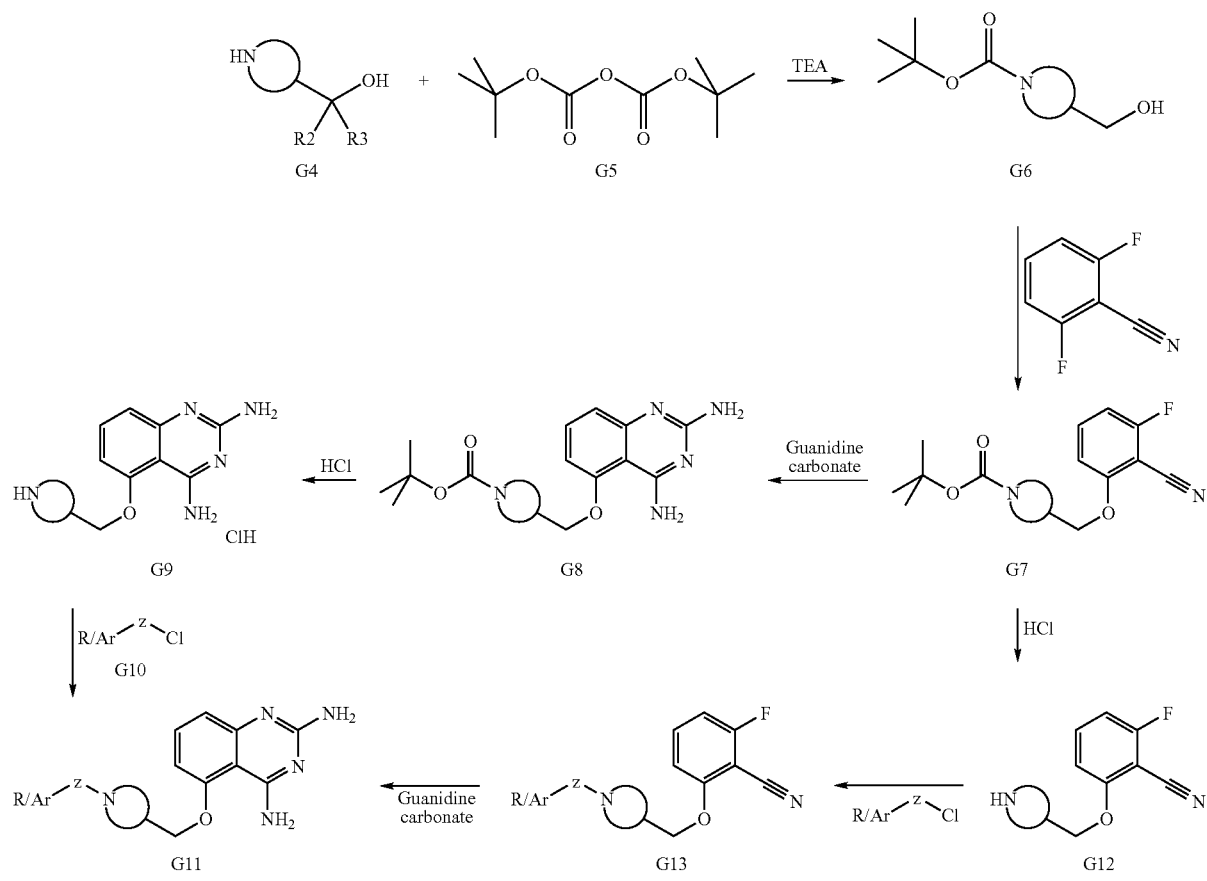
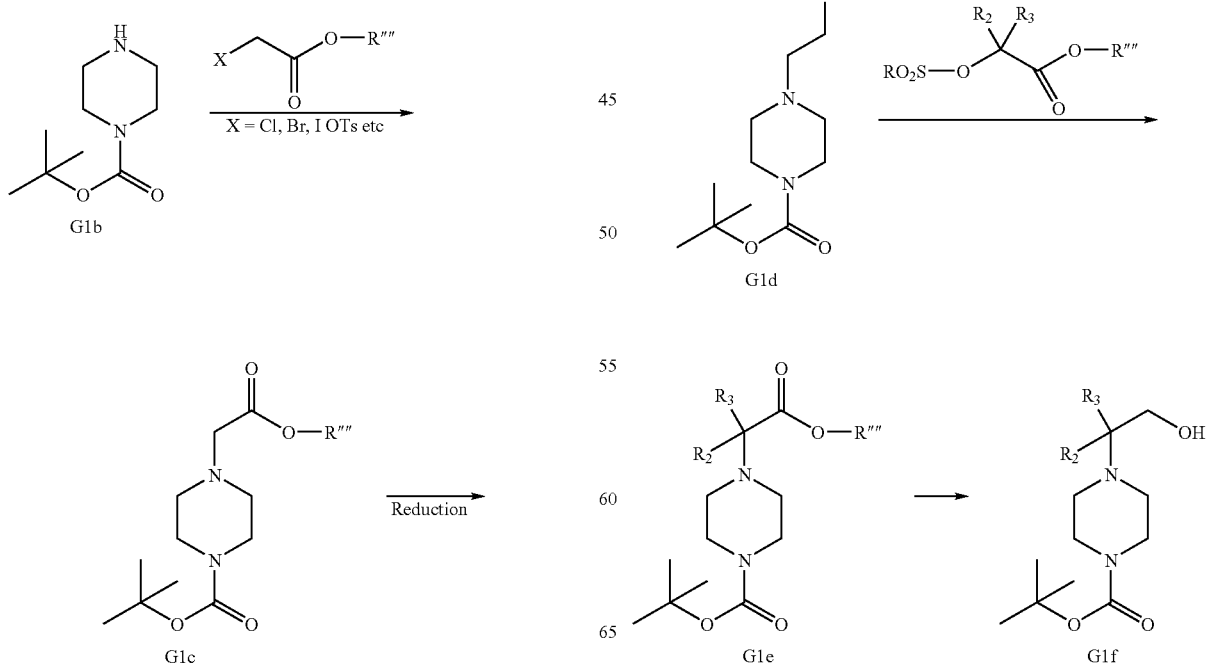

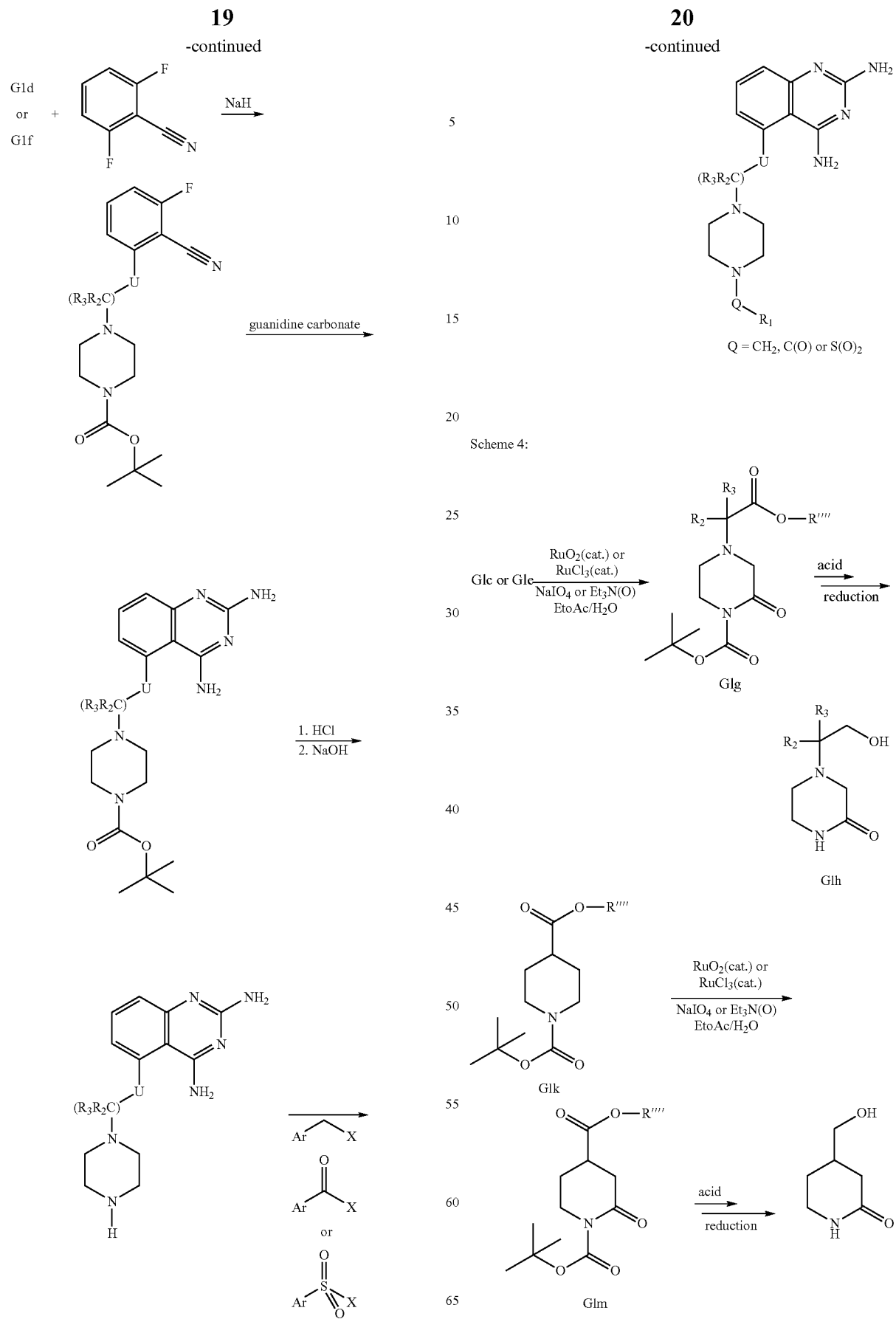

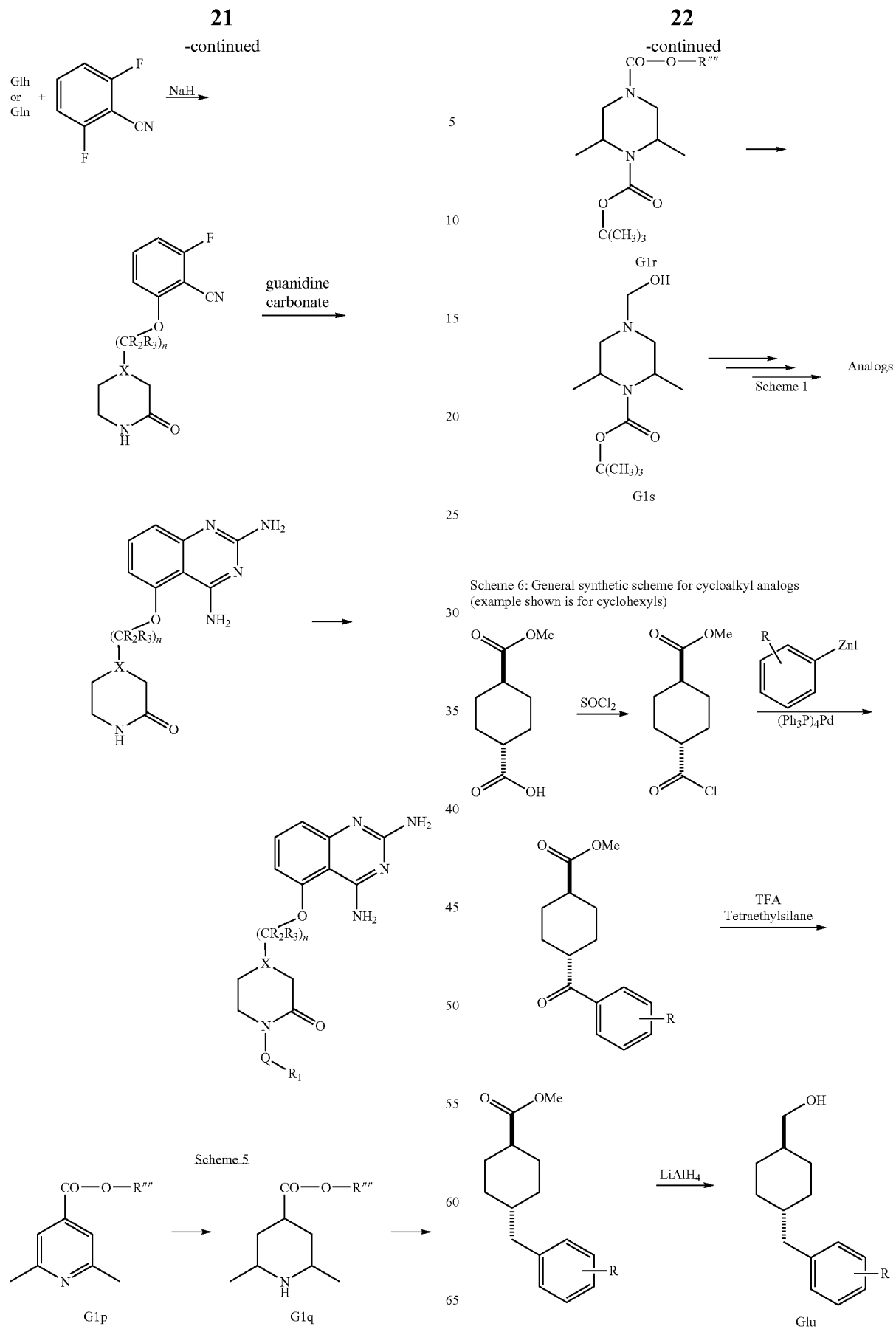

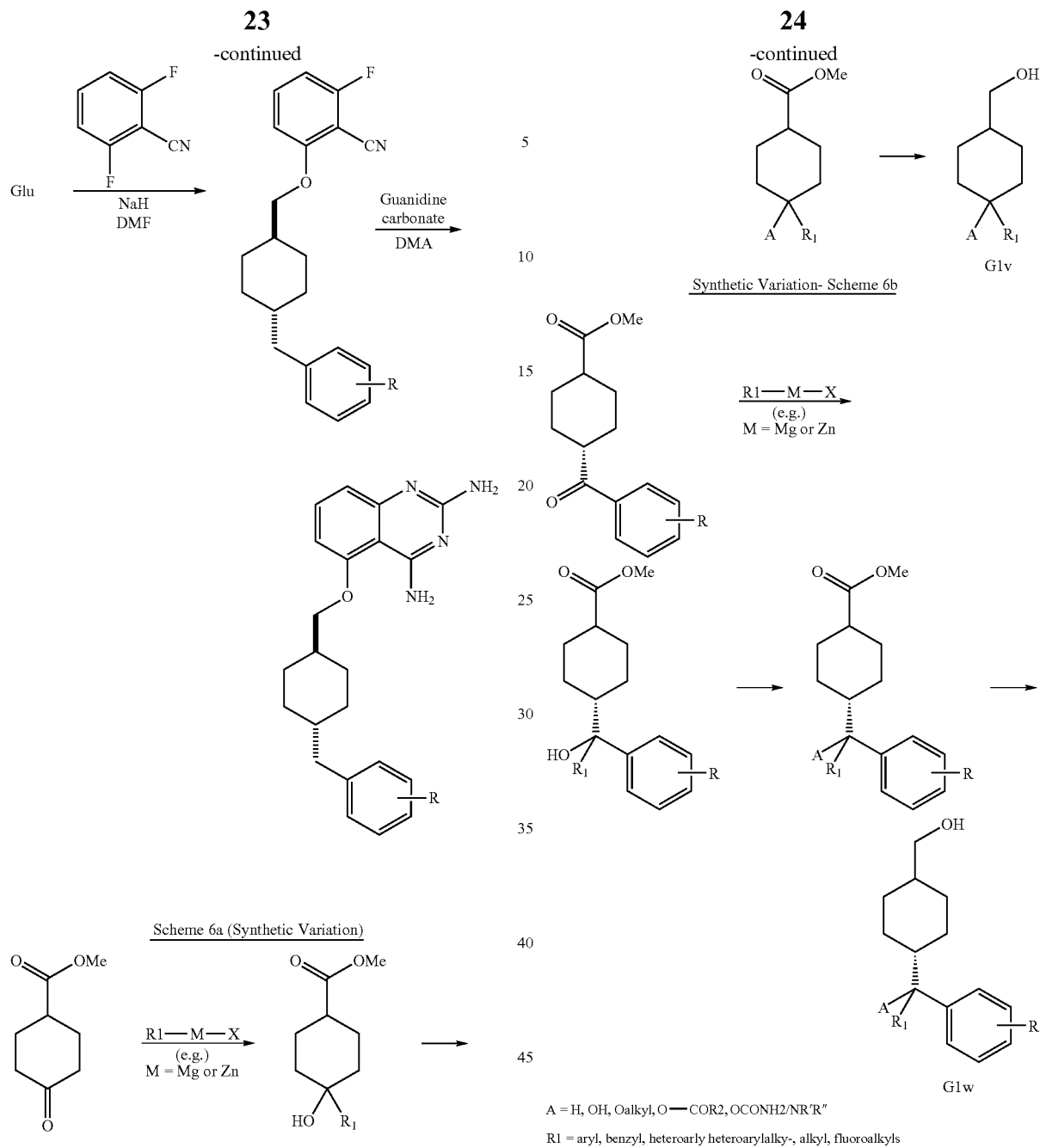
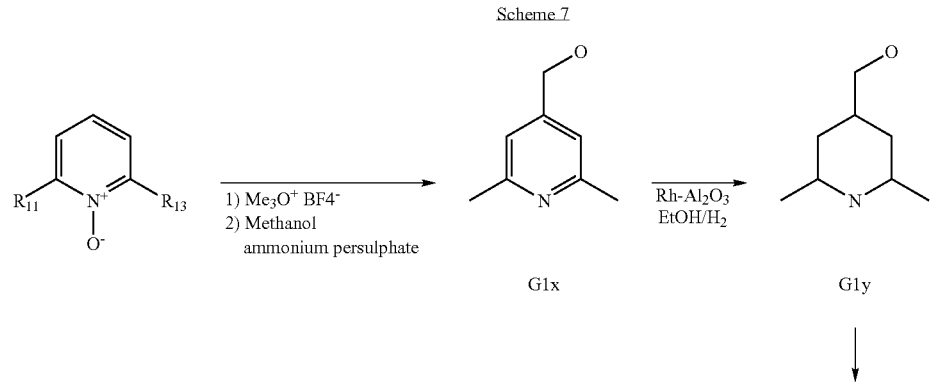

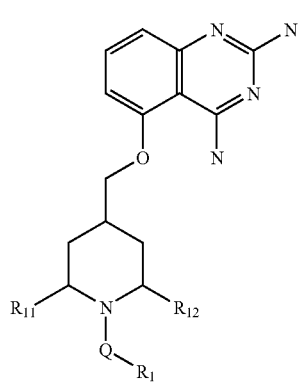
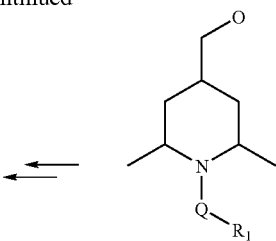
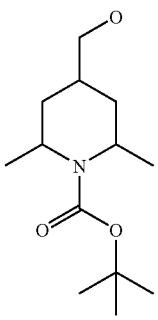

G1z(a)    G1z(b)

Example 226
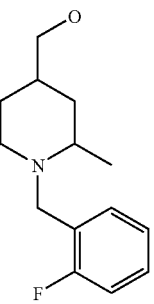

Example shown for R11═R13═CH3, dimethyl analog

All analogs shown in the tables with promoter activity data can be prepared following the information provided above. Experimental for the selected compounds is provided below and the analogs listed in table 1 can be prepared in analogous fashion to these procedures. Reference can also be made to PCT WO2005/123724.

SPECIFIC EXPERIMENTAL FOR REPRESENTATIVE COMPOUNDS/EXAMPLES

4-Hydroxymethylpiperidine-1-carboxylic acid tert-butyl ester. 4-Piperidinemethanol (1.5 g; 13.0 mmol) was dissolved in a mixture of dichloromethane and triethylamine (2.7 mL; 19.5 mmol). Di-tert-butyl dicarbonate (3.1 g; 14.3 mmol) was added such that no bumping occurred. After 2.5 hours reaction was poured over dilute acetic acid and organic layer separated. Organics were washed with water, saturated sodium bicarbonate, brine, and dried over $MgSO_4$. Crude material was purified by flash chromatography using 1-5% methanol/DCM gradient to afford 4-hydroxymethylpiperidine-1-carboxylic acid tert-butyl ester. (2.5 g; 89% yield).

4-(2-Cyano-3-fluorophenoxymethyl)piperidine-1-carboxylic acid tert-butyl ester. The coupling reaction of 4-hydroxymethylpiperidine-1-carboxylic acid tert-butyl ester (1 g; 4.6 mmol) was done according to Method H to yield 1.22 grams of 4-(2-cyano-3-fluorophenoxymethyl)piperidine-1-carboxylic acid tert-butyl ester (81%) after purification by column chromatography (15-20% ethyl acetate/hexanes gradient).

4-(2,4-Diaminoquinazolin-5-yloxymethyl)piperidine-1-carboxylic acid tert-butyl ester. The cyclization of 4-(2-cyano-3-fluorophenoxymethyl)piperidine-1-carboxylic acid tert-butyl ester (17.9 g; 53.5 mmol) was carried out using Method Z to yield 16.4 g (82% yield).

5-(Piperidin-4-ylmethoxy)quinazoline-2,4-diamine. 4-(2,4-Diamino-quinazolin-5-yloxymethyl)-piperidine-1-carboxylic acid tert-butyl ester (16.4 g; 44.0 mmol) was suspended in 80 mL of dioxane and 4M HCl in dioxane (176 mL, 176 mmol) was added changing the mixture from homogenous to heterogenous. After 5 hrs of stirring at room temperature, solids were filtered off and rinsed once with ether. Solids were triturated with 1 N NaOH for 30 minutes. Solids were collected by filtration and dried to yield 5-(piperidin-4-ylmethoxy)quinazoline-2,4-diamine. (9.05 g; 75% yield).

Example-1

[5-(1-(2-Fluorobenzyl)piperidin-4-ylmethoxy]quinazoline-2,4-diamine (Method DD) (Example-001). To a mixture of 5-(piperidin-4-ylmethoxy)quinazoline-2,4-diamine (1.2 g; 4.4 mmol) and triethylamine (1.2 mL; 8.8 mmol) in 10 mL DMF was added 2-fluorobenzyl bromide (0.6 mL; 4.8 mmol) and stirred at 60° C. for 16 hours. Reaction was cooled to room temperature and concentrated at reduced pressure. Residue was taken up in 30 mL dichloromethane and 2 mL of methanol created a homogenous mixture. Material was purified via flash chromatography using a 5-10% MeOH/DCM with 0.1% $NH_4OH$ gradient. Material was then repurified by trituration with 1N NaOH and ethanol for 1.5 hours. Solids were collected by filtration to obtain title compound 740 mg (44% yield). $^1$HNMR (500 MHz, DMSO-$d_6$) δ 7.40 (t, J=7.5 Hz, 1H), 7.31 (m, 1H), 7.18 (m, 3H), 6.77 (d, J=8.0 Hz, 1H), 6.52 (d, J=8.0 Hz, 1H), 5.98 (br s, 2H), 3.97 (d, J=6.0 Hz, 2H), 3.53 (s, 2H), 2.85 (br d, J=11.5 Hz, 2H), 2.01 (t, J=10 Hz, 2H), 1.84 (m, 1H), 1.73 (d, J=12 Hz, 2H), 1.34 (m, 2H). MS m/z (ESI) 382 (M+H)$^+$. Anal. ($C_{21}H_{24}FN_5O$) C, H, N.

Example-2

5-[1-(3-chlorobenzyl)-piperidin-4-ylmethoxy]-quinazoline-2,4-diamine (Example-002). To a stirred solution of 5-(piperidin-4-ylmethoxy)quinazoline-2,4-diamine (2.5 g, 9.15 mmol) and diisopropylethylamine (2.96 g, 22.87 mmol) in DMF (16 mL) was added a solution of 3-chlorobenzyl bromide in DMF (4 mL). The reaction mixture was heated at 60° C. with stirring for 20 h. The mixture was concentrated, water was added stirred for 1 h. The precipitate was filtered, washed with water, dried. Purified by silica gel column chromatography using 3-10% methanol in dichloromethane afforded 1.82 g of 5-[1-(3-chlorobenzyl)piperidin-4-ylmethoxy]quinazoline-2,4-diamine $^1$H NMR (400 MHz, DMSO-$d_6$) δ 7.25-7.38 (m, 5H), 7.2 (s, 2H), 6.77 (dd, J=8.0, 1.2 Hz, 1H), 6.53 (dd, J=8.0, 0.8 Hz, 1H), 5.95 (s, 2H), 3.99 (d, J=6.4 Hz, 2H), 3.48 (s, 2H), 2.84 (d, J=11.2 Hz, 2H), 1.7-2.07 (m, 5H), 1.3-1.42 9m, 2H). MS m/z (ESI) 399 (M+H)$^+$.

Example-3

[5-(1-(2-Chlorobenzyl)piperidin-4-ylmethoxy]quinazoline-2,4-diamine (Example-003). To a mixture of 5-(piperidin-4-ylmethoxy)quinazoline-2,4-diamine (1.0 g; 3.7 mmol) and triethylamine (1.3 mL, 9.2 mmol) in 10 mL N,N-dimethylformamide was added 2-chlorobenzyl bromide (0.5 mL; 3.7 mmol) and stirred at 60° C. for 16 hours. Reaction was cooled to room temperature and solvent volume was reduced by half in vacuo. Mixture was poured into 4 mL 1N NaOH and precipitated with an additional 15 mL water. Purification of filtered solids was reprecipitated from methanol and dichloromethane (2:1). Mixture was allowed to sit overnight. Solids were filtered off and rinsed once with methanol and twice with diethyl ether to yield title compound. (684 mg; 47% yield). 1 (400 MHz, DMSO-$d_6$) δ 7.49 (d, J=7.6 Hz, 1H), 7.41 (d, J=7.6 Hz, 1H), 7.32 (m, 3H), 7.2 (br s, 2H), 6.76 (d, J=7.6 Hz, 1H), 6.53 (d, J=7.6 Hz, 1H), 5.94 (br s, 2H), 3.99 (d, J=6.0 Hz, 2H), 3.57 (s, 2H), 2.89 (m, 2H), 2.08 (t, J=12 Hz, 2H), 1.89 (m, 1H), 1.75 (d, J=12 Hz, 2H), 1.36 (m, 2H). MS m/z (ESI) 398 (M+H)$^+$.

Example-4

5-[1-(4-Chlorobenzyl)piperidin-4-ylmethoxy]quinazoline-2,4-diamine hydrochloride (Example-004). The benzylamine was obtained by reacting 5-(piperidin-4-ylmethoxy)quinazoline-2,4-diamine (75 mg; 0.27 mmol) and 4-chlorobenzyl bromide (66 mg; 0.32 mmol) via Method BB to a solid, which was stirred in the presence of 4M HCl in dioxane (4 eq). Solids were filtered and rinsed once with ether to give title compound. (66 mg; 56% yield). $^1$HNMR (400 MHz, DMSO-$d_6$) δ 12.9 (s, 1H), 11.3 (s, 1H), 8.82 (s, 1H), 8.23 (s, 1H), 7.7 (m, 4H), 7.52 (d, J=6.8 Hz, 2H), 7.02 (m, 2H), 4.66 (br s, 3H), 4.26 (d, J=4.8 Hz, 2H), 4.17 (d, J=6.4 Hz, 2H), 3.34 (br d, J=11.6 Hz, 2H), 2.87 (m, 2H), 2.2 (m, 1H), 1.81 (m, 4H). MS m/z (ESI) 398 (M+H)$^+$.

Example-5

5-[1-(1-Naphthalen-1-ylmethylpiperidin-4-ylmethoxy]quinazoline-2,4-diamine (Example-005). The naphthylamine was obtained by reacting 5-(piperidin-4-ylmethoxy)quinazoline-2,4-diamine (75 mg; 0.27 mmol) and 1-(chloromethyl)naphthalene (57 mg; 0.32 mmol) via Method BB to yield 94 mg. (84% yield). $^1$HNMR (400 MHz, DMSO-$d_6$) δ 8.26 (d, J=8.0 Hz, 1H), 7.85 (m, 2H), 7.53 (m, 3H), 7.44 (d, J=4.8 Hz, 1H), 7.33 (t, J=8.4 Hz, 1H), 7.19 (br s, 2H), 6.75 (d, J=8.4 Hz, 2H), 6.51 (d, J=8.0 Hz, 1H), 5.94 (br s, 2H), 3.79 (d, J=6.4 Hz, 2H), 3.87 (s, 2H), 2.92 (d, J=11.2 Hz, 2H), 2.07 (t, J=11.6 Hz, 2H), 1.91 (m, 1H), 1.74 (d, J=12.4 Hz, 2H), 1.3 (m, 2H). MS m/z (ESI) 414 (M+H)$^+$.

Example-6

5-[1-(2-Naphthalen-1-ylmethylpiperidin-4-ylmethoxy]quinazoline-2,4-diamine (Example-006). The naphthylamine was obtained by reacting 5-(piperidin-4-ylmethoxy)quinazoline-2,4-diamine (75 mg; 0.27 mmol) and 2-(bromomethyl)naphthalene (77 mg; 0.35 mmol) via Method BB to yield 75 mg. (67% yield). $^1$HNMR (400 MHz, DMSO-$d_6$) δ 7.88 (m, 3H), 7.79 (s, 1H), 7.48 (m, 3H), 7.34 (t, J=8.0 Hz, 1H), 7.22 (br s, 2H), 6.76 (d, J=8.0 Hz, 1H), 6.53 (d, J=7.6 Hz, 1H), 5.96 (br s, 2H), 3.99 (d, J=6.0 Hz, 2H), 3.64 (s, 2H), 2.92 (m, 2H), 2.03 (t, J=10.8 Hz, 2H), 1.91 (m, 1H), 1.74 (d, J=12.0 Hz, 2H), 1.37 (m, 2H). MS m/z (ESI) 414 (M+H)$^+$.

Example-7

5-[1-(2-Methylbenzyl)piperidin-4-ylmethoxy]quinazoline-2,4-diamine (Example-007). The benzylamine was obtained by reacting 5-(piperidin-4-ylmethoxy)quinazoline-2,4-diamine (75 mg; 0.27 mmol) and 2-methylbenzyl bromide (65 mg; 0.35 mmol) via Method BB to yield 91 mg. (89% yield). $^1$HNMR (400 MHz, DMSO-$d_6$) δ 7.34 (t, J=8.0 Hz, 1H), 7.21 (m, 3H), 7.14 (m, 3H), 6.76 (d, J=8.0 Hz, 1H), 6.52 (d, J=8.4 Hz, 11H), 5.94 (br s, 2H), 3.98 (d, J=6.4 Hz, 2H), 3.41 (s, 3H), 2.83 (br, d, J=11.6 Hz, 2H), 2.32 (s, 3H), 2.00 (t, J=10.4 Hz, 2H), 1.9 (m, 1H), 1.73 (d, J=12.8 Hz, 2H), 1.31 (m, 2H). MS m/z (ESI) 378 (M+H)$^+$.

Example-8

5-[1-(3-Methylbenzyl)piperidin-4-ylmethoxy]quinazoline-2,4-diamine (Example-008). The benzylamine was obtained by reacting 5-(piperidin-4-ylmethoxy)quinazoline-2,4-diamine (75 mg; 0.27 mmol) and 3-methylbenzyl bromide (60 mg; 0.32 mmol) via Method BB to yield 86 mg. (84% yield). $^1$HNMR (400 MHz, DMSO-$d_6$) δ 7.34 (t, J=8.0 Hz, 1H), 7.2 (m, 3H), 7.07 (m, 3H), 6.76 (d, J=8.4 Hz, 1H), 6.52 (d, J=8.0 Hz, 1H), 5.94 (br s, 2H), 3.98 (d, J=6.0 Hz, 2H), 3.42 (s, 2H), 2.83 (br d, J=11.2 Hz, 2H), 2.29 (s, 3H), 1.8 (m, 5H), 1.36 (m, 2H). MS m/z (ESI) 378 (M+H)$^+$.

Example-9

5-[1-(4-Methylbenzyl)piperidin-4-ylmethoxy]quinazoline-2,4-diamine hydrochloride (Example-009). The benzylamine was obtained by reacting 5-(piperidin-4-ylmethoxy)quinazoline-2,4-diamine (75 mg; 0.27 mmol) and 4-methylbenzyl bromide (60 mg; 0.32 mmol) via Method BB to a solid, which was stirred in the presence of 4M HCl in dioxane (4 eq). Solids were filtered and rinsed once with ether to give title compound. (101 mg; 90% yield). $^1$HNMR (400 MHz, DMSO-$d_6$) δ 12.8 (s, 1H), 11.0 (s, 1H), 8.82 (s, 1H), 8.23 (s, 1H), 7.69 (m, 2H), 7.5 (d, J=8.0 Hz, 2H), 7.25 (d, J=8.0 Hz, 2H), 4.91 (br s, 2H), 4.17 (m, 4H), 3.36 (br d, J=11.6 Hz, 2H), 2.85 (m, 2H), 2.33 (s, 3H), 2.2 (m, 1H), 1.79 (m, 4H). MS m/z (ESI) 378 (M+H)$^+$.

Example-10

5-[1-(2,4-Difluorobenzyl)piperidin-4-ylmethoxy]quinazoline-2,4-diamine hydrochloride (Example-010). The benzylamine was obtained by reacting 5-(piperidin-4-ylmethoxy)quinazoline-2,4-diamine (75 mg; 0.27 mmol) and 2,4-difluorobenzyl chloride (69 mg; 0.35 mmol) via Method BB. Solids were suspended in 2 mL dioxane and 0.5 mL 4M HCl in dioxane was added and after 2 hours stirring at room temperature solids were collected by filtration to yield 92 mg. (78% yield). $^1$HNMR (400 MHz, DMSO-$d_6$) δ 12.8 (s, 1H), 11.2 (s, 1H), 8.84 (s, 1H), 8.23 (s, 1H), 7.88 (q, J=8.8, 6.4 Hz, 1H), 7.7 (m, 2H), 7.4 (m, 1H), 7.23 (m, 1H), 7.02 (m, 2H), 4.28 (d, J=4.4 Hz, 2H), 4.17 (d, J=6.4 Hz, 2H), 3.4 (br d, J=11.6 Hz, 2H), 2.95 (m, 2H), 2.23 (m, 1H), 1.81 (d, J=13.2 Hz, 2H), 1.73 (m, 2H). MS m/z (ESI) 400 (M+H)$^+$.

Example-11

5-[1-(3,4-Difluorobenzyl)piperidin-4-ylmethoxy] quinazoline-2,4-diamine (Method BB) (Example-011). 5-(Piperidin-4-ylmethoxy)quinazoline-2,4-diamine (50 mg; 0.18 mmol) was shaken for 60 hours at 60° C. in the presence of 3-(morpholino)propyl polystyrene sulfonamide (PS-NMM) (160 mg; 0.4 mmol) and 3,4-difluorobenzyl bromide (77 mg; 0.37 mmol) in 4 mL N,N-dimethylformamide. Tris-(2-aminoethyl)aminomethyl polystyrene (PS-Trisamine) (112 mg; 0.4 mmol) was then added to the mixture and continued to shake for an additional 2 hours. Resins were filtered off and rinsed with methanol. Filtrate was concentrated at reduced pressure, and residue was triturated with 2 mL 1 N NaOH and ethanol (1:1). Solids were collected by filtration to yield 5-[1-(3,4-difluorobenzyl)piperidin-4-ylmethoxy]quinazoline-2,4-diamine (30 mg; 42% yield). $^1$HNMR (400 MHz, DMSO-d$_6$) δ 7.61 (m, 2H), 7.34 (m, 2H), 7.14 (m, 2H), 6.76 (m, 1H), 6.52 (m, 1H), 5.94 (br s, 2H), 3.99 (d, J=6.0 Hz, 2H), 3.46 (s, 3H), 3.12 (m, 1H), 2.82 (br d, J=10.8 Hz, 1H), 2.11 (m, 2H), 1.95 (m, 2H), 1.73 (br d, J=11.2 Hz, 1H), 1.34 (m, 1H). MS m/z (ESI) 400 (M+H)$^+$.

Example-12

5-[1-(2,3-Difluorobenzyl)piperidin-4-ylmethoxy] quinazoline-2,4-diamine (Example-012). The benzylamine was obtained by reacting 5-(piperidin-4-ylmethoxy)quinazoline-2,4-diamine (50 mg; 0.18 mmol) and 2,3-difluorobenzyl bromide (77 mg; 0.37 mmol) via Method BB to yield 38 mg. (53% yield). $^1$HNMR (400 MHz, DMSO-d$_6$) δ 8.26 (br s, 1H), 7.8 (br s, 1H), 7.55 (t, J=8.4 Hz, 1H), 7.33 (m, 1H), 7.2 (m, 2H), 6.99 (br s, 2H), 6.9 (d, J=8 Hz, 1H), 6.81 (d, J=8.0 Hz, 2H), 4.07 (d, J=6.4 Hz, 2H), 3.59 (s, 2H), 2.85 (m, 2H), 2.04 (t, J=11.2 Hz, 2H), 1.9 (m, 1H), 1.73 (d, J=10.4 Hz, 2H), 1.33 (m, 2H). MS m/z (ESI) 400 (M+H)$^+$.

Example-13

[4-(2,4-Diaminoquinazolin-5-yloxymethyl)piperidin-1-yl](2-fluorophenyl)methanone (Example-013). The amidation of 5-(piperidin-4-ylmethoxy)quinazoline-2,4-diamine (50 mg; 0.18 mmol) was carried out using Method AA using 2-fluorobenzoyl chloride (57 mg; 0.36 mmol) via Method AA to yield 43 mg. (60% yield). $^1$HNMR (400 MHz, DMSO-d$_6$) δ 7.49 (m, 1H), 7.33 (m, 4H), 7.17 (br s, 2H), 6.77 (d, J=8.0 Hz, 1H), 6.54 (d, J=8.0 Hz, 1H), 5.94 (br s, 2H), 4.56 (br d, J=12.8 Hz, 1H), 4.03 (d, J=6.0 Hz, 2H), 3.42 (br d, J=12.8 Hz, 1H), 3.12 (m, 1H), 2.86 (t, J=11.2 Hz, 1H), 2.22 (br s, 1H), 1.89 (br d, J=13.6 Hz, 1H), 1.73 (br d, J=11.2 Hz, 1H), 1.26 (m, 2H). MS m/z (ESI) 396 (M+H)$^+$.

Example-14

2-[1-(3-Chlorobenzoyl)piperidin-4-ylmethoxy-6-fluorobenzonitrile. The reaction of 2-fluoro-6-(piperidin-1-ylmethoxy)benzonitrile hydrochloride and 3-chlorobenzoyl chloride (129 mg; 0.7 mmol) was carried out using Method Y to yield 200 mg (77% yield).
(3-Chlorophenyl)-[4-(2,4-diaminoquinazolin-5-yloxymethyl)piperidin-1-yl]methanone (Example-014). The cyclization of 2-[1-(3-chlorobenzoyl)piperidin-4-ylmethoxy-6-fluorobenzonitrile (194 mg; 0.5 mmol) and guanidine carbonate was carried out Method Z to yield 169 mg (82% yield). $^1$HNMR (400 MHz, DMSO-d$_6$) δ 7.51 (m, 3H), 7.35 (m, 2H), 7.19 (br d, J=16.4 Hz, 2H), 6.77 (dd, J=8.4, 0.8 Hz, 1H), 6.57 (d, J=8.0 Hz, 1H), 5.98 (br s, 2H), 4.51 (br s, 1H), 4.03 (d, J=6.4 Hz, 2H), 3.55 (br s, 1H), 3.11 (m, 1H), 2.84 (br s, 1H), 2.22 (m, 1H), 1.88 (br s, 1H), 1.75 (br s, 1H), 1.33 (br s, 2H). MS m/z (ESI) 412 (M−H)$^+$.

Example-15

2-Fluoro-6-(piperidin-1-ylmethoxy)benzonitrile hydrochloride. 4-(2-Cyano-3-fluorophenoxymethyl)piperidine-1-carboxylic acid tert-butyl ester (920 mg, 2.8 mmol) was dissolved in 5 mL of dioxane, and 3 mL of 4M HCl in dioxane was added over 1 minute at room temperature. Reaction stirred for 5 hrs and white precipitate was collected by filtration. Solids rinsed once with cold ether and dried to afford 2-fluoro-6-(piperidin-1-ylmethoxy)benzonitrile hydrochloride. (500 mg; 66% yield).
2-[1-(2-Chlorobenzoyl)piperidin-4-ylmethoxy]-6-fluorobenzonitrile. The reaction of 2-fluoro-6-(piperidin-1-ylmethoxy)benzonitrile hydrochloride and 2-chlorobenzoyl chloride (129 mg; 0.7 mmol) was carried out using Method Y to yield 225 mg (86% yield).
(2-Chlorophenyl)-[4-(2,4-diaminoquinazolin-5-yloxymethyl)piperidin-1-yl]methanone (Example-015). The cyclization of 2-[1-(2-chlorobenzoyl)-piperidin-4-ylmethoxy]-6-fluoro-benzonitrile (219 mg, 0.6 mmol) and guanidine carbonate was carried out using Method Z to afford 70.6 mg of title compound (29% yield). $^1$HNMR (400 MHz, DMSO-d$_6$) δ 7.52 (m, 1H), 7.43 (m, 3H), 7.36 (t, J=8.4 Hz, 1H), 7.2 (m, 2H), 6.77 (d, J=8.4 Hz, 1H), 6.57 (t, J=7.2 Hz, 1H), 6.0 (br s, 2H), 4.56 (br d, J=12 Hz, 1H), 4.03 (d, J=6 Hz, 2H), 3.28 (m, 1H), 3.05 (m, 1H), 2.85 (t, J=12.8 Hz, 1H), 2.23 (m, 1H), 1.91 (m, 1H), 1.72 (t, J=13.6 Hz, 1H), 1.33 (m, 2H). MS m/z (ESI) 412 (M−H)$^+$.

Example-16

2-[1-(4-Chlorobenzoyl)piperidin-4-ylmethoxy]-6-fluorobenzonitrile-(Method Y). 2-Fluoro-6-(piperidin-1-ylmethoxy)benzonitrile hydrochloride (122 mg; 0.45 mmol) was suspended in 2 mL of tetrahydrofuran, and in one portion triethylamine was added (0.2 mL. 1.4 mmol) to the mixture at room temperature. 4-Chlorobenzoyl chloride (0.06 mL; 0.45 mmol) was then added, and stirred at room temperature for 16 hrs. Reaction was quenched with 2 mL 1 N HCl. Mixture was extracted twice with 10 mL of ethyl acetate and organic layers combined. Mixture was then washed with sat. NaHCO$_3$, brine and dried over MgSO$_4$. Mixture was filtered and concentrated to an oil. Material was purified via flash silica gel chromatography using 0.5-2% methanol/dichloromethane gradient to afford 2-[1-(4-chlorobenzoyl)piperidin-4-ylmethoxy]-6-fluorobenzonitrile as an oil. (120 mg; 71% yield).
(4-Chlorophenyl)-[4-(2,4-diaminoquinazolin-5-yloxymethyl)piperidin-1-yl]methanone (Method Z) (Example-016). 2-[1-(4-Chlorobenzoyl)piperidin-4-ylmethoxy]-6-fluorobenzonitrile (110 mg, 0.3 mmol) and guanidine carbonate (53 mg; 0.3 mmol) were heated at 140° C. in dimethylacetamide for 4 hours. The mixture was cooled and triturated with water for 45 minutes. Solids were filter off and triturated with 3 mL of ethanol. Solids were collected by filtration and dried to afford 75 mg of title compound (59% yield) $^1$HNMR (400 MHz, DMSO-d$_6$) δ 7.52 (m, 2H), 7.43 (m, 2H), 7.35 (t, J=8.4 Hz, 1H), 7.17 (br d, J=15.2 Hz, 2H), 6.77 (dd, J=8.4, 0.8 Hz, 1H), 6.54 (d, J=7.2 Hz, 1H), 5.95 (br s, 2H), 4.51 (br s, 1H), 4.03 (d, J=6.4 Hz, 2H), 3.59 (br s, 1H), 3.11 (br s, 1H), 2.84 (br s, 1H), 2.22 (m, 1H), 1.87 (br s, 1H), 1.76 (br s, 1H), 1.3 (br d, J=10.4 Hz, 2H). MS m/z (ESI) 412 (M–H)$^+$.

Example-17

[4-(2,4-Diaminoquinazolin-5-yloxymethyl)piperidin-1-yl]naphthalen-1-ylmethanone (Example-017). The amidation of 5-(piperidin-4-ylmethoxy)quinazoline-2,4-diamine (50 mg; 0.18 mmol) was carried out using 1-naphthoyl chloride (70.5 mg; 0.37 mmol) via Method AA to yield 152 mg. (96% yield). $^1$HNMR (400 MHz, DMSO-d$_6$) δ 7.99 (m, 2H), 7.82 (m, 1H), 7.56 (m, 2H), 7.41 (m, 1H), 7.34 (m, 2H), 7.12 (br s, 2H), 6.76 (d, J=8.0 Hz, 1H), 6.54 (d, J=8.0 Hz, 1H), 5.94 (br s, 2H), 4.74 (t, J=12.0 Hz, 1H), 4.04 (d, J=6.0 Hz, 2H), 3.25 (br d, J=12.4 Hz, 1H), 3.00 (m, 2H), 2.22 (s, 1H), 1.97 (m, 1H), 1.63 (m, 1H), 1.44 (m, 1H), 1.3 (m, 1H). MS m/z (ESI) 428 (M+H)$^+$.

Example-18

[4-(2,4-Diaminoquinazolin-5-yloxymethyl)piperidin-1-yl]naphthalen-2-yl-methanone (Example-018). The amidation of 5-(piperidin-4-ylmethoxy)quinazoline-2,4-diamine (50 mg; 0.18 mmol) was carried out using 2-naphthoyl chloride (70.5 mg; 0.37 mmol) via Method AA to yield 139 mg. (88% yield). $^1$HNMR (400 MHz, DMSO-d$_6$) δ 7.97 (m, 4H), 7.58 (m, 2H), 7.50 (dd, J=8.4, 1.6 Hz, 1H), 7.35 (t, J=8.4 Hz, 1H), 7.2 (br s, 2H), 6.76 (d, J=8.0 Hz, 1H), 6.55 (d, J=8.0 Hz, 1H), 5.94 (br s, 2H), 4.59 (br s, 1H), 4.04 (d, J=6.0 Hz, 2H), 3.72 (br s, 1H), 3.15 (br s, 1H), 2.91 (br s, 1H), 2.24 (m, 1H), 1.9 (br s, 1H), 1.75 (br s, 1H), 1.35 (m, 2H). MS m/z (ESI) 428 (M+H)$^+$.

Example-19

[4-(2,4-Diaminoquinazolin-5-yloxymethyl)piperidin-1-yl]-o-tolylmethanone (Example-019). The amidation of 5-(piperidin-4-ylmethoxy)quinazoline-2,4-diamine (50 mg; 0.18 mmol) was carried out using o-toluoyl chloride (57 mg; 0.37 mmol) via Method AA to yield 101 mg. (70% yield). $^1$HNMR (400 MHz, DMSO-d$_6$) δ 7.35 (t, J=8.4 Hz, 1H), 7.25 (m, 6H), 6.76 (d, J=8.0 Hz, 1H), 6.54 (d, J=8.0 Hz, 1H), 5.94 (br s, 2H), 4.59 (br d, J=13.2 Hz, 1H), 4.03 (d, J=6.0 Hz, 2H), 3.3 (m, 1H), 3.04 (t, J=11.6 Hz, 1H), 2.88 (t, J=12.0 Hz, 1H), 2.23 (m, 4H), 1.89 (br d, J=13.2 Hz, 1H), 1.69 (m, 1H), 1.24 (m, 2H). MS m/z (ESI) 392 (M+H)$^+$.

Example-20

[4-(2,4-Diaminoquinazolin-5-yloxymethyl)piperidin-1-yl]-m-tolylmethanone (Example-020). The amidation of 5-(piperidin-4-ylmethoxy)quinazoline-2,4-diamine (50 mg; 0.18 mmol) was carried out using m-toluoyl chloride (56 mg; 0.36 mmol) via Method AA to yield 47 mg. (66% yield). $^1$HNMR (400 MHz, DMSO-d$_6$) δ 7.34 (m, 2H), 7.26 (m, 2H), 7.12 (m, 3H), 6.77 (d, J=8.0 Hz, 1H), 6.54 (d, J=8.0 Hz, 1H), 5.94 (br s, 2H), 4.53 (br s, 1H), 4.03 (d, J=6.0 Hz, 2H), 3.63 (br s, 1H), 3.08 (br s, 1H), 2.82 (br s, 1H), 2.34 (s, 3H), 2.21 (m, 1H), 1.86 (br s, 1H), 1.75 (br s, 1H), 1.31 (m, 2H). MS m/z (ESI) 392 (M+H)$^+$.

Example-21

[4-(2,4-Diaminoquinazolin-5-yloxymethyl)piperidin-1-yl]-p-tolylmethanone (Example-021). The amidation of 5-(piperidin-4-ylmethoxy)quinazoline-2,4-diamine (50 mg; 0.18 mmol) was carried out using p-toluoyl chloride (57 mg; 0.37 mmol) via Method AA to yield 93 mg. (64% yield). $^1$HNMR (400 MHz, DMSO-d$_6$) δ 7.35 (t, J=8.0 Hz, 1H), 7.25 (m, 4H), 7.2 (br s, 2H), 6.77 (d, J=8.0 Hz, 1H), 6.54 (d, J=8.0 Hz, 1H), 5.94 (br s, 2H), 4.53 (br s, 1H), 4.03 (d, J=6.0 Hz, 2H), 3.67 (br s, 1H), 3.07 (br s, 1H), 2.844 (br s, 1H), 2.34 (s, 3H), 2.18 (m, 1H), 1.82 (m, 2H), 1.29 (m, 2H). MS m/z (ESI) 392 (M+H)$^+$.

Example-22

[4-(2,4-Diaminoquinazolin-5-yloxymethyl)piperidin-1-yl]-(2,4-difluorophenyl)methanone (Example-022). The amidation of 5-(piperidin-4-ylmethoxy)quinazoline-2,4-diamine (50 mg; 0.18 mmol) was carried out using 2,4-difluorobenzoyl chloride (65 mg; 0.37 mmol) via Method AA to yield 108 mg. (71% yield). $^1$HNMR (400 MHz, DMSO-d$_6$) δ 7.48 (m, 1H), 7.35 (m, 2H), 7.18 (m, 3H), 6.77 (d, J=8.0 Hz, 1H), 6.54 (d, J=8.0 Hz, 1H), 5.94 (br s, 2H), 4.53 (br d, J=13.2 Hz, 1H), 4.03 (d, J=6.0 Hz, 2H), 3.44 (m, 1H), 3.12 (t, J=12.8 Hz, 1H), 2.85 (m, 1H), 2.22 (m, 1H), 1.9 (d, J=12.4 Hz, 1H), 1.74 (d, J=12.4 Hz, 1H), 1.26 (m, 2H). MS m/z (ESI) 414 (M+H)$^+$.

Example-23

[4-(2,4-Diaminoquinazolin-5-yloxymethyl)piperidin-1-yl]-(3,4-difluorophenyl)methanone (Method AA) (Example-023). 5-(Piperidin-4-ylmethoxy)quinazoline-2,4-diamine (50 mg; 0.18 mmol) was shaken for 60 hours at room temperature in the presence of 3-(morpholino)propyl polystyrene sulfonamide (PS-NMM) (160 mg; 0.4 mmol) and 3,4-difluorobenzoyl chloride (65.3 mg; 0.37 mmol) in 4 mL N,N-dimethylformamide. Tris-(2-aminoethyl)aminomethyl polystyrene (PS-Trisamine) (112 mg; 0.4 mmol) was then added to the mixture and continued to shake for an additional 2 hours. Resins were filtered off and rinsed with methanol. Filtrate was concentrated at reduced pressure, and residue was triturated with 2 mL 1 N NaOH and ethanol (1:1). Solids were collected by filtration to yield [4-(2,4-diamino-quinazolin-5-yloxymethyl)-piperidin-1-yl]-(3,4-difluorophenyl)-methanone (117.4 mg; 76% yield). $^1$HNMR (400 MHz, DMSO-d$_6$) δ 7.51 (m, 2H), 7.35 (t, J=8.4 Hz, 1H), 7.26 (m, 3H), 6.77 (d, J=8.4 Hz, 1H), 6.54 (d, J=8.4 Hz, 1H), 5.94 (br s, 2H), 4.50 (br s, 1H), 4.03 (d, J=6.0 Hz, 2H), 3.60 (br s, 1H), 3.11 (br s, 1H), 2.82 (br s, 1H), 2.22 (s, 1H), 1.87 (br s, 1H), 1.75 (br s, 1H), 1.31 (m, 2H). MS m/z (ESI) 414 (M+H)$^+$.

Example-24

[4-(2,4-Diaminoquinazolin-5-yloxymethyl)piperidin-1-yl]-(2,3-difluorophenyl)methanone (Example-024). The amidation of 5-(piperidin-4-ylmethoxy)quinazoline-2,4-diamine (50 mg; 0.18 mmol) was carried out using 2,3-difluorobenzoyl chloride (65 mg; 0.37 mmol) via Method AA to yield 114 mg. (74% yield). $^1$HNMR (400 MHz, DMSO-d$_6$) δ 7.51 (q, J=8.8 Hz, 1H), 7.33 (m, 2H), 7.2 (m, 3H), 6.77 (d, J=8.4 Hz, 1H), 6.54 (d, J=8.0 Hz, 1H), 5.94 (br s, 2H), 4.54 (br d, J=12.8 Hz, 1H), 4.03 (d, J=6.0 Hz, 2H), 3.44 (d, J=14.0 Hz, 1H), 3.14 (t, J=12.4 Hz, 1H), 2.88 (m, 1H), 2.23 (s, 1H), 1.9 (d, J=12.4 Hz, 1H), 1.75 (d, J=10.8 Hz, 1H), 1.26 (m, 2H). MS m/z (ESI) 414 (M+H)$^+$.

Example-25

[5-(1-(2-Fluorobenzenesulfonyl)piperidin-4-ylmethoxy]quinazoline-2,4-diamine (Method CC) (Example-025). To a mixture of 5-(piperidin-4-ylmethoxy)quinazoline-2,4-diamine (250 mg; 0.9 mmol) and triethylamine (0.3 mL; 1.8 mmol) in 2.5 mL N,N-dimethylformamide was added 2-fluorobenzenesulfonyl chloride (196 mg; 1.0 mmol) and stirred at room temperature for 5 hours. Reaction was quenched with 1 mL 1N NaOH creating a homogenous mixture. After 1.5 hours, 1 mL of water was added to the newly formed precipitates and solids were collected by filtration. Solids were triturated with ethanol and rinsed once with diethyl ether to yield crude compound. (331 mg; 85% yield). 5-[1-(2-Fluorobenzenesulfonyl)piperidin-4-ylmethoxy]quinazoline-2,4-diamine (250 mg, 0.6 mmol) was purified by silica gel column (5% MeOH/CH$_2$Cl$_2$+1% NH$_4$OH). The fractions were reduced to 5 mL and diluted with 2 M HCl in Et$_2$O (5 mL). The solvents were completely removed under N$_2$ purge. The resulting semi-solid was triturated with absolute EtOH, and stored at 2° C. for 72 hours. The resulting solids are filtered and dried under vacuum at 30° C. overnight to yield 182 mg of 5-[1-(2-fluorobenzenesulfonyl)piperidin-4-ylmethoxy] quinazoline-2,4-diamine hydrochloride. $^1$HNMR (500 MHz, DMSO-d$_6$) δ 12.93 (s, 1H), 8.95 (s, 1H), 8.16 (s, 1H), 7.80 (t, J=7.5 Hz, 1H), 7.77 (dt, J=7.5, 2.5 Hz, 1H), 7.68 (t, J=8.5 Hz, 1H), 7.50 (t, J=8.5 Hz, 1H), 7.45 (t, J=7.5 Hz, 1H), 6.99 (d, J=8.5 Hz, 1H), 4.14 (d, J=6.5 Hz, 2H), 3.74 (br d, J=12.0 Hz, 2H), 2.54 (m, 2H), 2.07 (m, 1H), 1.84 (br d, J=12 Hz, 2H), 1.33. (m. 2H). $^{12}$CNMR (500 MHz, DMSO-d$_6$) δ 162.3, 159.2, 157.2, 156.8, 154.2, 141.0, 136.2, 135.8, 130.8, 125.1, 124.2, 117.6, 117.5, 108.6, 106.8, 99.6, 73.1, 45.1, 33.4, 27.8. MS m/z (ESI) 432 (M+H)$^+$.

Example-26

5-[4-(3-Chlorobenzenesulfonyl)piperidin-4-ylmethoxy] quinazoline-2,4-diamine (Example-026). The sulfonamide was obtained by reacting 5-(piperidin-4-ylmethoxy)quinazoline-2,4-diamine (50 mg; 0.18 mmol) and 3-chlorobenzenesulfonyl chloride (78 mg; 0.37 mmol) via Method AA to yield 80 mg. (99% yield). $^1$HNMR (400 MHz, DMSO-d$_6$) δ 7.82 (m, 1H), 7.72 (m, 3H), 7.32 (t, J=8.4 Hz, 1H), 7.11 (br s, 2H), 6.75 (d, J=8.0 Hz, 1H), 6.50 (d, J=7.6 Hz, 1H), 5.93 (br s, 2H), 3.96 (d, J=6.4 Hz, 2H), 3.72 (br d, J=11.6 Hz, 2H), 2.32 (t, J=12 Hz, 2H), 1.84 (m, 3H), 1.36 (m, 2H). MS m/z (ESI) 448 (M+H)$^+$.

Example-27

5-[4-(2-Chlorobenzenesulfonyl)piperidin-4-ylmethoxy] quinazoline-2,4-diamine (Example-027). The sulfonamide was obtained by reacting 5-(piperidin-4-ylmethoxy)quinazoline-2,4-diamine (50 mg; 0.18 mmol) and 2-chlorobenzenesulfonyl chloride (78 mg; 0.37 mmol) via Method AA to yield 80 mg. (99% yield). $^1$HNMR (400 MHz, DMSO-d$_6$) δ 7.97 (dd, J=7.6, 1.2 Hz, 1H), 7.69 (m, 2H), 7.57 (m, 1H), 7.33 (t, J=8.4 Hz, 1H), 7.12 (br s, 2H), 6.76 (d, J=8.0 Hz, 1H), 6.52 (d, J=7.6 Hz, 1H), 5.93 (br s, 2H), 3.99 (d, J=6.0 Hz, 2H), 3.77 (br d, J=12.0 Hz, 2H), 2.75 (t, J=10.8 Hz, 2H), 2.06 (s, 1H), 1.84 (d, J=10.8 Hz, 2H), 1.31 (m, 2H). MS m/z (ESI) 448 (M+H)$^+$.

Example-28

[5-(1-(4-Chlorobenzenesulfonyl)piperidin-4-ylmethoxy] quinazoline-2,4-diamine (Example-028). The sulfonamide was obtained by reacting 5-(piperidin-4-ylmethoxy)quinazoline-2,4-diamine (50 mg; 0.18 mmol) and 4-chlorobenzenesulfonyl chloride (76 mg; 0.36 mmol) via Method AA to yield 49 mg. (61% yield). $^1$HNMR (400 MHz, DMSO-d$_6$) δ 7.74 (m, 4H), 7.32 (t, J=8.4 Hz, 1H), 7.12 (br s, 2H), 6.75 (d, J=7.6 Hz, 1H), 6.49 (d, J=7.6 Hz, 1H), 5.93 (br s, 2H), 3.97 (d, J=6.4 Hz, 2H), 3.68 (br d, J=11.2 Hz, 2H), 2.29 (t, J=12.0 Hz, 2H), 1.93 (m, 1H), 1.83 (d, J=12.8 Hz, 2H), 1.36 (m, 2H). MS m/z (ESI) 448 (M+H)$^+$.

Example-29

[5-(1-(Naphthalene-1-sulfonyl)piperidin-4-ylmethoxy] quinazoline-2,4-diamine (Example-029). The sulfonamide was obtained by reacting 5-(piperidin-4-ylmethoxy)quinazoline-2,4-diamine (50 mg; 0.18 mmol) and 1-naphthylsulfonyl chloride (82 mg; 0.36 mmol) via Method AA to yield 47 mg. (56% yield). (MS+2H) $^1$HNMR (400 MHz, DMSO-d$_6$) δ 8.69 (d, J=8.8 Hz, 1H), 8.28 (d, J=8.4 Hz, 1H), 8.12 (m, 2H), 7.72 (m, 3H), 7.31 (t, J=8.4 Hz, 1H), 7.08 (br, s, 2H), 6.74 (d, J=8.4 Hz, 1H), 6.48 (d, J=8.4 Hz, 1H), 5.94 (br s, 2H), 3.93 (d, J=6.0 Hz, 2H), 3.81 (br d, J=12 Hz, 2H), 2.54 (m, 2H), 1.95 (m, 1H), 1.81 (d, J=12 Hz, 2H), 1.3 (m, 2H). MS m/z (ESI) 464 (M+H)$^+$.

Example-30

[5-(1-(Naphthalene-2-sulfonyl)piperidin-4-ylmethoxy] quinazoline-2,4-diamine (Example-030). The sulfonamide was obtained by reacting 5-(piperidin-4-ylmethoxy)quinazoline-2,4-diamine (50 mg; 0.18 mmol) and 2-naphthylsulfonyl chloride (82 mg; 0.36 mmol) via Method AA to yield 68 mg. (82% yield). $^1$HNMR (400 MHz, DMSO-d$_6$) δ 8.45 (br s, 1H), 8.19 (m, 2H), 8.08 (d, J=8.0 Hz, 1H), 7.74 (m, 3H), 7.31 (t, J=8.4 Hz, 1H), 7.08 (br s, 2H), 6.74 (d, J=8.4 Hz, 1H), 6.47 (d, J=7.6 Hz, 1H), 5.92 (br s, 2H), 3.94 (d, J=6.0 Hz, 2H), 3.78 (br d, J=11.6 Hz, 2H), 2.31 (t, J=11.6 Hz, 2H), 1.83 (m, 3H), 1.38 (m, 2H). MS m/z (ESI) 464 (M+H)$^+$.

Example-31

[5-(1-(Toluene-2-sulfonyl)piperidin-4-ylmethoxy] quinazoline-2,4-diamine (Example-031). The sulfonamide was obtained by reacting 5-(piperidin-4-ylmethoxy)quinazoline-2,4-diamine (50 mg; 0.18 mmol) and o-toluenesulfonyl chloride (53 mg; 0.36 mmol) via Method AA to yield 77 mg. (69% yield). $^1$HNMR (400 MHz, DMSO-d$_6$) δ 7.79 (d, J=8.0 Hz, 1H), 7.57 (m, 1H), 7.43 (m, 2H), 7.33 (t, J=8.4 Hz, 1H), 7.12 (br s, 2H), 6.76 (d, J=8.0 Hz, 1H), 6.51 (d, J=8.4 Hz, 1H), 5.93 (br s, 2H), 3.99 (d, J=6.4 Hz, 2H), 3.67 (br d, J=12.4 Hz, 2H), 2.61 (m, 2H), 2.58 (s, 3H), 2.0 (m, 1H), 1.83 (d, J=12.4 Hz, 2H), 1.32 (m, 2H). MS m/z (ESI) 428 (M+H)$^+$.

Example-32

5-[1-(Toluene-3-sulfonyl)piperidin-4-ylmethoxy] quinazoline-2,4-diamine (Example-032). The sulfonamide was obtained by reacting 5-(piperidin-4-ylmethoxy)quinazoline-2,4-diamine (50 mg; 0.18 mmol) and m-toluenesulfonyl chloride (71 mg; 0.37 mmol) via Method AA to yield 131 mg. (83% yield). $^1$HNMR (400 MHz, DMSO-d$_6$) δ 7.54 (m, 4H), 7.47 (t, J=8.4 Hz, 1H), 7.10 (br s, 2H), 6.75 (d, J=8.4 Hz, 1H), 6.49 (d, J=8.0 Hz, 1H), 5.93 (br s, 2H), 3.95 (d, J=6.0 Hz, 2H), 3.69 (br d, J=11.6 Hz, 2H), 2.42 (s, 3H), 2.23 (t, J=12.0 Hz, 2H), 1.86 (m, 3H), 1.36 (m, 2H). MS m/z (ESI) 428 (M+H)$^+$.

Example-33

[5-(1-(Toluene-4-sulfonyl)piperidin-4-ylmethoxy] quinazoline-2,4-diamine (Example-033). The sulfonamide was obtained by reacting 5-(piperidin-4-ylmethoxy)quinazoline-2,4-diamine (50 mg; 0.18 mmol) and p-toluenesulfonyl chloride (69 mg; 0.36 mmol) via Method AA to yield 77 mg.

(99% yield). $^1$HNMR (400 MHz, DMSO-d$_6$) δ 12.1 (br s, 1H), 8.92 (br s, 1H), 8.15 (br s, 1H), 7.56 (m, 4H), 7.47 (m, 4H), 7.11 (dd, J=8.4, 0.4 Hz, 1H), 6.97 (d, J=8.4 Hz, 1H), 4.11 (d, J=6.4 Hz, 2H), 3.66 (br d, J=11.6 Hz, 2H), 2.28 (s, 3H), 2.19 (t, J=9.6 Hz, 1H), 1.96 (m, 1H), 1.80 (br d, J=11.2 Hz, 1H), 1.33 (m, 2H). MS m/z (ESI) 428 (M+H)$^+$ Example-34

5-[4-(2,4-Difluorobenzenesulfonyl)-piperidin-4-yl-methoxy]quinazoline-2,4-diamine (Example-034). The sulfonamide was obtained by reacting 5-(piperidin-4-yl-methoxy)quinazoline-2,4-diamine (50 mg; 0.18 mmol) and 2,4-difluorobenzenesulfonyl chloride (79 mg; 0.37 mmol) via Method AA to yield 80 mg. (99% yield). $^1$HNMR (400 MHz, DMSO-d$_6$) δ 7.86 (m, 1H), 7.61 (m, 1H), 7.33 (m, 2H), 7.12 (br s, 2H), 6.75 (d, J=8.0 Hz, 1H), 6.51 (d, J=7.6 Hz, 1H), 5.93 (br s, 2H), 3.97 (d, J=6.0 Hz, 2H), 3.71 (br d, J=12.0 Hz, 2H), 2.56 (t, J=12 Hz, 2H), 2.0 (s, 1H), 1.85 (d, J=10.4 Hz, 2H), 1.34 (m, 2H). MS m/z (ESI) 451 (M+H)$^+$.

Example-35

5-[4-(3,4-Difluorobenzenesulfonyl)-piperidin-4-yl-methoxy]quinazoline-2,4-diamine (Example-035). The sulfonamide was obtained by reacting 5-(piperidin-4-yl-methoxy)quinazoline-2,4-diamine (50 mg; 0.18 mmol) and 3,4-difluorobenzenesulfonyl chloride (79 mg; 0.37 mmol) via Method AA to yield 80 mg. (99% yield). $^1$HNMR (400 MHz, DMSO-d$_6$) δ 7.88 (m, 1H), 7.73 (m, 1H), 7.65 (m, 1H), 7.33 (t, J=8.0 Hz, 1H), 7.11 (br s, 2H), 6.75 (dd, J=8.0, 0.4 Hz, 1H), 6.50 (d, J=7.6 Hz, 1H), 5.93 (br s, 2H), 3.97 (d, J=6.0 Hz, 2H), 3.69 (br d, J=11.6 Hz, 2H), 2.34 (m, 2H), 1.87 (m, 3H), 1.36 (m, 2H). MS m/z (ESI) 450 (M+H)$^+$.

Example-36

$^1$HNMR (400 MHz, DMSO-d$_6$) δ 7.34 (t, J=8.0 Hz, 1H), 7.2 (s, 2H), 6.77 (d, J=8.0 Hz, 1H), 6.54 (d, J=7.6 Hz, 1H), 5.94 (s, 2H), 3.96 (d, J=6.4 Hz, 2H), 2.93-2.98 (m, 3H), 2.43-2.51 (m, 2H), 1.94 (br s, 1H), 1.66-1.72 (m, 2H), 1.16-1.22 (m, 2H). MS m/z (ESI) 275 (M+H)$^+$.

Example-37

$^1$HNMR (400 MHz, DMSO-d$_6$) δ 7.34 (t, J=8.0 Hz, 1H), 7.17 (s, 2H), 6.77 (dd, J=8.4, 0.8 Hz, 1H), 6.54 (d, J=8.0 Hz, 1H), 5.94 (s, 2H), 3.96-4.02 (m, 4H), 2.71-2.86 (m, 2H), 2.03-2.12 (m, 1H), 1.71-1.8 (m, 2H), 1.11-1.27 (m, 2H). MS m/z (ESI) 375 (M+H)$^+$.

Example-38

$^1$HNMR (400 MHz, DMSO-d$_6$) δ 7.55 (m, 2H), 7.32 (m, 2H), 7.65 (br s, 2H), 6.76 (dd, J=8.0, 0.4 Hz, 1H), 6.52 (d, J=7.6 Hz, 1H), 5.94 (br s, 2H), 3.99 (d, J=6.0 Hz, 2H), 3.48 (s, 2H), 2.82 (m, 2H), 1.90 (m, 3H), 1.34 (m, 2H). MS m/z (ESI) 433 (M+H)$^+$.

Example-39

$^1$HNMR (400 MHz, DMSO-d$_6$) δ 7.8-7.84 (m, 1H), 7.74 (s, 1H), 7.32-7.43 (m, 2H), 7.25 (t, J=7.6 Hz, 1H), 7.2 (br s, 2H), 6.78 (dd, J=8.0, 0.8 Hz, 1H), 6.56 (d, J=8.0 Hz, 1H), 5.99 (s, 2H), 4.42-4.58 (m, 1H), 4.04 (d, J=6.4 Hz, 2H), 3.52-3.61 (m, 1H), 3.03-3.19 (m, 1H), 2.74-2.9 (m, 1H), 2.15-2.28 (m, 1H), 1.7-1.93 (m, 2H), 1.21-1.41 (m, 2H). MS m/z (ESI) 505 (M+H)$^+$.

Example-40

$^1$HNMR (400 MHz, DMSO-d$_6$) δ7.81 (dd, J=6.4, 2.0 Hz, 2H), 7.35 (t, J=8.4 MHz, 1H), 7.18 (m, 4H), 6.77 (dd, J=8.0, 0.4 Hz, 1H), 6.54 (d, J=7.6 Hz, 1H), 5.94 (br s, 1H), 4.03 (d, J=6.4 Hz, 2H), 3.59 (br s, 1H), 3.09 (br s, 1H), 2.83 (br s, 1H), 2.20 (m, 1H), 1.74 (m, 2H), 1.29 (m, 2H). MS m/z (ESI) 504 (M+H)$^+$.

Example-41

$^1$HNMR (400 MHz, DMSO-d$_6$) δ 7.88 (m, 1H), 7.46 (m, 1H), 7.31 (m, 2H), 7.17 (m, 3H), 6.77 (d, J=8.4 Hz, 1H), 6.55 (t, J=7.2 Hz, 1H), 5.94 (m, 2H), 4.59 (t, J=14 Hz, 1H), 4.04 (t, J=6.0 Hz, 2H), 3.23 (m, 1H), 3.06 (m, 1H), 2.8 (m, 1H), 2.20 (m, 1H), 1.39 (m, 2H). MS m/z (ESI) 504 (M+H)$^+$.

Example-42

$^1$HNMR (400 MHz, DMS O-d$_6$) δ 7.84 (dd, J=8.0, 1.2 Hz, 1H), 7.38 (m, 3H), 7.20 (br s, 2H), 7.02 (m, 1H), 6.76 (dd, J=8.0, 0.4 Hz, 1H), 6.53 (dd, J=8.0, 0.8 Hz, 1H), 5.94 (br s, 2H), 4.0 (m, 2H), 3.47 (s, 2H), 2.86 (m, 2H), 2.09 (m, 2H), 1.91 (m, 1H), 1.75 (m, 2H), 1.37 (m, 1H). MS m/z (ESI) 490 (M+H)$^+$.

Example-43

$^1$HNMR (400 NM, DMSO-d$_6$) δ 7.67 (s, 1H), 7.6 (m, 1H), 7.32 (m, 2H), 7.19 (br s, 2H), 7.13 (t, J=7.6 Hz, 1H), 6.76 (dd, J=8.0, 0.4 Hz, 1H), 6.54 (dd, J=8.4, 0.8 Hz, 1H), 5.94 (br s, 2H), 3.98 (d, J=6.4 Hz, 2H), 3.44 (s, 2H), 2.82 (m, 2H), 1.98 (m, 2H), 1.86 (m, 1H), 1.73 (m, 2H), 1.36 (m, 1H). MS m/z (ESI) 490 (M+H)$^+$.

Example-44

$^1$HNMR (400 MHz, DMSO-d$_6$) δ 7.66 (m, 2H), 7.34 (t, J=8.0 Hz, 1H), 7.19 (br s, 2H), 7.11 (d, J=8.4 Hz, 1H), 6.76 (dd, J=8.0, 0.4 Hz, 1H), 6.54 (dd, J=8.4, 0.8 Hz, 1H), 5.94 (br s, 2H), 3.98 (d, J=6.4 Hz, 2H), 3.42 (s, 2H), 2.81 (m, 2H), 1.96 (m, 2H), 1.87 (m, 1H), 1.73 (m, 2H), 1.33 (m, 2H). MS m/z (ESI) 490 (M+H)$^+$.

Example-45

$^1$HNMR (400 MHz, DMSO-d$_6$) δ 7.35 (t, J=8.0 Hz, 1H), 7.12-7.28 (m, 3H), 6.84-6.89 (m, 2H), 6.78 (d, J=8.4 Hz, 1H), 6.55 (d, J=8.0 Hz, 1H), 6.02 (s, 2H), 4.4-4.48 (m, 1H), 3.84-4.06 (m, 3H), 3.72 (s, 3H), 3.64 (s, 2H), 2.97-3.05 (m, 1H), 2.56-2.64 (m, 1H), 2.06-2.19 (m, 1H), 1.68-1.81 (m, 2H), 1.0-1.18 (m, 2H). MS m/z (ESI) 423 (M+H)$^+$.

Example-46

$^1$HNMR (400 MHz, DMSO-d$_6$) δ 7.46-7.53 (m, 1H), 7.16-7.39 (m, 6H), 6.78 (dd, J=8.6, 0.8 Hz, 1H), 6.57 (d, J=8.0 Hz, 1H), 5.99 (s, 2H), 4.45-4.58 (m, 1H), 4.04 (d, J=6.4 Hz, 2H), 3.52-3.62 (m, 1H), 3.02-3.19 (m, 1H), 2.76-2.9 (m, 1H), 2.16-2.29 (m, 1H), 1.7-1.94 (m, 2H), 1.22-1.41 (m, 2H). MS m/z (ESI) 397 (M+H)$^+$.

Example-47

$^1$HNMR (400 MHz, DMSO-d$_6$) δ7.88 (d, J=8.4 Hz, 1H), 7.58 (d, J=8.4 Hz, 1H), 7.34 (t, J=8.4 Hz, 1H), 7.2 (s, 2H), 6.77 (d, J=8.0 Hz, 1H), 6.54 (d, J=8.0 Hz, 1H), 5.94 (s, 2H), 4.0 (d, J=6.0 Hz, 2H), 3.59 (s, 2H), 3.2 (s, 3H), 2.8-2.89 (m, 2H), 1.96-2.08 (m, 2H), 1.8-1.95 (m, 1H), 1.71-1.8 (m, 2H), 1.31-1.42 (m, 2H). MS m/z (ESI) 443 (M+H)$^+$.

Example-48

$^1$HNMR (400 MHz, DMSO-d$_6$) δ 7.36 (t, J=8.0 Hz, 1H), 7.25 (br s, 2H), 6.79 (dd, J=8.4, 0.8 Hz, 1H), 6.56 (d, J=8.0 Hz, 1H), 6.00 (s, 2H), 4.33 (d, J=13.6 Hz, 2H), 4.02 (d, J=6.4 Hz, 2H), 2.76-2.9 (m, 2H), 2.12-2.24 (m, 1H), 1.76-1.85 (m, 2H), 1.12-1.28 (m, 2H). MS m/z (ESI) 359 (M+H)$^+$.

Example-49

$^1$HNMR (400 MHz, DMSO-d$_6$) δ 7.36 (t, J=8.0 Hz, 1H), 7.19 (s, 2H), 6.77 (d, J=8.0 Hz, 1H), 6.54 (d, J=8.0 Hz, 1H), 5.93 (s, 2H), 4.4-4.51 (m, 1H), 3.91-4.06 (m, 3H), 0.9-3.1 (m, 20H). MS m/z (ESI) 398 (M+H)$^+$.

Example-50

$^1$HNMR (400 MHz, DMSO-d$_6$) δ7.88 (d, J=8.4 Hz, 1H), 7.58 (d, J=8.4 Hz, 1H), 7.34 (t, J=8.4 Hz, 1H), 7.2 (s, 2H), 6.77 (d, J=8.0 Hz, 1H), 6.54 (d, J=8.0 Hz, 1H), 5.94 (s, 2H), 4.0 (d, J=6.0 Hz, 2H), 3.59 (s, 2H), 3.2 (s, 3H), 2.8-2.89 (m, 2H), 1.96-2.08 (m, 2H), 1.8-1.95 (m, 1H), 1.71-1.8 (m, 2H), 1.31-1.42 (m, 2H). MS m/z (ESI) 443 (M+H)$^+$.

Example-51

$^1$HNMR (400 MHz, DMSO-d$_6$) δ 8.47 (d, J=2.4 Hz, 1H), 7.91 (dd, J=8.0, 2.4 Hz, 1H), 7.61 (d, J=8.0 Hz, 1H), 7.36 (t, J=8.0 Hz, 1H), 7.21 (s, 2H), 6.78 (d, J=8.0 Hz, 1H), 6.56 (d, J=8.0 Hz, 1H), 5.97 (s, 2H), 4.46-4.58 (m, 1H), 4.04 (d, J=6.4 Hz, 2H), 3.53-3.62 (m, 1H), 3.11-3.22 (m, 1H), 2.8-2.91 (m, 1H), 2.18-2.29 (m, 1H), 1.7-1.95 (m, 2H), 1.26-1.42 (m, 2H). MS m/z (ESI) 414 (M+H)$^+$.

Example-52

$^1$HNMR (400 MHz, DMSO-d$_6$) δ 7.3-7.39 (m, 4H), 7.17 (s, 2H), 6.78 (d, J=8.0 Hz, 1H), 6.56 (d, J=8.0 Hz, 1H), 5.95 (s, 2H), 4.5-4.59 (m, 1H), 4.04 (d, J=6.0 Hz, 2H), 3.41-3.49 (m, 1H), 3.09-3.18 (m, 1H), 2.82-2.91 (m, 1H), 2.18-2.29 (m, 1H), 1.7-1.94 (m, 2H), 1.2-1.38 (m, 2H). MS m/z (ESI) 415 (M+H)$^+$.

Example-53

$^1$HNMR (400 MHz, DMSO-d$_6$) δ 7.35 (t, J=8.0 Hz, 1H), 7.19 (s, 2H), 6.78 (d, J=8.0 Hz, 1H), 6.55 (d, J=8.0 Hz, 1H), 5.96 (s, 2H), 4.39-4.48 (m, 1H), 4.01 (d, J=6.4 Hz, 2H), 3.88-3.96 (m, 1H), 2.97-3.08 (m, 1H), 2.45-2.6 (m, 1H), 2.08-2.34 (m, 4H), 1.9-1.96 (m, 1H), 1.72-1.85 (m, 3H), 0.98-1.51 (m, 10H). MS m/z (ESI) 411 (M+H)$^+$.

Example-54

$^1$HNMR (400 MHz, DMSO-d$_6$) δ 7.7-7.21 (m, 1H), 7.44-7.81 (m, 2H), 7.39 (t, J=8.0 Hz, 1H), 7.22-7.38 (br s, 2H), 6.8 (d, J=8.0 Hz, 1H), 6.6 (d, J=8.0 Hz, 1H), 6.12 (s, 2H), 4.44-4.48 (m, 1H), 4.05 (d, J=6.4 Hz, 2H), 3.46-3.58 (m, 1H), 3.08-3.18 (m, 1H), 2.78-2.9 (m, 1H), 2.16-2.29 (m, 1H), 1.7-1.94 (m, 2H), 1.25-1.4 (m, 2H). MS m/z (ESI) 447 (M+H)$^+$

Example-55

$^1$HNMR (400 MHz, DMSO-d$_6$) δ 8.84 (m, 1H), 8.13 (br s, 1H), 7.74 (m, 2H), 7.68 (m, 2H), 7.38 (dd, J=3.6, 0.8 Hz, 1H), 7.15 (m, 1H), 6.99 (m, 2H), 4.2 (d, J=6.4 Hz, 2H), 3.27 (m, 2H), 3.05 (m, 2H), 2.30 (m, 1H), 1.83 (m, 2H), 1.30 (m, 2H). MS m/z (ESI) 384 (M+H)$^+$.

Example-56

$^1$HNMR (400 MHz, DMSO-d$_6$) δ 8.89 (br s, 1H), 8.15 (m, 1H), 7.88 (m, 2H), 7.68 (m, 2H), 7.35 (m, 1H), 6.98 (m, 4H), 4.18 (d, J=6.4 Hz, 2H), 3.83 (s, 3H), 3.27 (m, 4H), 2.84 (m, 1H), 2.27 (m, 1H), 1.90 (m, 1H), 1.77 (m, 1H), 1.27 (m, 1H). MS m/z (ESI) 409 (M+H)$^+$.

Example-57

$^1$HNMR (400 MHz, DMSO-d$_6$) δ 8.78 (br s, 1H), 8.11 (br s, 1H), 7.83 (m, 1H), 7.67 (m, 3H), 7.15 (d, J=3.2 Hz, 1H), 6.98 (m, 2H), 6.62 (m, 1H), 4.35 (m, 2H), 4.17 (d, J=6.8 Hz, 2H), 3.3 (m, 3H), 2.30 (m, 1H), 1.84 (m, 2H), 1.31 (m, 2H). MS m/z (ESI) 368 (M+H)$^+$.

Example-58

$^1$HNMR (400 MHz, DMSO-d$_6$) δ 8.87 (m, 1H), 8.69 (m, 1H), 8.15 (m, 2H), 7.99 (m, 4H), 7.60 (m, 4H), 6.69 (m, 2H), 4.73 (m, 1H), 4.17 (m, 2H), 3.28 (m, 2H), 2.27 (m, 2H), 1.91 (m, 2H), 1.52 (m, 2H). MS m/z (ESI) 428 (M+H)$^+$.

Example-59

$^1$HNMR (400 M , DMSO-d$_6$) δ 8.97 (s, 1H), 8.21 (m, 1H), 7.88 (m, 2H), 7.70 (t, J=8.0 Hz, 1H), 7.02 (t, J=8.4 Hz, 1H), 6.56 (s, 4H), 6.44 (s, 2H), 4.49 (d, J=12.4 Hz, 1H), 4.19 (d, J=6.8 Hz, 2H), 3.94 (d, J=14 Hz, 1H), 3.16 (m, 1H), 2.87 (m, 1H), 2.30 (m, 1H), 1.81 (m, 2H), 1.26 (m, 2H). MS m/z (ESI) 383 (M+H)$^+$.

Example-60

$^1$HNMR (400 MHz, DMSO-d$_6$) δ 8.73 (br s, 1H), 8.04 (m, 2H), 7.86 (br s, 2H), 7.73 (m, 3H), 7.48 (m, 2H), 6.98 (m, 2H), 6.96 (m, 2H), 4.53 (m, 1H), 4.17 (t, J=6.8 Hz, 2H), 3.22 (m, 3H), 2.27 (m, 1H), 1.89 (m, 1H), 1.71 (m, 1H), 1.31 (m, 2H). MS m/z (ESI) 447 (M+H)$^+$.

Example-61

$^1$HNMR (400 MHz, DMSO-d$_6$) δ 8.65 (s, 1H), 8.00 (m, 3H), 7.89 (m, 2H), 7.79 (br s, 3H), 7.62 (m, 3H), 7.46 (m, 6H), 6.97 (m, 3H), 4.55 (d, J=13.2 Hz, 1H), 4.15 (m, 2H), 3.28 (m, 2H), 3.07 (m, 1H), 2.27 (m, 1H), 1.89 (m, 1H), 1.69 (m, 1H), 1.19 (m, 2H). MS m/z (ESI) 462 (M+H)$^+$.

Example-62

$^1$HNMR (400 MHz, DMSO-d$_6$) δ 8.70 (s, 1H), 8.00 (m, 2H), 7.63 (m, 4H), 7.28 (m, 3H), 6.97 (m, 1H), 4.51 (br s, 1H), 4.16 (d, J=6.4 Hz, 2H), 3.28 (m, 2H), 2.27 (m, 1H), 1.81 (m, 3H), 1.28 (m, 2H). MS m/z (ESI) 396 (M+H)$^+$.

Example-63

$^1$HNMR (400 MHz, DMSO-d$_6$) δ 8.63 (s, 1H), 8.06 (m, 2H), 7.55 (m, 6H), 6.95 (m, 2H), 4.51 (br s, 1H), 4.16 (d, J=6.4

Hz, 2H), 3.28 (m, 2H), 2.28 (m, 1H), 1.81 (m, 3H), 1.32 (m, 2H). MS m/z (ESI) 462 (M+H)⁺.

Example-64

¹HNMR (400 MHz, DMSO-d₆) δ 8.75 (s, 1H), 8.07 (s, 1H), 7.85 (d, J=8.0 Hz, 2H), 7.64 (m, 3H), 7.29 (m, 2H), 6.97 (m, 2H), 4.17 (d, J=6.4 Hz, 2H), 3.27 (m, 2H), 2.65 (m, 4H), 2.27 (m, 1H), 1.81 (m, 2H), 1.25 (m, 5H). MS m/z (ESI) 406 (M+H)⁺.

Example-65

¹HNMR (400 MHz, DMSO-d₆) δ 8.67 (s, 1H), 7.97 (m, 2H), 7.82 (m, 2H), 7.62 (m, 2H), 7.44 (m, 2H), 6.96 (m, 2H), 4.50 (m, 1H), 4.16 (d, J=6.4 Hz, 2H), 3.53 (m, 1H), 3.29 (m, 2H), 2.28 (m, 1H), 1.88 (m, 1H), 1.73 (m, 1H), 1.25 (m, 2H). MS m/z (ESI) 462 (M+H)⁺.

Example-66

¹HNMR (400 MHz, DMSO-d₆) δ 8.86 (br s, 1H), 8.12 (m, 1H), 7.66 (m, 3H), 6.98 (m, 2H), 4.34 (m, 1H), 4.17 (d, J=6.8 Hz, 2H), 3.71 (m, 1H), 3.31 (m, 3H), 2.95 (m, 2H), 2.52 (m, 1H), 2.14 (m, 4H), 1.77 (m, 2H), 1.35 (m, 2H). MS m/z (ESI) 356 (M+H)⁺.

Example-67

¹HNMR (400 MHz, DMSO-d₆) δ 8.67 (s, 1H), 8.03 (m, 1H), 7.64 (t, J=8.4 Hz, 1H), 7.45 (br s, 2H), 6.95 (m, 2H), 4.50 (m, 1H), 4.14 (m, 3H), 3.53 (m, 1H), 3.27 (m, 2H), 2.24 (m, 1H), 1.80 (m, 2H), 1.41 (m, 6H), 0.80 (m, 6H). MS m/z (ESI) 372 (M+H)⁺.

Example-68

¹HNMR (400 MHz, DMSO-d₆) δ 8.58 (s, 1H), 7.96 (m, 1H), 7.62 (t, J=8.4 Hz, 1H), 7.36 (m, 2H), 6.93 (m, 2H), 4.46 (m, 1H), 4.13 (m, 2H), 4.01 (m, 1H), 3.27 (m, 2H), 3.05 (m, 1H), 1.59 (m, 2H), 1.84 (m, 2H), 1.55 (m, 2H), 1.38 (m, 1H), 1.05 (m, 3H), 0.80 (m, 3H). MS m/z (ESI) 358 (M+H)⁺.

Example-69

¹HNMR (400 MHz, DMSO-d₆) δ 8.91 (s, 1H), 8.16 (s, 1H), 7.68 (m, 2H), 6.99 (m, 2H), 4.42 (m, 1H), 4.15 (m, 2H), 4.01 (m, 1H), 3.03 (m, 2H), 2.22 (m, 1H), 1.70 (m, 1H), 1.16 (m, 2H). MS m/z (ESI) 370 (M+H)⁺.

Example-70

¹HNMR (400 MHz, DMSO-d₆) δ 8.62 (br s, 1H), 8.01 (m, 1H), 7.95 (s, 1H), 762 (m, 1H), 7.49 (m, 1H), 7.38 (m, 2H), 7.32 (m, 4H), 7.18 (m, 1H), 6.93 (m, 2H), 4.36 (m, 1H), 4.15 (m, 2H), 3.98 (m, 2H), 3.77 (s, 2H), 3.31 (m,), 3.09 (m, 1H), 2.23 (m, 1H), 1.88 (m, 2H), 1.29 (m, 1H), 1.12 (m, 1H). MS m/z (ESI) 424 (M+H)⁺.

Example-71

¹HNMR (400 MHz, DMSO-d₆) δ 9.21 (s, 2H), 8.88 (m, 2H), 8.53 (m, 2H), 8.13 (m, 2H), 8.01 (m, 3H), 7.71 (d, J=8.0 Hz, 1H), 7.02 (m, 2H), 4.54 (m, 1H), 4.19 (m, 2H), 3.53 (m, 1H), 3.29 (m, 2H), 2.90 (m, 2H), 2.03 (m, 1H), 1.89 (m, 1H), 1.35 (m, 1H). MS m/z (ESI) 447 (M+H)⁺.

Example-72

¹HNMR (400 MHz, DMSO-d₆) δ 8.13 (br s, 1H), 7.69 (br s, 1H), 7.53 (t, J=8.0 Hz, 1H), 6.86 (m, 4H), 4.12 (d, J=6.4 Hz, 2H), 3.59 (br d, J=11.6 Hz, 2H), 2.74 (m, 2H), 2.06 (m, 1H), 1.86 (m, 2H), 1.36 (m, 2H). MS m/z (ESI) 352 (M+H)⁺.

Example-73

¹HNMR (400 MHz, DMSO-d₆) δ 12.2 (s, 1H), 8.92 (s, 1H), 8.3 (m, 2H), 7.67 (m, 1H), 7.52 (m, 2H), 7.33 (m, 2H), 6.97 (m, 2H), 4.10 (m, 2H), 3.68 (m, 2H), 2.21 (m, 2H), 1.81 (m, 3H), 1.36 (m, 2H). MS m/z (ESI) 470 (M+H)⁺.

Example-74

¹HNMR (400 MHz, DMSO-d₆) δ 12.6 (s, 1H), 8.94 (s, 1H), 8.16 (m, 1H), 7.68 (m, 1H), 7.56 (m, 1H), 7.38 (m, 1H), 6.99 (m, 3H), 4.15 (d, J=6.4 Hz, 1H), 3.65 (br d, J=11.6 Hz, 2H), 2.44 (m, 2H), 2.06 (m, 1H), 1.85 (m, 2H), 1.38 (m, 2H). MS m/z (ESI) 454 (M+H)⁺.

Example-75

¹HNMR (400 MHz, DMSO-d₆) δ 12.5 (br s, 1H), 8.93 (br s, 1H), 8.16 (br s, 1H), 8.05 (dd, J=5.2, 1.26 Hz, 1H), 7.95 (br s, 1H), 7.65 (m, 3H), 7.29 (m, 1H), 6.98 (m, 2H), 4.13 (d, J=6.4 Hz, 2H), 3.67 (br d, J=11.6 Hz, 2H), 2.34 (m, 2H), 1.88 (m, 3H), 1.37 (m, 2H). MS m/z (ESI) 420 (M+H)⁺.

Example-76

¹HNMR (400 MHz, DMSO-d₆) δ 12.4 (br s, 1H), 8.98 (br s, 1H), 8.19 (s, 1H), 7.69 (m, 2H), 7.0 (m, 2H), 4.18 (d, J=6.4 Hz, 2H), 3.66 (br d, J=11.6 Hz, 2H), 2.50 (m, 2H), 2.43 (s, 3H), 2.23 (s, 3H), 1.85 (m, 3H), 1.34 (m, 2H). MS m/z (ESI) 433 (M+H)⁺.

Example-77

¹HNMR (400 MHz, DMSO-d₆) δ 12.6 (br s, 1H), 8.93 (br s, 1H), 8.15 (br s, 1H), 7.58 (m, 5H), 7.41 (m, 1H), 6.99 (m, 2H), 4.12 (d, J=6.4 Hz, 2H), 3.70 (br d, J=11.6 Hz, 2H), 2.31 (m, 2H), 2.0 (s, 1H), 1.81 (m, 2H), 1.34 (m, 2H). MS m/z (ESI) 432 (M+H)⁺.

Example-78

¹HNMR (400 M , DMSO-d₆) δ 12.1 (br s, 1H), 8.94 (br s, 1H), 8.20 (br s, 1H), 7.97 (m, 3H), 7.67 (m, 2H), 7.59 (m, 2H), 7.30 (t, J=7.6 Hz, 1H), 7.01 (t, J=8.8 Hz, 1H), 6.98 (m, 1H), 4.17 (d, J=6.4 Hz, 2H), 3.76 (br d, J=11.6 Hz, 2H), 2.82 (m, 2H), 2.15 (m, 1H), 1.81 (m, 2H), 1.34 (m, 2H). MS m/z (ESI) 483 (M+H)⁺.

Example-79

¹HNMR (400 MHz, DMSO-d₆) δ 12.1 (br s, 1H), 8.93 (br s, 1H), 8.19 (br s, 1H), 7.68 (m, 2H), 7.50 (m, 4H), 7.16 (m, 1H), 7.00 (m, 2H), 4.16 (d, J=6.4 Hz, 2H), 3.69 (br d, J=11.6 Hz, 2H), 2.65 (m, 2H), 2.53 (s, 3H), 2.1 (m, 1H), 1.81 (m, 2H), 1.30 (m, 2H). MS m/z (ESI) 446 (M+H)⁺.

Example-80

¹HNMR (400 MHz, DMSO-d₆) δ 12.1 (br s, 1H), 8.93 (br s, 1H), 8.18 (br s, 1H), 7.66 (m, 3H), 7.31 (m, 2H), 7.00 (m,

3H), 4.15 (d, J=6.4 Hz, 2H), 3.89 (s, 3H), 3.75 (m, 2H), 2.65 (m, 2H), 2.08 (m, 1H), 1.79 (m, 2H), 1.27 (m, 2H). MS m/z (ESI) 478 (M+H)⁺.

Example-81

¹HNMR (400 MHz, DMSO-d₆) δ 12.3 (br s, 1H), 8.95 (br s, 1H), 8.20 (br s, 1H), 7.75 (m, 4H), 7.45 (m, 2H), 7.01 (m, 2H), 4.17 (d, J=6.4 Hz, 2H), 3.66 (br d, J=12.0 Hz, 2H), 2.70 (m, 2H), 2.61 (s, 3H), 2.12 (m, 1H), 1.81 (m, 2H), 1.31 (m, 2H). MS m/z (ESI) 462 (M+H)⁺.

Example-82

¹HNMR (400 MHz, DMSO-d₆) δ 12.1 (br s, 1H), 8.92 (br s, 1H), 8.15 (br s, 1H), 8.03 (m, 2H), 7.96 (m, 2H), 7.67 (m, 2H), 6.98 (m, 2H), 4.12 (d, J=6.4 Hz, 2H), 3.71 (br d, J=12.0 Hz, 2H), 2.32 (m, 2H), 2.01 (m, 1H), 1.81 (m, 2H), 1.35 (m, 2H). MS m/z (ESI) 483 (M+H)⁺.

Example-83

¹HNMR (400 MHz, DMSO-d₆) δ 12.1 (br s, 1H), 8.94 (br s, 1H), 8.19 (br s, 1H), 7.80 (m, 2H), 7.68 (m, 1H), 7.45 (m, 1H), 7.24 (m, 1H), 6.97 (m, 2H), 4.15 (d, J=6.4 Hz, 2H), 3.89 (s, 3H), 3.75 (m, 2H), 2.64 (m, 2H), 2.08 (m, 1H), 1.80 (m, 2H), 1.35 (m, 2H). MS m/z (ESI) 523 (M+H)⁺.

Example-84

¹HNMR (400 M , DMSO-d₆) δ 12.1 (br s, 1H), 8.95 (br s, 1H), 8.19 (br s, 1H), 7.93 (m, 2H), 7.67 (m, 2H), 7.50 (m, 1H), 7.36 (m, 1H), 7.01 (m, 1H), 4.16 (d, J=6.4 Hz, 2H), 3.74 (m, 2H), 2.76 (m, 2H), 2.12 (m, 1H), 1.81 (m, 2H), 1.35 (m, 2H). MS m/z (ESI) 483 (M+H)⁺.

Example-85

¹HNMR (400 MHz, DMSO-d₆) δ 12.1 (br s, 1H), 8.95 (br s, 1H), 8.21 (br s, 1H), 7.67 (m, 3H), 7.35 (m, 1H), 7.22 (m, 1H), 7.01 (m, 2H), 4.16 (d, J=6.4 Hz, 2H), 3.83 (br d, J=12.4 Hz, 2H), 2.89 (m, 2H), 2.2 (m, 1H), 1.82 (m, 2H), 1.29 (m, 2H). MS m/z (ESI) 483 (M+H)⁺.

Example-86

¹HNMR (400 MHz, DMSO-d₆) δ 12.4 (br s, 1H), 8.92 (br s, 1H), 8.19 (m, 1H), 8.14 (br s, 1H), 8.0 (m, 1H), 7.84 (m, 2H), 7.67 (m, 2H), 6.98 (m, 2H), 4.12 (d, J=6.4 Hz, 2H), 3.72 (br d, J=12.4 Hz, 2H), 2.34 (m, 2H), 2.0 (m, 1H), 1.82 (m, 2H), 1.35 (m, 2H). MS m/z (ESI) 493 (M+H)⁺.

Example-87

¹HNMR (400 MHz, DMSO-d₆) δ 12.1 (br s, 1H), 8.94 (br s, 1H), 8.20 (m, 1H), 8.06 (m, 1H), 7.90 (m, 1H), 7.67 (m, 2H), 7.61 (m, 1H), 7.51 (m, 1H), 7.01 (m, 2H), 4.17 (d, J=6.4 Hz, 2H), 3.76 (br d, J=12.4 Hz, 2H), 2.76 (m, 2H), 2.1 (m, 1H), 1.82 (m, 2H), 1.32 (m, 2H). MS m/z (ESI) 482 (M+H)⁺.

Example-88

¹HNMR (400 MHz, DMSO-d₆) δ 12.1 (br s, 1H), 8.92 (br s, 1H), 8.15 (m, 1H), 7.95 (m, 2H), 7.69 (m, 3H), 6.98 (d, J=8.4 Hz, 2H), 4.13 (d, J=6.4 Hz, 2H), 3.69 (br d, J=12.4 Hz, 2H), 2.35 (m, 2H), 2.01 (m, 1H), 1.81 (m, 2H), 1.33 (m, 2H). MS m/z (ESI) 483 (M+H)⁺.

Example-89

¹HNMR (400 MHz, DMSO-d₆) δ 12.1 (br s, 1H), 8.90 (br s, 1H), 8.15 (m, 1H), 7.69 (m, 2H), 7.51 (m, 2H), 7.17 (d, J=8.0 Hz, 2H), 6.97 (d, J=8.4 Hz, 2H), 4.10 (d, J=6.4 Hz, 2H), 3.68 (br d, J=12.4 Hz, 2H), 2.91 (m, 1H), 2.21 (m, 2H), 1.83 (m, 3H), 1.36 (m, 2H), 1.22 (m, 9H). MS m/z (ESI) 456 (M+H)⁺.

Example-90

¹HNMR (400 MHz, DMSO-d₆) δ 12.2 (br s, 1H), 8.91 (br s, 1H), 8.15 (m, 1H), 7.81 (m, 2H), 7.66 (m, 2H), 7.51 (s, 3H), 6.97 (m, 2H), 4.11 (d, J=6.4 Hz, 2H), 3.64 (br d, J=12.4 Hz, 2H), 2.21 (m, 2H), 2.10 (s, 3H), 2.0 (m, 1H), 1.80 (m, 2H), 1.33 (m, 2H). MS m/z (ESI) 471 (M+H)⁺.

Example-91

¹HNMR (400 MHz, DMSO-d₆) δ 12.9 (br s, 1H), 8.84 (br s, 1H), 8.23 (m, 1H), 7.69 (m, 2H), 7.01 (m, 2H), 4.57 (s, 1H), 4.18 (m, 2H), 3.38 (m, 2H), 2.86 (s, 2H), 2.56 (m, 3H), 2.47 (m, 3H), 2.32 (s, 3H), 2.29 (m, 1H), 1.87 (m, 2H). MS m/z (ESI) 383 (M+H)⁺.

Example-92

¹HNMR (400 MHz, DMSO-d₆) δ 7.36 (m, 3H), 7.16 (br s, 1H), 7.04 (m, 2H), 6.76 (dd, J=8.0, 0.8 Hz, 1H), 6.51 (d, J=8.0 Hz, 1H), 5.94 (br s, 2H), 3.95 (d, J=6.4 Hz, 2H), 3.59 (s, 2H), 3.32 (s, 3H), 2.86 (d, J=10.8 Hz, 2H), 2.03 (t, J=10.8 Hz, 2H), 1.81 (m, 1H), 1.73 (d, J=12.4 Hz, 2H), 1.30 (dq, J=12.0, 3.6 Hz, 2H). MS m/z (APCI) 396 (M+H)⁺.

Example-93

¹HNMR (400 MHz, DMSO-d₆) δ 12.2 (br s, 1H), 8.98 (br s, 1H), 8.23 (m, 1H), 7.68 (m, 5H), 7.02 (m, 2H), 4.17 (s, 2H), 3.58 (br s, 2H), 2.84 (s, 2H), 2.02 (br s, 3H), 1.75 (br s, 2H), 1.39 (m, 2H). MS m/z (ESI) 434 (M+H)⁺.

Example-94

¹HNMR (400 MHz, DMSO-d₆) δ 13.0 (br s, 1H), 12.3 (m, 2H), 9.0 (br s, 1H), 8.16 (br s, 1H), 7.74 (m, 4H), 7.03 (m, 2H), 4.61 (m, 3H), 4.30 (m, 2H), 3.41 (m, 3H), 2.3 (m, 1H), 2.19 (m, 7H). MS m/z (ESI) 428 (M+H)⁺.

Example-95

¹HNMR (400 MHz, DMSO-d₆) δ 7.43 (m, 3H), 6.82 (d, J=8.4 Hz, 1H), 6.66 (br d, J=7.6 Hz, 1H), 6.39 (br s, 2H), 4.05 (m, 2H), 3.43 (m, 2H), 1.86 (m, 3H), 1.54 (m, 2H), 1.03 (m, 3H), 0.52 (m, 2H), 0.21 (br s, 2H). MS m/z (ESI) 328 (M+H)⁺.

Example-96

¹HNMR (400 MHz, DMSO-d₆) δ 7.36 (m, 3H), 6.82 (m, 4H), 6.57 (d, J=8.0 Hz, 1H), 6.11 (br s, 2H), 4.31 (m, 2H), 4.0 (m, 3H), 2.94 (m, 2H), 2.57 (m, 2H), 2.06 (m, 2H), 1.88 (m, 1H), 1.73 (m, 2H), 1.35 (m, 2H). MS m/z (ESI) 422 (M+H)⁺.

Example-97

¹HNMR (400 NM, DMSO-d₆) δ 7.73 (m, 3H), 7.66 (m, 2H), 7.32 (t, J=8.4 Hz, 1H), 7.11 (br s, 2H), 6.75 (d, J=8.4 Hz, 1H), 6.49 (d, J=7.6 Hz, 1H), 5.94 (br s, 2H), 3.95 (d, J=6.0 Hz,

2H), 3.73 (br d, J=11.6 Hz, 2H), 2.24 (m, 2H), 1.86 (m, 3H), 1.35 (m, 2H). MS m/z (ESI) 415 (M+H)⁺.

Example-98

¹HNMR (400 NM, DMSO-d₆) δ 7.29 (m, 8H), 6.76 (d, J=8.0 Hz, 1H), 6.52 (d, J=8.4 Hz, 1H), 5.94 (br s, 2H), 3.98 (d, J=6.0 Hz, 2H), 3.47 (s, 2H), 2.83 (m, 2H), 1.94 (m, 5H), 1.34 (m, 2H). MS m/z (ESI) 364 (M+H)⁺.

Example-99

¹HNMR (400 NM, DMSO-d₆) δ 7.34 (t, J=8.4 Hz, 1H), 7.19 (br s, 2H), 6.78 (m, 3H), 6.52 (d, J=8.0 Hz, 1H), 5.98 (s, 2H), 5.94 (br s, 2H), 3.98 (d, J=6.4 Hz, 2H), 3.37 (s, 2H), 2.82 (m, 2H), 1.86 (m, 5H), 1.33 (m, 2H). MS m/z (ESI) 408 (M+H)⁺.

Example-100

¹HNMR (400 MHz, DMSO-d₆) δ 7.34 (t, J=8.0 Hz, 1H), 7.19 (br s, 2H), 7.00 (m, 2H), 6.76 (d, J=8.4 Hz, 1H), 6.52 (d, J=8.0 Hz, 1H), 6.06 (s, 2H), 5.94 (br s, 2H), 3.99 (d, J=6.4 Hz, 2H), 3.46 (s, 2H), 2.85 (m, 2H), 2.02 (m, 5H), 1.34 (m, 2H). MS m/z (ESI) 442 (M+H)⁺.

Example-101

¹HNMR (400 NM, DMSO-d₆) δ 7.57 (m, 1H), 7.39 (m, 4H), 7.19 (br s, 2H), 6.76 (d, J=8.4 Hz, 1H), 6.53 (d, J=8.0 Hz, 1H), 5.94 (br s, 2H), 3.98 (d, J=6.4 Hz, 2H), 3.54 (s, 2H), 2.85 (m, 2H), 1.89 (m, 5H), 1.34 (m, 2H). MS m/z (ESI) 448 (M+H)⁺.

Example-102

¹HNMR (400 NM, DMSO-d₆) δ 7.42 (m, 2H), 7.32 (m, 3H), 7.19 (br s, 2H), 6.76 (d, J=8.4 Hz, 1H), 6.52 (d, J=8.0 Hz, 1H), 5.94 (br s, 2H), 3.99 (d, J=6.4 Hz, 2H), 3.50 (s, 2H), 2.82 (m, 2H), 1.88 (m, 5H), 1.34 (m, 2H). MS m/z (ESI) 448 (M+H)⁺.

Example-103

¹HNMR (400 MHz, DMSO-d₆) δ 7.46 (m, 1H), 7.34 (m, 2H), 7.23 (m, 4H), 6.76 (d, J=8.4 Hz, 1H), 6.52 (d, J=8.0 Hz, 1H), 5.94 (br s, 2H), 3.99 (d, J=6.4 Hz, 2H), 3.54 (s, 2H), 2.82 (m, 2H), 1.88 (m, 5H), 1.37 (m, 2H). MS m/z (ESI) 448 (M+H)⁺.

Example-104

¹HNMR (400 MHz, DMSO-d₆) δ 12.8 (s, 1H), 11.2 (s, 1H), 8.85 (s, 1H), 8.23 (s, 1H), 8.03 (m, 1H), 7.72 (m, 3H), 7.57 (m, 1H), 7.02 (m, 2H), 4.40 (d, J=4.8 Hz, 2H), 4.17 (d, J=6.4 Hz, 2H), 3.41 (m, 2H), 3.05 (m, 2H), 2.25 (m, 1H), 1.90 (m, 2H), 1.76 (m, 2H). MS m/z (ESI) 433 (M+H)⁺.

Example-105

¹HNMR (400 MHz, DMSO-d₆) δ 12.7 (s, 1H), 9.0 (s, 1H), 8.22 (s, 1H), 7.71 (m, 2H), 6.95 (m, 5H), 6.07 (s, 2H), 4.18 (m, 6H), 2.89 (m, 1H), 2.27 (m, 1H), 1.76 (m, 2H), 1.27 (m, 2H). MS m/z (ESI) 422 (M+H)⁺.

Example-106

¹HNMR (400 MHz, DMSO-d₆) δ 7.39 (m, 6H), 7.21 (m, 2H), 6.77 (d, J=8.0 Hz, 1H), 6.54 (d, J=8.4 Hz, 1H), 5.94 (br s, 2H), 4.54 (br s, 1H), 4.03 (d, J=6.4 Hz, 2H), 3.61 (br s, 1H), 3.09 (br s, 1H), 2.84 (br s, 1H), 2.14 (m, 1H), 1.74 (m, 2H), 1.32 (m, 2H). MS m/z (ESI) 428 (M+H)⁺.

Example-107

¹HNMR (400 MHz, DMSO-d₆) δ 7.55 (m, 1H), 7.34 (t, J=8.0 Hz, 1H), 7.23 (m, 2H), 7.15 (br s, 2H), 6.77 (d, J=8.4 Hz, 1H), 6.55 (d, J=8.0 Hz, 1H), 5.93 (br s, 2H), 4.55 (br d, J=13.6 Hz, 1H), 4.04 (d, J=6.4 Hz, 2H), 3.43 (m, 1H), 3.16 (m, 1H), 2.90 (m, 1H), 2.24 (m, 1H), 1.91 (m, 2H), 1.24 (m, 2H). MS m/z (ESI) 414 (M+H)⁺.

Example-108

¹HNMR (400 MHz, DMSO-d₆) δ 7.54 (m, 2H), 7.45 (m, 1H), 7.34 (t, J=8.4 Hz, 1H), 7.19 (br s, 2H), 6.76 (d, J=8.0 Hz, 1H), 6.55 (d, J=8.0 Hz, 1H), 5.93 (br s, 2H), 4.57 (br d, J=12.8 Hz, 1H), 4.04 (d, J=6.4 Hz, 2H), 3.27 (m, 1H), 3.13 (t, J=12.0 Hz, 1H), 2.88 (t, J=12.8 Hz, 1H), 2.23 (m, 1H), 1.92 (m, 1H), 1.75 (m, 1H), 1.32 (m, 2H). MS m/z (ESI) 447 (M+H)⁺.

Example-109

¹HNMR (400 MHz, DMSO-d₆) δ 8.17 (br s, 1H), 8.06 (d, J=1.6 Hz, 1H), 7.88 (m, 1H), 7.69 (m, 4H), 7.56 (t, J=8.0 Hz, 1H), 7.38 (m, 1H), 6.96 (d, J=8.0 Hz, 1H), 6.80 (d, J=8.0 Hz, 1H), 4.50 (br s, 1H), 4.11 (d, J=6.4 Hz, 2H), 3.56 (m, 2H), 2.84 (m, 1H), 2.26 (m, 1H), 1.74 (m, 2H), 1.33 (m, 2H). MS m/z (ESI) 447 (M+H)⁺.

Example-110

¹HNMR (400 MHz, DMSO-d₆) δ 7.88 (t, J=7.6 Hz, 1H), 7.78 (br s, 1H), 7.51 (t, J=7.6 Hz, 1H), 7.35 (t, J=8.0 Hz, 1H), 7.16 (br s, 2H), 6.77 (d, J=8.4 Hz, 1H), 6.54 (d, J=8.0 Hz, 1H), 5.94 (br s, 2H), 4.55 (br d, J=13.6 Hz, 1H), 4.03 (d, J=6.4 Hz, 2H), 3.40 (m, 1H), 3.16 (m, 1H), 2.88 (m, 1H), 2.24 (m, 1H), 1.91 (m, 2H), 1.25 (m, 2H). MS m/z (ESI) 464 (M+H)⁺

Example-111

¹HNMR (400 MHz, DMSO-d₆) δ 7.83 (m, 2H), 7.50 (m, 2H), 7.32 (t, J=8.4 Hz, 1H), 7.11 (br s, 2H), 6.77 (d, J=8.4 Hz, 1H), 6.50 (d, J=8.0 Hz, 1H), 5.93 (br s, 2H), 3.96 (d, J=6.0 Hz, 2H), 3.69 (m, 2H), 2.27 (m, 2H), 1.83 (m, 3H), 1.36 (m, 2H). MS m/z (ESI) 432 (M+H)⁺.

Example-112

¹HNMR (400 MHz, DMSO-d₆) δ 7.89 (d, J=8.4 Hz, 2H), 7.63 (d, J=8.4 Hz, 2H), 7.32 (t, J=8.4 Hz, 1H), 7.11 (br s, 2H), 6.77 (d, J=8.4 Hz, 1H), 6.49 (d, J=8.0 Hz, 1H), 5.93 (br s, 2H), 3.96 (d, J=6.0 Hz, 2H), 3.71 (m, 2H), 2.31 (m, 2H), 1.87 (m, 3H), 1.36 (m, 2H). MS m/z (ESI) 464 (M+H)⁺.

Example-113

¹H NMR (500 MHz, DMSO-D₆) δ 7.32 (M, 3H), 7.21 (BS, 2H), 6.93 (m, 2H), 6.77 (d, J=8.5 Hz, 1H), 6.53 (d, J=7.5 Hz, 1H), 5.94 (s, 2H), 3.99 (d, J=5.5 Hz, 2H), 3.77 (s, 3H), 3.47 (s, 2H), 2.87 (d, J=11.5 Hz, 2H), 2.00 (t, J=11.0 Hz, 2H), 1.86 (s, 1H), 1.74 (d, J=11.5 Hz, 2H), 1.36 (d, J=9.5 Hz, 2H). MS m/z (ESI) 395 (M+H)⁺.

Example-114

¹H NMR (500 MHz, DMSO-D₆) δ 7.34 (T, J=8.0 HZ, 1H), 7.22 (t, J=8.0 Hz, 1H), 7.19 (bs, 2H), 6.87 (d, J=8.0 Hz, 2H), 6.81 (dd, J=2.5 Hz, 1H), 6.76 (d, J=7.5 Hz, 1H), 6.53 (d, J=7.5 Hz, 1H), 5.93 (s, 2H), 3.99 (d, J=6.5 Hz, 2H), 3.74 (s, 3H), 3.44 (s, 2H), 2.85 (d, J=11.5 Hz, 2H), 1.96 (t, J=11.0 Hz, 2H), 1.86 (s, 1H), 1.74 (d, J=11.5 Hz, 2H), 1.36 (m, 2H). MS m/z (ESI) 395 (M+H)+.

Example-115

$^1$HNMR (400 NM, DMSO-d$_6$) δ 7.35 (m, 1H), 7.20 (m, 2H), 6.77 (m, 2H), 6.62 (m, 2H), 6.54 (m, 1H), 5.95 (br s, 2H), 4.51 (br s, 1H), 4.03 (d, J=6.0 Hz, 2H), 3.67 (m, 1H), 2.91 (m, 8H), 2.20 (br s, 1H), 1.74 (m, 2H), 1.30 (m, 2H). MS m/z (ESI) 421 (M+H)+.

Example-116

$^1$HNMR (400 NM, DMSO-d$_6$) δ 12.8 (s, 1H), 11.3 (s, 1H), 8.83 (s, 1H), 8.24 (s, 1H), 7.79 (m, 5H), 7.02 (m, 2H), 4.19 (m, 4H), 3.39 (m, 2H), 2.89 (m, 2H), 2.20 (m, 1H), 1.91 (m, 4H). MS m/z (ESI) 432 (M+H)+.

Example-117

$^1$H NMR (400 NM, DMSO-D$_6$) δ 7.34 (t, J=8.0 HZ, 1H), 7.19 (bs, 2H), 6.76 (d, J=7.6 Hz, 1H), 6.53 (d, J=7.6 Hz, 1H), 5.94 (d, J=7.6 Hz, 2H), 3.99 (d, J=6.0 Hz, 2H), 2.79 (d, J=9.6 Hz, 2H), 2.15 (s, 3H), 1.73 (d, J=12.8 Hz, 2H), 1.20 (d, J=25.2 Hz, 2H). MS m/z (ESI) 288 (M+H)+.

Example-118

$^1$HNMR (400 NM, DMSO-d$_6$) δ 8.47-8.51 (m, 1H), 7.76 (td, J=8.0, 0.8 Hz 1H), 7.44 (d, J=8.0 Hz 1H), 7.37 (t, J=8.0 Hz 1H), 7.33 (br s, 2H), 7.2-7.28 (m, 1H), 6.78 (d, J=8.0 Hz, 1H), 6.57 (d, J=8.0 Hz, 1H), 6.06 (s, 2H), 4.01 (d, J=6.0 Hz, 2H), 3.6 (s, 2H), 2.84-2.92 (m, 2H), 2.03-2.12 (m, 2H), 1.71-1.8 (m, 3H), 1.21-1.46 (m, 2H). MS m/z (ESI) 366 (M+H)+.

Example-119

$^1$HNMR (400 NM, DMSO-d$_6$) δ 8.48-8.53 (m, 2H), 7.3-7.38 (m, 3H), 7.2 (s, 2H), 6.77 (d, J=8.0 Hz, 1H), 6.54 (d, J=8.0 Hz, 1H), 5.94 (s, 2H), 4.0 (d, J=6.0 Hz, 2H), 3.51 (s, 2H), 2.8-2.88 (m, 2H), 1.96-2.08 (m, 2H), 1.71-1.95 (m, 3H), 1.22-1.46 (m, 2H). MS m/z (ESI) 366 (M+H)+.

Example-120

$^1$HNMR (400 NM, DMSO-d$_6$) δ 8.46-8.52 (m, 2H), 7.69-7.73 (m, 1H), 7.34-7.39 (m, 2H), 7.26 (br s, 2H), 6.78 (dd, J=8.0, 0.8 Hz, 1H), 6.55 (dd, J=8.0, 0.8 Hz, 1H), 6.03 (s, 2H), 4.0 (d, J=6.4 Hz, 2H), 3.51 (s, 2H), 2.8-2.88 (m, 2H), 1.94-2.06 (m, 2H), 1.7-1.94 (m, 3H), 1.29-1.42 (m, 2H). MS m/z (ESI) 366 (M+H)+.

Example-121

$^1$HNMR (400 MHz, DMSO-d$_6$) δ 7.34 (t, J=8.0 Hz, 1H), 7.20 (br s, 2H), 6.76 (dd, J=8.4, 0.8 Hz, 1H), 6.52 (d, J=8.0 Hz, 1H), 5.95 (br s, 2H), 3.97 (d, J=6.4 Hz, 2H), 3.81 (d, J=11.2 Hz, 2H), 2.48 (m, 1H), 2.31 (d, J=6.8 Hz, 2H), 1.99 (m, 2H), 1.91-1.59 (m, 9H), 1.30 (dq, J=12.0, 3.2 Hz, 2H). MS m/z (ESI) 342 (M+H)+.

Example-122

$^1$HNMR (400 MHz, DMSO-d$_6$) δ 7.34 (t, J=8.0 Hz, 1H), 7.20 (br s, 2H), 7.09 (m, 3H), 6.76 (d, J=8.4 Hz, 1H), 6.52 (d, J=8.0 Hz, 1H), 5.95 (br s, 2H), 3.98 (d, J=6.4 Hz, 2H), 3.82 (s, 3H), 3.40 (s, 2H), 2.84 (d, J=11.2 Hz, 2H), 1.94 (t, J=10.8 Hz, 2H), 1.85 (m, 1H), 1.73 (d, J=12.0 Hz, 2H), 1.34 (q, J=12.0 Hz, 2H). MS m/z (ESI) 412 (M+H)+

Example-123

$^1$HNMR (400 MHz, DMSO-d$_6$) δ 7.68 (d, J=8.0 Hz, 2H), 7.53 (d, J=8.0 Hz, 2H), 7.34 (t, J=8.0 Hz, 1H), 7.21 (br s, 2H), 6.77 (dd, J=8.4, 0.8 Hz, 1H), 6.53 (d, J=7.6 Hz, 1H), 5.95 (s, 2H), 3.99 (d, J=6.4 Hz, 2H), 3.57 (s, 2H), 2.83 (d, J=11.6 Hz, 2H), 2.01 (t, J=11.6 Hz, 2H), 1.87 (m, 1H), 1.75 (d, J=11.2 Hz, 2H), 1.37 (dq, J=12.0, 3.2 Hz, 2H). MS m/z (ESI) 432 (M+H)+.

Example-124

$^1$HNMR (400 MHz, DMSO-d$_6$) δ 7.34 (t, J=8.0 Hz, 1H), 7.20 (m, 4H), 6.87 (d, J=8.4 Hz, 2H), 6.76 (dd, J=8.4, 0.8 Hz, 1H), 6.52 (d, J=8.4 Hz, 1H), 5.94 (br s, 2H), 3.98 (d, J=6.0 Hz, 2H), 3.73 (s, 3H), 3.39 (s, 2H), 2.84 (d, J=11.2 Hz, 2H), 1.93 (t, J=10.8 Hz, 2H), 1.85 (m, 1H), 1.73 (d, J=12.0 Hz, 2H), 1.34 (dq, J=12.0, 3.2 Hz, 2H). MS m/z (ESI) 394 (M+H)+.

Example-125

$^1$HNMR (400 MHz, DMSO-d$_6$) δ 7.34 (t, J=8.0 Hz, 1H), 7.19 (s, 2H), 6.77 (dd, J=8.0, 0.8 Hz, 1H), 6.53 (dd, J=8.0, 0.8 Hz, 1H), 5.93 (s, 2H), 3.98 (d, J=6.04 Hz, 2H), 3.78-3.86 (m, 1H), 3.27-3.44 (m, 2H), 2.83-2.96 (m, 2H), 2.3-2.37 (m, 1H), 2.18-2.24 (m, 1H), 1.05-2.03 (m, 13H). MS m/z (ESI) 372 (M+H)+.

Example-126

$^1$HNMR (400 MHz, DMSO-d$_6$) δ 7.35 (t, J=8.0 Hz, 1H), 7.19 (s, 2H), 6.77 (dd, J=8.0, 0.8 Hz, 1H), 6.54 (d, J=8.0, Hz, 1H), 5.94 (s, 2H), 4.01 (d, J=6.0 Hz, 2H), 3.68-3.74 (m, 2H), 3.21-3.28 (m, 4H), 2.66-2.75 (m, 2H), 2.01-2.12 (m, 1H), 1.7-1.81 (m, 6H), 1.22-1.34 (m, 2H). MS m/z (ESI) 372 (M+H)+.

Example-127

$^1$HNMR (400 MHz, DMSO-d$_6$) δ 7.34 (t, J=8.0 Hz, 1H), 7.19 (s, 2H), 6.77 (dd, J=8.0, 0.8 Hz, 1H), 6.54 (d, J=8.0, Hz, 1H), 5.94 (s, 2H), 4.01 (d, J=6.4 Hz, 2H), 3.61-3.69 (m, 2H), 3.54-3.59 (m, 4H), 3.08-3.14 (m, 4H), 2.72-2.82 (m, 2H), 2.02-2.13 (m, 1H), 1.72-1.8 (m, 2H), 1.2-1.34 (m, 2H). MS m/z (ESI) 388 (M+H)+.

Example-128

$^1$HNMR (400 MHz, DMSO-d$_6$) δ 7.35 (t, J=8.0 Hz, 1H), 7.3 (br s, 2H), 6.78 (dd, J=8.0, 0.8 Hz, 1H), 6.57 (dd, J=8.0, 0.8 Hz, 1H), 6.05 (s, 2H), 3.99 (d, J=6.4 Hz, 2H), 3.89-3.96 (m, 1H), 3.69-3.76 (m, 1H), 3.56-3.62 (m, 1H), 3.0-3.07 (m, 1H), 2.88-2.96 (m, 1H), 2.85-2.91 (m, 2H), 1.68-2.1 (m, 8H), 1.26-1.51 (m, 3H). MS m/z (ESI) 358 (M+H)+.

Example-129

$^1$HNMR (400 MHz, DMSO-d$_6$) δ 7.50 (m, 4H), 7.35 (t, J=8.0 Hz, 1H), 7.09 (br s, 2H), 6.77 (d, J=8.4 Hz, 1H), 6.52 (d, J=8.0 Hz, 1H), 5.91 (br s, 2H), 4.81 (s, 2H), 4.39 (s, 2H), 3.48 (m, 2H), 3.08 (m, 1H), 2.14 (m, 5H), 1.27 (m, 9H). MS m/z (ESI) 420 (M+H)+.

Example-130

¹HNMR (400 MHz, DMSO-d$_6$) δ 7.62 (m, 4H), 7.34 (t, J=8.0 Hz, 1H), 7.19 (br s, 2H), 6.76 (d, J=8.0 Hz, 1H), 6.52 (d, J=8.0 Hz, 1H), 5.94 (br s, 2H), 3.99 (d, J=6.4 Hz, 2H), 3.58 (s, 2H), 2.83 (m, 2H), 2.01 (m, 2H), 1.89 (m, 1H), 1.74 (m, 2H), 1.35 (m, 2H). MS m/z (ESI) 432 (M+H)⁺.

Example-131

¹HNMR (400 MHz, DMSO-d$_6$) δ 7.79 (m, 1H), 7.68 (m, 1H), 7.46 (m, 1H), 7.34 (d, J=8.0 Hz, 1H), 7.20 (br s, 2H), 6.76 (dd, J=8.4, 0.8 Hz, 1H), 6.53 (d, J=8.0 Hz, 1H), 5.94 (br s, 2H), 4.00 (d, J=6.4 Hz, 2H), 3.62 (s, 2H), 2.83 (m, 2H), 2.06 (m, 2H), 1.92 (m, 1H), 1.76 (m, 2H), 1.37 (m, 2H). MS m/z (ESI) 432 (M+H)⁺.

Example-132

¹HNMR (400 M, DMSO-d$_6$) δ 7.34 (m, 2H), 7.20 (br s, 2H), 7.08 (m, 4H), 6.76 (dd, J=8.4, 0.8 Hz, 1H), 6.52 (d, J=8.0 Hz, 1H), 5.94 (br s, 2H), 4.00 (d, J=6.4 Hz, 2H), 3.49 (s, 2H), 2.83 (m, 2H), 1.99 (m, 2H), 1.87 (m, 1H), 1.74 (m, 2H), 1.35 (m, 2H). MS m/z (ESI) 382 (M+H)⁺.

Example-133

¹HNMR (400 MHz, DMSO-d$_6$) δ 7.34 (t, J=8.4 Hz, 1H), 7.20 (br s, 2H), 6.76 (dd, J=8.4, 0.8 Hz, 1H), 6.53 (d, J=7.2 Hz, 1H), 6.46 (m, 2H), 6.37 (m, 1H), 5.93 (br s, 2H), 4.00 (d, J=6.4 Hz, 2H), 3.72 (s, 6H), 3.40 (s, 2H), 2.84 (m, 2H), 1.96 (m, 5H), 1.35 (m, 2H). MS m/z (ESI) 424 (M+H)⁺.

Example-134

¹HNMR (400 MHz, DMSO-d$_6$) δ 7.34 (t, J=8.0 Hz, 1H), 7.20 (br s, 2H), 6.76 (t, J=8.4 Hz, 1H), 6.76 (dd, J=8.4, 0.8 Hz, 1H), 6.64 (m, 1H), 6.59 (m, 2H), 6.52 (m, 1H), 5.93 (br s, 2H), 4.00 (d, J=6.4 Hz, 2H), 3.40 (s, 2H), 2.85 (m, 8H), 1.92 (m, 5H), 1.34 (m, 2H). MS m/z (ESI) 407 (M+H)⁺.

Example-135

¹HNMR (500 MHz, DMSO-D$_6$) δ 7.55 (BR S, 2H), 7.37-7.44 (m, 2H), 7.94-7.98 (m, 2H), 6.82 (d, J=8.4 Hz, 1H), 6.64 (d, J=8.4 Hz, 1H), 6.32 (s, 2H), 4.03 (d, J=6.0 Hz, 2H), 3.69 (s, 2H), 2.88-2.94 (m, 2H), 1.96-2.04 (m, 2H), 1.82-1.92 (m, 1H), 1.7-21.78 (m, 2H), 1.2-1.39 (m, 3H). MS m/z (ESI) 371 (M+H)⁺.

Example-136

¹HNMR (400 MHz, DMSO-d$_6$) δ 7.34 (t, J=8.0 Hz, 1H), 7.2 (br s, 2H), 6.77 (dd, J=8.0, 0.8 Hz, 1H), 6.53 (dd, J=8.0, 0.8 Hz, 1H), 5.93 (s, 2H), 5.89 (s, 1H), 3.99 (d, J=6.4 Hz, 2H), 3.7 (s, 3H), 3.43 (s, 2H), 2.82-2.88 (m, 2H), 2.08 (s, 3H), 1.7-2.01 (m, 5H), 1.27-1.39 (m, 2H). MS m/z (ESI) 384 (M+H)⁺.

Example-137

¹HNMR (400 MHz, DMSO-d$_6$) δ 7.34 (t, J=8.0 Hz, 1H), 7.20 (br s, 2H), 7.05 (m, 3H), 6.76 (dd, J=8.4, 0.8 Hz, 1H), 6.53 (d, J=8.4 Hz, 1H), 5.94 (br s, 2H), 4.00 (d, J=6.4 Hz, 2H), 3.50 (s, 2H), 2.84 (d, J=11.6 Hz, 2H), 2.01 (t, J=10.8 Hz, 2H), 1.88 (m, 1H), 1.75 (d, J=11.6 Hz, 2H), 1.37 (dq, J=12.4, 3.6 Hz, 2H). MS m/z (APCI) 400 (M+H)⁺.

Example-138

¹HNMR (400 MHz, DMSO-d$_6$) δ 7.34 (t, J=8.0, 1H), 7.20 (br s, 2H), 6.77 (dd, J=8.4, 0.8 Hz, 1H), 6.53 (d, J=8.0 Hz, 1H), 5.94 (br s, 2H), 3.98 (d, J=6.0 Hz, 2H), 2.84 (d, J=12.0 Hz, 2H), 2.01 (d, J=7.2 Hz, 2H), 1.89-1.72 (m, 6H), 1.33 (dq, J=12.0, 3.6 Hz, 2H), 0.84 (d, J=6.8 Hz, 6H). MS m/z (APCI) 330 (M+H)⁺.

Example-139

¹HNMR (400 MHz, DMSO-d$_6$) δ 7.34 (t, J=8.0, 1H), 7.20 (br s, 2H), 6.76 (dd, J=8.4, 0.8 Hz, 1H), 6.53 (d, J=8.0 Hz, 1H), 5.95 (br s, 2H), 3.98 (d, J=6.4 Hz, 2H), 2.88 (d, J=11.2 Hz, 2H), 2.26 (m, 2H), 1.87 (m, 3H), 1.73 (d, J=12.4 Hz, 2H), 1.55 (m, 1H), 1.31 (m, 4H), 0.87 (d, J=6.8 Hz, 6H). MS m/z (APCI) 344 (M+H)⁺.

Example-140

¹HNMR (400 MHz, DMSO-d$_6$) δ 7.55 (m, 1H), 7.48 (dd, J=7.6, 1.6 Hz, 1H), 7.36 (m, 2H), 7.20 (br s, 2H), 6.77 (dd, J=8.4, 0.8 Hz, 1H), 6.54 (d, J=7.6 Hz, 1H), 5.95 (br s, 2H), 4.00 (d, J=6.0 Hz, 2H), 3.60 (s, 2H), 2.88 (d, J=11.6 Hz, 2H), 2.10 (t, J=10.4 Hz, 2H), 1.90 (m, 1H), 1.77 (d, J=10.4 Hz, 2H), 1.37 (dq, J=12.4, 3.2 Hz, 2H). MS m/z (APCI) 432 (M+H)⁺.

Example-141

¹HNMR (400 MHz, DMSO-d$_6$) δ 7.34 (t, J=8.0, 1H), 7.19 (br s, 2H), 6.76 (d, J=8.4, Hz, 1H), 6.53 (d, J=8.0 Hz, 1H), 5.94 (br s, 2H), 3.98 (d, J=6.0 Hz, 2H), 2.83 (d, J=11.2 Hz, 2H), 2.05 (d, J=7.2 Hz, 2H), 1.88-1.63 (m, 10H), 1.47 (m, 1H), 1.36-1.10 (m, 5H), 0.83 (m, 2H). MS m/z (APCI) 370 (M+H)⁺.

Example-142

¹HNMR (400 MHz, DMSO-d$_6$) δ 7.55 (d, J=8.0 Hz, 1H), 7.46 (d, J=8.4 Hz, 1H), 7.33 (m, 2H), 7.22 (br s, 2H), 6.77 (dd, J=8.4, 0.8 Hz, 1H), 6.53 (d, J=8.0 Hz, 1H), 6.00 (br s, 2H), 3.97 (d, J=6.4 Hz, 2H), 3.68 (s, 2H), 2.86 (d, J=11.6 Hz, 2H), 2.20 (t, J=11.2 Hz, 2H), 1.89 (m, 1H), 1.74 (d, J=11.2 Hz, 2H), 1.26 (dq, J=11.6, 3.2 Hz, 2H). MS m/z (APCI) 432 (M+H)⁺.

Example-143

¹HNMR (400 MHz, DMSO-d$_6$) δ 7.34 (t, J=8.0 Hz, 1H), 7.25-7.12 (m, 5H), 6.76 (dd, J=8.0, 0.8 Hz, 1H), 6.51 (d, J=7.6 Hz, 1H), 5.94 (br s, 2H), 3.99 (d, J=6.4 Hz, 2H), 3.53 (br s, 2H), 2.86 (d, J=10.8 Hz, 2H), 2.04 (t, J=10.4 Hz, 2H), 1.87 (m, 1H), 1.75 (d, J=10.8 Hz, 2H), 1.36 (dq, J=12.0, 3.6 Hz, 2H). MS m/z (APCI) 400 (M+H)⁺.

Example-144

¹HNMR (400 MHz, DMSO-d$_6$) δ 7.34 (t, J=8.0 Hz, 1H), 7.20 (br s, 2H), 6.76 (dd, J=8.4, 0.8 Hz, 1H), 6.51 (d, J=8.0 Hz, 1H), 5.93 (br s, 2H), 3.98 (d, J=6.4 Hz, 2H), 2.87 (d, J=11.2 Hz, 2H), 2.24 (t, J=7.2 Hz, 2H), 1.87 (m, 3H), 1.73 (m, 2H), 1.41-1.25 (m, 10H), 0.86 (m, 3H). MS m/z (APCI) 358 (M+H)⁺.

Example-145

$^1$HNMR (400 MHz, DMSO-d$_6$) δ 7.46-7.49 (m, 1H), 7.35 (t, J=8.0 Hz, 1H), 7.24 (br s, 2H), 7.04 (dd, J=4.8, 1.2 Hz, 1H), 6.77 (dd, J=8.0, 0.8 Hz, 1H), 6.53 (dd, J=8.0, 0.8 Hz, 1H), 5.99 (s, 2H), 3.99 (d, J=6.4 Hz, 2H), 3.48 (s, 2H), 2.82-2.9 (m, 2H), 2.08 (s, 3H), 1.69-2.0 (m, 5H), 1.28-1.4 (m, 2H). MS m/z (ESI) 370 (M+H)$^+$.

Example-146

$^1$HNMR (400 MHz, DMSO-d$_6$) δ 7.35 (t, J=8.0 Hz, 1H), 7.23 (br s, 2H), 7.01 (m, 2H), 6.94 (m, 1H), 6.76 (dd, J=8.8, 0.8 Hz, 1H), 6.53 (m, 1H), 5.98 (br s, 2H), 3.98 (d, J=6.4 Hz, 2H), 3.37 (s, 2H), 2.82 (m, 2H), 2.25 (m, 6H), 1.92 (m, 3H), 1.73 (m, 2H), 1.30 (m, 2H). MS m/z (ESI) 392 (M+H)$^+$.

Example-147

$^1$HNMR (400 MHz, DMSO-d$_6$) δ 7.41 (m, 1H), 7.33 (t, J=8.0 Hz, 1H), 7.19 (br s, 2H), 7.09 (t, J=8.0 Hz, 2H), 6.76 (d, J=7.6 Hz, 1H), 6.51 (d, J=8.0 Hz, 1H), 5.98 (br s, 2H), 3.95 (d, J=6.0 Hz, 2H), 3.59 (br s, 2H), 2.86 (d, J=10.8 Hz, 2H), 2.03 (t, J=11.2 Hz, 2H), 1.82 (m, 1H), 1.74 (d, J=12.8 Hz, 2H), 1.32 (dq, J=12.0, 2.8 Hz, 2H). MS m/z (APCI) 400 (M+H)$^+$.

Example-148

$^1$HNMR (400 MHz, DMSO-d$_6$) δ7.37 (t, J=8.0 Hz, 2H), 7.25 (m, 3H), 6.78 (dd, J=8.4, 0.8 Hz, 1H), 6.56 (d, J=7.6 Hz, 1H), 6.07 (br s, 2H), 4.01 (d, J=6.0 Hz, 2H), 3.47 (s, 2H), 2.83 (d, J=11.6 Hz, 2H), 2.00 (t, J=9.6 Hz, 2H), 1.88 (m, 1H), 1.75 (d, J=11.2 Hz, 2H), 1.37 (dq, J=12.4, 3.2 Hz, 2H). MS m/z (APCI) 418 (M+H)$^+$.

Example-149

$^1$HNMR (400 MHz, DMSO-d$_6$) δ 7.40 (t, J=8.0 Hz, 1H), 7.33 (m, 3H), 7.13 (m, 3H), 6.80 (dd, J=8.0, 0.8 Hz, 1H), 6.61 (d, J=8.0 Hz, 1H), 6.23 (br s, 2H), 4.01 (d, J=6.0 Hz, 2H), 3.46 (s, 2H), 2.84 (d, J=12.0 Hz, 2H), 1.97 (t, J=11.6 Hz, 2H), 1.88 (m, 1H), 1.74 (d, J=11.2 Hz, 2H), 1.34 (dq, J=12.4, 3.2 Hz, 2H). MS m/z (APCI) 382 (M+H)$^+$.

Example-150

$^1$HNMR (400 MHz, DMSO-d$_6$) δ 7.49 (m, 2H), 7.35 (t, J=8.0 Hz, 1H), 7.21 (br s, 2H), 6.77 (dd, J=8.4, 0.8 Hz, 1H), 6.54 (d, J=7.2 Hz, 1H), 5.99 (br s, 2H), 3.99 (d, J=6.4 Hz, 2H), 3.51 (s, 2H), 2.85 (d, J=11.6 Hz, 2H), 2.02 (t, J=11.6 Hz, 2H), 1.86 (m, 1H), 1.75 (d, J=11.6 Hz, 2H), 1.35 (dq, J=12.0, 3.2 Hz, 2H). MS m/z (APCI) 418 (M+H)$^+$.

Example-151

$^1$HNMR (400 MHz, DMSO-d$_6$) δ 8.0 (s, 1H), 7.42 (t, J=8.0 Hz, 1H), 7.31 (br s, 2H), 6.8 (d, J=8.0 Hz, 1H), 6.62 (d, J=8.0 Hz, 1H), 6.19 (s, 2H), 4.18-4.26 (m, 1H), 4-4.12 (m, 1H), 4.04 (d, J=6.4 Hz, 2H), 3.7-3.76 (m, 2H), 3.15-3.2 (m, 2H), 3.04-3.12 (m, 2H), 2.61-2.7 (m, 1H), 2.16-2.27 (m, 2H), 1.78-1.88 (m, 2H), 1.06-1.3 (m, 5H), 0.82-0.94 (m, 2H). MS m/z (ESI) 371 (M+H)$^+$.

Example-152

$^1$HNMR (400 MHz, DMSO-d$_6$) δ 8.0 (s, 1H), 7.36 (t, J=8.0 Hz, 2H), 7.26 (br s, 2H), 7.06 (d, J=0.8 Hz, 1H), 6.78 (d, J=8.0 Hz, 1H), 6.74 (d, J=0.8 Hz, 1H), 6.57 (d, J=8.0 Hz, 1H), 6.10 (s, 2H), 4.0 (d, J=6.4 Hz, 2H), 3.64 (s, 3H), 3.51 (s, 2H), 2.77-2.84 (m, 2H), 1.7-2.05 (m, 5H), 1.22-1.36 (m, 2H). MS m/z (ESI) 369 (M+H)$^+$.

Example 153

5-[4-(3-Chlorobenzyl)cyclohexylmethoxy]quinazoline-2,4-diamine

Step 1: 4-(3-Chlorobenzyl)cyclohexanecarboxylic Acid

In a 50 ml beaker, Zn dust (3.6 g; 54 mmol) was added to 1N HCl and mixture was stirred with a glass rod. Aqueous was decanted off and solids were added to a mixture of trans-4-(3-chlorobenzoyl)cyclohexane-1-carboxylic acid (718 mg; 2.69 mmol) in 30 mL of formic acid. Mixture was heated to reflux for 2 hours. The reaction was cooled to room temperature and white solids were filtered off and rinsed with diethyl ether. Filtrate was concentrated and residue was taken up in a 40 mL mixture of diethyl ether and water (1:1). Organics were separated and aqueous was re-extracted with 2×20 mL of diethyl ether. Combined organics were washed with sat. NaHCO$_3$, water, brine, and dried over MgSO$_4$. Title compound was obtained as a crude oil. 550 mg (81% crude yield).

Step 2: [4-(3-Chlorobenzyl)cyclohexyl]methanol 4-(3-Chlorobenzyl)cyclohexanecarboxylic acid (550 mg; 2.2 mmol) was cooled to 0° C. in 5 mL of anhydrous tetrahydrofuran under nitrogen flow, and BH3 THF was added over 5 minutes. Mixture was warmed to room temperature. After 3.5 hours, mixture was cooled to 0° C. and quenched with slow additions of sat. NH$_4$Cl. Mixture was stirred for 20 minutes and water was added to dissolve precipitates. Mixture was extracted 3×20 mL with ethyl acetate, and combined organics were washed with brine and dried over MgSO$_4$. Material was purified via flash chromatography using 1-5% methanol in dichloromethane gradient to obtained 173 mgs of title compound. (33% yield)

Step 3: 2-[4-(3-Chlorobenzyl)cyclohexylmethoxy]-6-fluorobenzonitrile

[4-(3-Chlorobenzyl)cyclohexyl]-methanol (150 mg; 0.63 mmol) was added to a suspension of sodium hydride (33 mg; 0.82 mmol) in 3 mL of dimethylformamide at 0° C. After 2 hours, mixture was added to a mixture of 2,6-difluorobenzonitrile (88 mg; 0.63 mmol) in 2 mL of dimethylformamide at 0° C. After 16 hours mixture was quenched with 5 g of ice. Aqueous mixture was extracted with 5×15 mL of ethyl acetate. Combined ethyl acetates were washed with 6×15 mL water, brine and dried over MgSO$_4$. Residue was purified via flash chromatography using 5-15% ethyl acetate in hexanes gradient to give 173 mgs of title compound. (77% yield).

Step 4: 5-[4-(3-Chlorobenzyl)cyclohexylmethoxy] quinazoline-2,4-diamine (Method F)

2-[4-(3-Chlorobenzyl)cyclohexylmethoxy]-6-fluorobenzonitrile (150 mg; 0.42 mmol) was heated to 135° C. in the presence of guanidine carbonate (76 mg; 0.42 mmol) in 1.5 mLs of dimethylacetamide. After 6 hours, mixture was cooled to room temperature and 2 mLs of water added. After 30 minutes solids were collected by filtration. Solids were purified by trituration using a 3:1 mixture of ethyl alcohol and water. Solids collected by filtration to give title compound as a white solid. (128 mgs; 76% yield).

$^1$HNMR (500 MHz, DMSO-$d_6$) δ 7.31 (m, 2H), 7.24 (m, 2H), 7.18 (br s, 2H), 6.75 (dd, J=8.5, 1.0 Hz, 1H), 6.50 (d, J=7.5 Hz, 1H), 5.93 (br s, 2H), 3.92 (d, J=5.5 Hz, 2H), 2.5 (m, 2H), 1.82 (m, 3H), 1.67 (m, 2H), 1.49 (m, 1H), 1.03 (m, 4H). MS m/z (ESI) 398 (M+H)$^+$.

Example 154

5-[4-(2-Fluorobenzyl)cyclohexylmethoxy]quinazoline-2,4-diamine

Step 1: 4-(2-Fluorobenzoyl)cyclohexanecarboxylic Acid Methyl Ester

In an oven dried 1 neck round bottom flask with reflux condenser and stirbar, trans-4-carbomethoxycyclohexane-1-carboxylic acid (840 mg; 4.5 mmol) was heated to reflux in the presence of 15 mL thionyl chloride. After 3 hours reflux, mixture cooled to 40° C. under nitrogen flow, and excess thionyl chloride was removed at reduced pressure. Residue was taken up in 5 mL of dry tetrahydrofuran and added to a 0° C. mixture of 2-fluorophenylzinc iodide (9.0 mL; 4.5 mmol), tetrakis(triphenylphospine)palladium (0) (272 mg; 0.2 mmol) in 10 mL anhydrous tetrahydrofuran. Mixture was allowed to warm to room temperature over 16 hours. Reaction was quenched with 6 mL 1N HCl and ethyl acetate was taken in. Organics separated and aqueous re-extracted with 20 mL ethyl acetate. Combined organics were washed with sat. NaHCO$_3$, water, brine and dried over MgSO$_4$. Material was purified via flash silica plug (10:1) using 15% ethyl acetate in hexanes isocratic to give 800 mg of title compound. (67% yield)

Step 2: 4-(2-Fluorobenzyl)cyclohexanecarboxylic Acid Methyl Ester (Method G)

In an 18 mL vial with stir bar and 4-(2-fluorobenzoyl)cyclohexanecarboxylic acid methyl ester (333 mg; 1.2 mmol), trifluoroacetic acid (4 mL) was chilled to 0° C. and triethylsilane (700 mg; 6.0 mmol) was added over 1 minute. Mixture was allowed to warm to room temperature. After 48 hours, mixture was concentrated in vacuo and reduced by half volume. Mixture was poured into cold KOH solution and pH adjust further to pH 6. Aqueous mixture was extracted 3×5 mL ethyl acetate. Combined ethyl acetate was washed with brine and dried over MgSO$_4$. Crude oil was purified via (20:1) flash chromatography 0-10% ethyl acetate in hexanes to give 250 mg of title compound. (83% yield).

Step 3: [4-(2-Fluorobenzyl)cyclohexyl]methanol (Method H)

In a dry 50 mL 1 neck round bottom flask, lithium aluminium hydride (150 mg; 4.0 mmol) was suspended in dry tetrahydrofuran at 0° C. under nitrogen flow. Dissolved 4-(2-fluorobenzyl)cyclohexanecarboxylic acid methyl ester was added over 2 minutes and mixture was allowed to warm to room temperature. After 3 hours at room temperature, Reaction was quenched with at 0° C. with 0.15 mL of water. After 20 minutes, 0.15 mL of 15% NaOH was added. Finally, 0.45 mL of water was added and continued to stir at 0° C. for 20 minutes. White precipitate was filtered off and rinsed twice with 10 mL ethyl acetate each. Filtrate was concentrated to an oil. Oil was purified by flash chromatography (13:1) and eluted with 10-15% ethyl acetate in hexanes to give 161 mg of title compound. (73% yield).

Step 4: 2-Fluoro-6-[4-(2-fluorobenzyl)cyclohexylmethoxy]benzonitrile

In an 18 mL vial, sodium hydride was suspended in 2 mL dry dimethylformamide and chilled to 0° C. under nitrogen flow. 4-(2-Fluorobenzyl)cyclohexylmethanol (155 mg; 0.7 mmol) was added over 2 minutes and warmed to room temperature for 2 hours. Mixture was then added to a 0° C. mixture of 2,6-difluorobenzonitrile (97 mg; 0.7 mmol) in 2 mL of dimethylformamide over 1 minute and mixture continued to stir an additional 2 hours. Mixture was quenched over 10 g of ice and extracted 3× ethyl acetate 20 mL each. Combined organics were washed 5× water, brine and dried over MgSO$_4$. Colorless oil was obtained and purified by flash chromatography (20:1) with 0-5% ethyl acetate in hexanes to give 233 mg of title compound. (98% yield).

Step 5: 5-[4-(2-Fluorobenzyl)cyclohexylmethoxy] quinazoline-2,4-diamine

Cyclization of 2-fluoro-6-[4-(2-fluorobenzyl)cyclohexylmethoxy]benzonitrile (225 mg; 0.66 mmol) and guanidine carbonate (119 mg; 0.66 mmol) was carried out using Method F. Material was purified using ethyl alcohol trituration. Solids were collected by filtration. Title compound was obtained. (130 mg; 52% yield). $^1$HNMR (400 MHz, DMSO-$d_6$) δ 7.33 (t, J=8.0 Hz, 1H), 7.24 (m, 4H), 7.12 (m, 2H), 6.75 (dd, J=8.4, 0.8 Hz, 1H), 6.51 (d, J=7.6 Hz, 1H), 5.97 (br s, 2H), 3.92 (d, J=5.6 Hz, 2H), 2.52 (d, J=7.2 Hz, 2H), 1.83 (m, 3H), 1.69 (m, 2H), 1.51 (m, 1H), 1.06 (m, 4H). MS m/z (APCI) 381 (M+H)$^+$.

Example 155

5-[1-(2-Fluorophenyl)piperidin-4-ylmethoxy] quinazoline-2,4-diamine

Step 1: 1-(2-Fluorophenyl)piperidine-4-carboxylic Acid Ethyl Ester

Method A

1-Fluoro-2-iodobenzene (0.58 mL, 5.0 mmol) was added to a mixture of ethyl isonipecotate (1.2 mL, 7.5 mmol), potassium carbonate (1.4 g, 10 mmol), L-proline (0.12 g, 1 mmol) and copper iodide (0.095 g, 0.5 mmol) in 4 mL of dimethyl sulfoxide. Reaction stirred at 90° C. for 48 hours. The mixture was poured into a water (40 mL) solution and extracted with ethyl acetate (EtOAc) (4×10 mL). The combined organic layers were washed with brine (40 mL) and dried over anhydrous Na$_2$SO$_4$. The organic layer was concentrated in vacuo to obtain the crude mixture, which was purified by silica gel flash chromatography, using EtOAc/hexane (gradient system), to obtain 1-(2-fluorophenyl)piperidine-4-carboxylic acid ethyl ester (0.325 g, 26% yield).

Step 2: 1-(2-Fluorophenyl)piperidin-4-yl]methanol

Method B 1-(2-Fluorophenyl)piperidine-4-carboxylic acid ethyl ester (0.3 g, 1.2 mmol) was dissolved in 1.5 mL of methanol. Sodium borohydride (0.45 g, 12.0 mmol) was added in portionwise. The reaction was stirred for 4 days at room temperature. An additional 2.4 mmol of sodium borohydride was added to mixture and stirred at 40° C. After 18 hours, ammonium chloride (1.5 mL) was stirred cooling to room temperature for 30 minutes. The mixture was poured into a water (40 mL) solution and extracted with ethyl acetate (EtOAc) (4×10 mL). The combined organic layers were washed with brine (40 mL) and dried over anhydrous $Na_2SO_4$. The organic layer was concentrated in vacuo to obtain 1-(2-fluoro-phenyl)piperidin-4-yl]methanol (0.19 g, 76% yield).

Step 3: 2-Fluoro-6-[1-(2-fluorophenyl)piperidin-4-ylmethoxy]benzonitrile

Method C

To a cold (ice water) suspension of sodium hydride (0.044 g, 1.1 mmol) in anhydrous DMF (1 mL) is added a solution of 1-(2-fluorophenyl)piperidin-4-yl]methanol (0.19 g, 0.91 mmol) in anhydrous DWF (2 mL) over 11 minutes. After allowing to room temperature over 2 hours, this solution is added to a cold (ice water) stirred solution of 2,6-difluorobenzonitrile (0.14 g, 1.0 mmol) in anhydrous DMF (1 mL), and allowed to room temperature over 18 hours. The reaction mixture is poured into ice water with vigorous stirring and the resulting solid is filtered, washed with water, and dried under vacuum 1.5 hours to give 2-fluoro-6-[1-(2-fluorophenyl)piperidin-4-yloxy]benzonitrile (0.190 g, 63% yield).

Step 4: 5-[1-(2-Fluorophenyl)piperidin-4-ylmethoxy)quinazoline-2,4-diamine

Method D

2-Fluoro-6-[1-(2-fluorophenyl)piperidin-4-yloxy]benzonitrile (0.19 g, 0.58 mmol) and guanidine carbonate (0.12 mg, 0.64 mmol) were heated at 140° C. in dimethylacetamide for 4 hours, then cooled back to room temperature over 30 minutes. The reaction mixture was diluted with water, stirred for 45 minutes, filtered, triturated with ethanol, and filtered. Solids were dried to afford 70 milligrams of 5-[1-(2-fluorophenyl)piperidin-4-ylmethoxy)quinazoline-2,4-diamine (33% yield). $^1$HNMR (400 MHz, DMSO-$d_6$) δ 7.36 (t, J=8.4 Hz, 1H), 7.22 (s, 2H), 7.04-7.14 (m, 3H), 6.93-6.98 (m, 1H), 6.78 (d, J=8.4 Hz, 1H), 6.57 (d, J=7.6 Hz, 1H), 5.95 (s, 1H), 4.07 (d, J=6.0 Hz, 2H), 3.41 (d, J=12 Hz, 2H), 2.71 (t, J=11 Hz, 2H), 1.99-2.06 (m, 1H), 1.89 (d, J=12 Hz, 2H), 1.48-1.57 (m, 2H). MS m/z (APCI) 368 (M+H)$^+$.

Example 156

$^1$HNMR (400 MHz, DMSO-$d_6$) δ 7.90 (s, 1H), 7.85 (d, J=7.6 Hz, 1H), 7.58 (d, J=7.2 Hz, 1H), 7.48 (t, J=7.2 Hz, 1H), 7.34 (t, J=8.4 Hz, 1H), 7.20 (s, 2H), 6.77 (d, J=8.4 Hz, 1H), 6.54 (d, J=8.0 Hz, 1H), 5.95 (s, 2H), 3.99 (d, J=6.0 Hz, 2H), 3.86 (s, 3H), 3.54 (s, 2H), 2.84 (m, 2H), 1.99 (m, 2H), 1.88 (br s, 1H), 1.75 (d, J=12.8 Hz, 2H), 1.36 (m, 2H). MS m/z (ESI) 423 (M+H)$^+$.

Example 157

$^1$HNMR (400 MHz, DMSO-$d_6$) δ 7.92 (d, J=8.0 Hz, 2H), 7.46 (d, J=8.4 Hz, 2H), 7.34 (t, J=8.4 Hz, 1H), 7.19 (s, 2H), 6.76 (d, J=8.4 Hz, 1H), 6.53 (d, J=8.0 Hz, 1H), 5.93 (s, 2H), 4.00 (d, J=6.4 Hz, 2H), 3.84 (s, 3H), 3.55 (s, 2H), 2.84 (m, 2H), 1.99 (m, 2H), 1.89 (br s, 1H), 1.75 (m, 2H), 1.37 (m, 2H). MS m/z (ESI) 423 (M+H)$^+$.

Example 158

$^1$HNMR (400 MHz, DMSO-$d_6$) δ 7.35 (t, J=8.4 Hz, 1H), 7.28 (m, 2H), 7.02 (m, 3H), 6.78 (d, J=8.4 Hz, 1H), 6.55 (d, J=7.6 Hz, 1H), 6.04 (s, 2H), 3.98 (d, J=6.4 Hz, 2H), 3.43 (s, 1H), 2.79 (d, J=10.8 Hz, 2H) 2.34 (s, 6H), 2.08 (t, J=11.2 Hz, 2H), 1.88 (br s, 1H), 1.73 (m, 2H), 1.26 (m, 2H). MS m/z (ESI) 393 (M+H)$^+$.

Example 159

$^1$HNMR (400 MHz, DMSO-$d_6$) δ 7.37 (t, J=8.4 Hz, 1H), 7.26 (m, 2H), 6.79 (d, J=8.4 Hz, 1H), 6.58 (d, J=8.0 Hz, 1H), 6.13 (tt, J=56, 4.4 Hz, 1H), 6.09 (s, 2H), 4.00 (d, J=6.4 Hz, 2H), 2.94 (m, 2H), 2.71 (d, J=16, 4.4 Hz, 2H), 2.18 (t, J=9.6 Hz, 2H), 1.87 (br s, 1H), 1.74 (m, 2H), 1.35 (m, 2H). MS m/z (ESI) 339 (M+H)$^+$.

Example 160

5-[1-(2-Fluoro-6-trifluoromethylbenzyl)piperidin-4-ylmethoxy]quinazoline-2,4-diamine. $^1$HNMR (400 MHz, DMSO-$d_6$) δ 7.52-7.62 (m, 4H), 7.38-7.42 (m, 2H), 6.81 (d, J=8.4 Hz, 1H), 6.62 (d, J=7.6 Hz, 1H), 6.31 (s, 2H), 3.99 (d, J=6.4 Hz, 2H), 3.61 (s, 2H), 2.79 (d, J=10.8 Hz, 2H), 2.09 (t, J=11 Hz, 2H), 1.90 (b, 1H), 1.73 (d, J=12 Hz, 2H), 1.20-1.29 (m, 2H). MS m/z (ESI) 450 (M+H)$^+$ Example 161

5-[1-(2-Chloro-6-fluorobenzyl)piperidin-4-ylmethoxy]quinazoline-2,4-diamine. $^1$HNMR (400 MHz, DMSO-$d_6$) δ 7.56 (b, 1H) 7.32-7.43 (m, 4H), 7.21 (t, J=8.6 Hz, 2H), 6.81 (d, J=8.4 Hz, 1H), 6.62 (d, J=8.4 Hz, 1H), 6.34 (s, 2H), 3.95 (d, J=6.4 Hz, 2H), 3.60 (s, 2H), 2.86 (d, J=11.2 Hz, 2H), 2.14 (t, J=4.4 Hz, 2H), 1.91 (b, 1H), 1.73 (d, J=11.6 Hz, 2H), 1.23-1.89 (m, 2H). MS m/z (ESI) 416 (M+H)$^+$ Example 162

5-[4-(2,6-Difluorophenoxy)cyclohexylmethoxy]-quinazoline-2,4-diamine

Step 1: 4-Hydroxycyclohexanecarboxylic Acid Ethyl Ester

4-Hydroxycyclohexane carboxylic acid (5 g, 34.5 mmol) was heated to reflux for 16 hours in the presence of 50 mL of ethyl alcohol and 2 mL of sulfuric acid. Reaction volume was reduce by half at reduced pressure and mixture was poured into sat. $Na_2CO_3$. Mixture was extracted 3×50 mL of ethyl acetate and combined organics were washed with brine and dried over $MgSO_4$. Title compound was obtained as a colorless crude oil. (5.9 g; 100% yield).

Step 2: 4-(2,6-Difluorophenoxy)cyclohexanecarboxylic Acid Ethyl Ester

4-Hydroxycyclohexanecarboxylic acid ethyl ester (300 mg; 1.7 mmol), triphenylphosphine (1 g; 4.2 mmol) and 2,6-difluorophenol (340 mg; 2.6 mmol) were stirred in anhydrous toluene and chilled to 0° C. under nitrogen flow. Diethyl azodicarboxylate (2 mL; 4.3 mmol) was added to the mixture over 1 minute and warmed to room temperature. Reaction continued for 16 hours. Reaction was quenched with water, and mixture was extracted with 4×5 mL with ethyl acetate.

Combined organics were washed with brine and dried over MgSO$_4$. Oily residue was triturated with diethyl ether and solids filtered off. Filtrate was concentrated at reduced pressure and purified via flash chromatography using 5-20% ethyl acetate in hexanes to give 162 mg of title compound. (34% yield).

Step 3: [4-(2,6-Difluorophenoxy)cyclohexyl]methanol 4-(2,6-Difluorophenoxy)cyclohexanecarboxylic acid ethyl ester (155 mg, 0.55 mmol) was carried out using Method H with lithium aluminum hydride (150 mg; 3.95 mmol) in tetrahydrofuran at 0° C. under nitrogen flow. Material was purified by flash chromatography using 2% methanol in dichloromethane to give 109 mgs of title compound. (82% yield).

Step 4: 2-[4-(2,6-Difluorophenoxy)cyclohexyl methoxy]-6-fluorobenzonitrile (Method I)

4-(2,6-Difluorophenoxy)cyclohexylmethanol (100 mg; 0.4 mmol) and 2,6-difluorobenzonitrile were combined in 3 mL of dimethylformamide under nitrogen flow and chilled to 0° C. Potassium t-butoxide (56 mg; 1.2 mmol) was added in portions. Mixture warmed to room temperature. After 4 hours reaction was quenched with 3 mL of water and mixture was extracted with 3×8 mL of ethyl acetate. Combined organics were washed with 5×8 mL of water, once with brine and dried over MgSO$_4$. Crude oil was purified via flash chromatography using 0-20% ethyl acetate in hexanes to give 95 mgs of title compound. (66% yield).

Step 5: 5-[4-(2,6-Difluorophenoxy)cyclohexyl methoxy]quinazoline-2,4-diamine

Cyclization of 2-[4-(2,6-difluorophenoxy)cyclohexyl-methoxy]-6-fluorobenzonitrile was carried out using Method F (95 mg; 0.26 mmol) and guanidine carbonate (43 mg; 0.26 mmol) in 1.5 mL of dimethylacetamide. Material was purified using C18 reverse phase silica and 0-100% acetonitrile in water gradient to give 9 mg of title compound. (9% yield. $^1$HNMR (400 MHz, DMSO-d$_6$) δ 7.37 (m, 1H), 7.14 (m, 5H), 6.77 (m, 1H), 6.51 (m, 1H), 5.96 (br s, 2H), 5.7 (s, 1H), 4.02 (m, 3H), 2.02 (m, 4H), 1.62 (m, 4H). MS m/z (ESI) 401 (M+H)$^+$.

Example 163

5-[1-(2-Chlorophenyl)piperidin-4-ylmethoxy] quinazoline-2,4-diamine

Step 1: 1-(2-Chlorophenyl)piperidine-4-carboxylic Acid Ethyl Ester

1-Chloro-2-iodobenzene (0.63 mL, 5.0 mmol) was reacted via Method A to yield 1-(2-chlorophenyl)piperidine-4-carboxylic acid ethyl ester (0.32 g, 24% yield).

Step 2: 1-(2-Chlorophenyl)piperidin-4-yl]methanol

Method E 1-(2-Chlorophenyl)piperidine-4-carboxylic acid ethyl ester (0.32 g, 1.2 mmol) in 6.9 mL of tetrahydrofuran was added dropwise to a suspension of lithium aluminum hydride (0.5 g, 13 mmol) in 6.9 mL of tetrahydrofuran at 0° C. Reaction was stirred for three hours. Reaction was quenched with 0.5 mL water for 20 minutes, 0.5 mL 15% sodium hydroxide for 20 minutes, and 1.5 mL water for 20 minutes. Mixture was diluted with 15 mL of ethyl acetate for 30 minutes. Mixture was filtered and organic layer was concentrated in vacuo to produce 1-(2-chlorophenyl)piperidin-4-yl]methanol (0.2 g, 74% yield).

Step 3: 2-[1-(2-Chlorophenyl)piperidin-4-yl-methoxy]-6-fluorobenzonitrile

To a cold (ice water) suspension of sodium hydride (0.043 g; 1.1 mmol) in anhydrous DMF (1 mL) is added a solution of 1-(2-chloro-phenyl)-piperidin-4-yl]methanol (0.20 g; 0.89 mmol) in anhydrous DMF (2 mL) over 11 minutes. After allowing to room temperature over 2 hours, this solution is added to a cold (ice water) stirred solution of 2,6-difluorobenzonitrile (0.14 g; 0.97 mmol) in anhydrous DMF (1 mL), and allowed to room temperature over 18 hours. The mixture was poured into a water (40 mL) solution and extracted with ethyl acetate (EtOAc) (4×10 mL). The combined organic layers were washed with brine (40 mL) and dried over anhydrous Na$_2$SO$_4$. The organic layer was concentrated in vacuo to obtain 2-[1-(2-chlorophenyl)piperidin-4-ylmethoxy]-6-fluorobenzonitrile (0.280 g, 78% yield).

Step 4: 5-[1-(2-Chlorophenyl)piperidin-4-yl-methoxy)quinazoline-2,4-diamine

2-[1-(2-Chlorophenyl)piperidin-4-ylmethoxy]-6-fluorobenzonitrile (0.28 g; 0.81 mmol) and guanidine carbonate (0.293 mg; 1.6 mmol) were heated at 140° C. in dimethylacetamide for 2 days, then cooled back to room temperature. The reaction mixture was diluted with water, stirred for 45 minutes, filtered, triturated with ethanol, and filtered. Solids were dried to afford 90 milligrams of 5-[1-(2-chlorophenyl)-piperidin-4-ylmethoxy)quinazoline-2,4-diamine (29% yield).
$^1$HNMR (400 MHz, DMSO-d$_6$) δ 7.16-7.41 (m, 4H), 7.22 (t, J=6.8 Hz, 1H), 6.78 (d, J=8.8 Hz, 1H), 6.58 (d, J=7.6 Hz, 1H), 5.94 (s, 2H), 4.09 (d, J=6.4 Hz, 2H), 3.33 (s, 2H), 2.70 (t, J=10.6 Hz, 2H), 2.08 (b, 1H), 1.9 (d, J=10.4 Hz, 2H), 1.52-1.55 (m, 2H). MS m/z (ESI) 384 (M+H)$^+$.

Example 164

5-[4-(2-Chlorobenzyl)cyclohexylmethoxy]quinazoline-2,4-diamine

Step 1: 4-(2-Chlorobenzyl)cyclohexanecarboxylic Acid

Trans-4-(2-chlorobenzoyl)cyclohexane-1-carboxylic acid (300 mg; 1.12 mmol) and triethylsilane (654 mg; 5.62 mmol) was carried out using Method G in 4 mL of trifluoroacetic acid. Title compound was obtained as a white solid. (118 mg; 42% yield).

Step 2: 4-(2-Chlorobenzyl)cyclohexylmethanol 4-(2-Chlorobenzyl)cyclohexanecarboxylic acid (115 mg; 0.48 mmol) and lithium aluminum hydride (100 mg; 2.64 mmol) was carried out using Method H in 5 mL tetrahydrofuran. Material was purified by flash chromatography using 10-50% ethyl acetate in hexanes gradient to give 73 mgs of title compound. (67% yield).

Step 3: 2-[4-(2-Chlorobenzyl)cyclohexylmethoxy]-6-fluorobenzonitrile 4-(2-Chlorobenzyl)cyclohexylmethanol (68 mg; 0.28 mmol) and 2,6-difluorobenzonitrile (40 mg; 0.28 mmol) were carried out using Method I with potassium t-butoxide (35 mg; 0.31 mmol) in 1.5 mL of dimethylformamide. Material was purified by flash chromatography to give 100 mgs of title compound as a colorless oil. (100% yield).

Step 4: 5-[4-(2-Chlorobenzyl)cyclohexylmethoxy]quinazoline-2,4-diamine

Cyclization of 2-[4-(2-chlorobenzyl)cyclohexylmethoxy]-6-fluorobenzonitrile (100 mg; 0.28 mmol) was carried out using Method F using guanidine carbonate (100 mg; 0.55 mmol) in 1.5 mL of dimethylacetamide. Title compound was obtained as a white solid. (88 mg; 79% yield). $^1$HNMR (400 MHz, DMSO-$d_6$) δ 7.27 (m, 7H), 6.75 (d, J=8.0 Hz, 1H), 6.50 (d, J=7.6 Hz, 1H), 5.97 (br s, 2H), 3.92 (d, J=5.6 Hz, 2H), 2.52 (d, J=7.2 Hz, 2H), 1.83 (m, 3H), 1.68 (m, 3H), 1.06 (m, 4H). MS m/z (ESI) 398 (M+H)$^+$.

Example 165

$^1$HNMR (400 MHz, DMSO-$d_6$) δ 7.37 (t, J=8.4 Hz, 1H), 7.30 (m, 2H), 6.79 (d, J=8.0 Hz, 1H), 6.58 (d, J=7.6 Hz, 1H), 6.11 (s, 2H), 4.00 (d, J=6.4 Hz, 2H), 2.96 (m, 2H), 2.37 (m, 2H), 1.86 (br s, 1H), 1.74 (m, 2H), 1.35 (m, 2H). MS m/z (ESI) 357 (M+H)$^+$.

Example 166

5-[1-(4-Trifluoromethylphenyl)piperidin-4-ylmethoxy]quinazoline-2,4-diamine

Step 1: [1-(4-Trifluoromethylphenyl)piperidin-4-yl]methanol 1-(4-Trifluoromethylphenyl)piperidine-4-carboxylic acid ethyl ester (0.35 g, 1.2 mmol) was reacted via Method E to produce 280 milligrams of [1-(4-trifluoromethylphenyl)-piperidin-4-yl]methanol (93% yield).

Step 2: 2-Fluoro-6-[1-(4-trifluoromethylphenyl)piperidin-4-ylmethoxy]benzonitrile

[1-(4-Trifluoromethylphenyl)piperidin-4-yl]methanol (0.28 g, 1.1 mmol) was reacted via Method C to produce 250 milligrams of 2-fluoro-6-[1-(4-trifluoromethylphenyl)piperidin-4-ylmethoxy]benzonitrile (61% yield).

Step 3: 5-[1-(4-Trifluoromethylphenyl)piperidin-4-ylmethoxy]quinazoline-2,4-diamine 2-Fluoro-6-[1-(4-trifluoromethylphenyl)piperidin-4-ylmethoxy]benzonitrile (0.11 g, 0.29 mmol) was reacted via Method D for 6 hours and produced 100 milligrams of 5-[1-(4-trifluoromethylphenyl)piperidin-4-ylmethoxy]quinazoline-2,4-diamine (83%). $^1$HNMR (400 MHz, DMSO-$d_6$) δ 7.48 (d, J=8.4 Hz, 2H), 7.35 (t, J=8 Hz, 1H), 7.19 (s, 2H), 7.07 (d, J=9.2 Hz, 2H), 6.77 (d, J=8.0 Hz, 1H), 6.55 (d, J=8.0 Hz, 1H), 5.95 (s, 2H), 4.04 (d, J=6.4 Hz, 2H), 3.94 (d, J=12.8 Hz, 2H), 2.86 (t, J=11.4 Hz, 2H), 2.16 (b, 1H), 1.87 (d, J=12 Hz, 2H), 1.36-1.45 (m, 2H). MS m/z (ESI) 419 (M+H)$^+$.

Example 167

5-[4-(4-Chlorophenyl)cyclohexylmethoxy]quinazoline-2,4-diamine

Step 1: [4-(4-Chlorophenyl)cyclohexyl]methanol 4-(4-Chlorophenyl)cyclohexane carboxylic acid (0.35 g, 1.5 mmol) was reacted via Method E over 72 hours. The solid was poured into a water (40 mL) solution and extracted with ethyl acetate (EtOAc) (4×10 mL). The combined organic layers were washed with brine (40 mL) and dried over anhydrous Na$_2$SO$_4$. The organic layer was concentrated in vacuo to obtain [4-(4-chlorophenyl)cyclohexyl]methanol (0.210 g, 64% yield).

Step 2: 2-[4-(4-Chlorophenyl)cyclohexylmethoxy]-6-fluorobenzonitrile

[4-(4-Chlorophenyl)cyclohexyl]methanol (0.21 g, 0.93 mmol) was reacted via Method C to yield 150 milligrams of 2-[4-(4-chlorophenyl)cyclohexylmethoxy]-6-fluoro-benzonitrile (47% yield).

Step 3: 5-[4-(4-Chlorophenyl)cyclohexylmethoxy]quinazoline-2,4-diamine

2-[4-(4-Chlorophenyl)cyclohexylmethoxy]-6-fluorobenzonitrile (0.075 g, 0.22 mmol) was reacted via Method D to produce 65 milligrams of 5-[4-(4-chlorophenyl)cyclohexylmethoxy]quinazoline-2,4-diamine (78%).
$^1$HNMR (400 MHz, DMSO-$d_6$) δ 7.22-7.35 (m, 7H), 6.78 (d, J=6.8 Hz, 1H), 6.56 (d, J=6.4 Hz, 1H), 5.94 (s, 2H), 4.00 (d, J=3.6 Hz, 2H), 1.84-1.97 (m, 5H), 1.46-1.52 (m, 2H), 1.23-1.28 (m, 3H). MS m/z (ESI) 384 (M+H)$^+$.

Example 168

5-[4-(2-Methoxybenzyl)-cyclohexylmethoxy]quinazoline-2,4-diamine

Step 1: 4-(2-Methoxybenzoyl)cyclohexanecarboxylic Acid Methyl Ester

In an oven dried 1 neck round bottom flask with reflux condenser and stirbar, trans-4-carbomethoxycyclohexane-1-carboxylic acid (1.11 g; 5.4 mmol) was heated to reflux in the presence of 30 mL thionyl chloride. After 3 hours reflux, mixture cooled to 40° C. under nitrogen flow, and excess thionyl chloride was removed at reduced pressure. Residue was taken up in 5 mL of dry tetrahydrofuran and added to a 0° C. mixture of 2-methoxyphenylzinc iodide (11.0 mL; 5.4 mmol), tetrakis(triphenylphospine)palladium (0) (90 mg; 0.08 mmol) in 2.5 mL anhydrous tetrahydrofuran. Mixture was allowed to warm to room temperature over 16 hours. Reaction was quenched with 6 mL 1N HCl and ethyl acetate was taken in. Organics separated and aqueous re-extracted with 20 mL ethyl acetate. Combined organics were washed with sat. NaHCO$_3$, water, brine and dried over MgSO$_4$. Material was purified via flash silica plug (10:1) using 15% ethyl acetate in hexanes isocratic to give 900 mg of title compound. (64% yield)

Step 2: 4-(2-Methoxybenzyl)cyclohexanecarboxylic Acid Methyl Ester

In a 100 mL flask with stir bar and 4-(2-methoxybenzoyl)cyclohexanecarboxylic acid methyl ester (900 mg; 3.26 mmol), trifluoroacetic acid (10 mL) was chilled to 0° C. and triethylsilane (2 g; 16.3 mmol) was added over 1 minute. Mixture was allowed to warm to room temperature. After 48 hours, mixture was concentrated in vacuo and reduced by half volume. The mixture was poured into a water (40 mL) solution and extracted with ethyl acetate (EtOAc) (4×10 mL). The combined organic layers were washed with NaHCO$_3$ (40 mL), brine (40 mL) and dried over anhydrous Na$_2$SO$_4$. The organic layer was concentrated in vacuo to obtain the crude mixture, which was purified by of silica gel flash chromatography, using EtOAc/hexane (gradient system), to obtain 4-(2-methoxybenzyl)cyclohexanecarboxylic acid methyl ester (0.78 g, 91% yield).

Step 3: [4-(2-Methoxybenzyl)cyclohexyl]methanol 4-(2-Methoxybenzyl)cyclohexanecarboxylic acid methyl ester (0.78 g, 3.0 mmol) was reacted via Method E to produce 210 milligrams of [4-(2-methoxybenzyl)cyclohexyl]methanol (30% yield).

Step 4: 2-Fluoro-6-[4-(2-methoxybenzyl)cyclohexylmethoxy]benzonitrile

To a cold (ice water) suspension of sodium hydride (0.043 g; 1.1 mmol) in anhydrous DMF (1.4 mL) is added a solution of [4-(2-methoxybenzyl)cyclohexyl]methanol (0.21 g, 0.9 mmol) in anhydrous DMF (1.4 mL) over 11 minutes. After allowing to room temperature over 2 hours, this solution is added to a cold (ice water) stirred solution of 2,6-difluorobenzonitrile (0.14 g; 0.99 mmol) in anhydrous DMF (1.4 mL), and allowed to room temperature over 18 hours. The mixture was poured into a water (40 mL) solution and extracted with ethyl acetate (EtOAc) (4×10 mL). The combined organic layers were washed with brine (40 mL) and dried over anhydrous Na$_2$SO$_4$. The organic layer was concentrated in vacuo to purify by of silica gel flash chromatography, using EtOAc/hexane (gradient system), to obtain 2-fluoro-6-[4-(2-methoxybenzyl)cyclohexylmethoxy]benzonitrile (0.09 g, 28% yield).

Step 5: 5-[4-(2-Methoxybenzyl)cyclohexylmethoxy]quinazoline-2,4-diamine

2-Fluoro-6-[4-(2-methoxybenzyl)cyclohexylmethoxy]benzonitrile (0.09 g, 0.3 mmol) was reacted via Method D to produce 27 milligrams of 5-[4-(2-methoxybenzyl)cyclohexylmethoxy]quinazoline-2,4-diamine (23%).
$^1$HNMR (400 MHz, DMSO-d$_6$) δ 7.33 (t, J=8.2 Hz, 1H), 7.15-7.18 (m, 3H), 7.06-7.08 (m, 1H), 6.93 (d, J=8.4 Hz, 1H), 6.84 (t, J=7.4 Hz, 1H), 6.75 (d, J=8.0 Hz, 1H), 6.50 (d, J=8.0 Hz, 1H), 5.93 (s, 2H), 3.92 (d, J=5.6 Hz, 2H), 3.77 (s, 3H), 2.47 (d, J=6.8 Hz, 2H), 1.81 (b, 2H), 1.68 (b, 2H), 1.5 (b, 1H), 1.23 (s, 1H), 1.01-1.04 (m, 4H). MS m/z (ESI) 394 (M+H)$^+$.

4-(2-Cyano-3-fluorophenyl)piperazine-1-carboxylic acid tert-butyl ester. In a round bottom flask, sodium hydride (60%) (2.40 g; 60 mmol) was suspended in DMF (25 mL) and cooled in an ice water bath under nitrogen. 1-Boc-piperazine (9.53 g; 50.6 mmol) was added in small portions to the reaction mixture at 0° C. over 30 minutes. The mixture was allowed to stir at room temperature for 3 hours and the recooled to 0° C. 2,6-Difluorobenzonitrile (8.57 g; 60 mmol) was added to the reaction mixture in DMF (10 mL) over 45 minutes. The mixture was stirred at room temperature for 16 hours. The reaction mixture was poured in ice water (250 mL) and stirred. The solid was collected by vacuum filtration and washed with water. And then dried under vacuum to yield the title compound (11.65 g; 75% yield).

Example 219

4-(2,4-Diaminoquinazolin-5-yl)piperazine-1-carboxylic acid tert-butyl ester (Method A). In a reaction vessel, 4-(2-cyano-3-fluorophenyl)piperazine-1-carboxylic acid tert-butyl ester (613.7 mg; 2 mmol) and guanidine carbonate (360.6 mg; 2 mmol) were suspended in 2 mL DMA. The reaction mixture was heated to 145° C. for 22 hours. The mixture was cooled to room temperature and 4 mL of water was added and stirred for 15 minutes. The solid was collected by vacuum filtration and washed with water and ethyl acetate and dried under vacuum to yield 278.4 mg (40% yield) of the title compound.

Example 220

5-piperazin-1-ylquinazoline-2,4-diamine. In a reaction vessel, 4-(2,4-diaminoquinazolin-5-yl)piperazine-1-carboxylic acid tert-butyl ester (102.8 mg; 0.3 mmol) was stirred in methanol (2 mL) and 2 N HCl in ether was added (0.7 mL). The reaction mixture was stirred at room temperature for 4 days. The solid was collected by vacuum filtration and washed with methanol to give 45 mg of the title compound as the HCl salt (54% yield). To form the free base, the HCl salt (3.66 g; 13 mmol) was dissolved in water (20 mL) and 1 M NaOH (10 mL) was added to the reaction mixture. The mixture was stirred for 4 hours at room temperature. The solvent was removed in vacuo and the solid was stirred in brine solution and solid collected by vacuum filtration to yield 192 mg of the title compound (68% yield).

Reaction with benzoyl chlorides or sulfonyl chlorides. In an 8 mL vial, PS-NMM (200 mg, 0.4 mmol) was swelled in dry DMF (4 mL) and 5-piperazin-1-ylquinazoline-2,4-diamine (50 mg; 0.2 mmol) was added to the vial. The benzoyl chloride or sulfonyl chloride (0.41 mmol) was added and the vial was placed on a shaker for 16 hours. PS-Trisamine (112 mg; 0.4 mmol) was added and shaken for 2 hours. The resin was collected by vacuum filtration and the solvent was removed in vacuo from the filtrates. Ethanol/1 N NaOH (2.1) was shaken with the material and the solid was collected by vacuum filtration and dried under vacuum to yield the desired products.

Reaction with benzyl chlorides or bromides. Same procedure as above except heating at 47° C. for 96 hours on the shaker and solids triturated with ethanol only.

Example 169

5-(4-Benzyl-piperazin-1-yl)-quinazoline-2,4-diamine

In a 20 mL vial with stir bar, triethylamine (40 mg; 0.4 mmol) was added to a mixture of 5-piperazin-1-yl-quinazoline-2,4-diamine (50 mg; 0.2 mmol) and benzyl bromide (45 mg; 0.27 mmol) in N,N-dimethylformamide and heated to 60° C. for 16 hours. Mixture was quenched with 1 mL of 1N NaOH and after 1.5 hours solids were collected by filtration and triturated with ethanol to obtain 43.1 mg of title compound. (64% yield).
$^1$H NMR (400 MHz, DMSO-d$_6$) δ 8.89 (d, J=3.6 Hz, 1H), 7.35 (m, 5H), 7.22 (m, 2H), 6.96 (d, J=8.4 Hz, 1H), 6.86 (d, J=7.6 Hz, 1H), 5.93 (br s, 2H), 3.55 (s, 2H), 2.99 (d, J=11.6 Hz, 2H), 2.83 (m, 4H), 2.26 (q, J=11.2, 9.2 Hz, 2H).
ESIMS+334.6 m/z

Example 170

5-[4-(2-Methyl-benzyl)-piperazin-1-yl]-quinazoline-2,4-diamine (Resin Method)

5-piperazin-1-yl-quinazoline-2,4-diamine (50 mg; 0.2 mmol) was shaken for 96 hours at 47° C. in the presence of 3-(Morphonlino)propyl polystyrene sulfonamide (PS-NMM) (160 mg; 0.4 mmol) and o-methylbenzyl bromide (68.5 mg; 0.37 mmol) in 4 mL N,N-dimethylformamide. Tris-(2-aminoethyl)aminomethyl polystyrene (PS-Trisamine) (112 mg; 0.4 mmol) was then added to the mixture and continued to shake for an additional 2 hours. Resins were filtered off and rinsed with methanol. Filtrate was concentrated at reduced pressure, and residue was triturated 1N NaOH with ethanol. Solids were collected by filtration to yield 47.9 mg of title compound. (69% yield).
$^1$H NMR (400 MHz, DMSO-$d_6$) δ 12.3 (s, 1H), 10.1 (s, 1H), 9.0 (s, 1H), 7.71 (t, J=8.0 Hz, 2H), 7.21 (m, 6H), 3.53 (s, 2H), 3.03 (br d, J=10.8 Hz, 2H), 2.89 (m, 4H), 2.36 (m, 5H). ESIMS+349.7 m/z

Example 171

5-[4-(2-Chloro-benzyl)-piperazin-1-yl]-quinazoline-2,4-diamine

Title compound was prepared via Resin Method using 5-piperazin-1-yl-quinazoline-2,4-diamine (50 mg; 0.2 mmol) and 2-Chlorobenzyl bromide (76 mg; 0.37 mmol) to obtain 46.6 mg. (63% yield). $^1$H NMR (400 MHz, DMSO-$d_6$) δ 12.4 (s, 1H), 10.1 (s, 1H), 9.0 (s, 1H), 7.72 (t, J=8.0 Hz, 2H), 7.52 (m, 1H), 7.45 (m, 1H), 7.34 (m, 3H), 7.22 (d, J=8.0 Hz, 1H), 3.68 (s, 2H), 3.03 (br d, J=10.8 Hz, 2H), 2.93 (m, 4H), 2.41 (m, 2H).
ESIMS+369.2 m/z

Example 172

5-[4-(3-Chloro-benzyl)-piperazin-1-yl]-quinazoline-2,4-diamine

Title compound was prepared via Resin Method using 5-piperazin-1-yl-quinazoline-2,4-diamine (50 mg; 0.2 mmol) and 3-Chlorobenzyl bromide (76 mg; 0.37 mmol) to obtain 49.5 mg. (67% yield). $^1$H NMR (400 MHz, DMSO-$d_6$) δ 12.4 (s, 1H), 10.0 (s, 1H), 9.0 (s, 1H), 7.72 (m, 2H), 7.34 (m, 4H), 7.22 (d, J=8.0 Hz, 1H), 3.59 (s, 2H), 3.03 (br d, J=10.8 Hz, 2H), 2.90 (m, 4H), 2.31 (m, 2H). ESIMS+369.2 m/z

Example 173

5-[4-(4-Chloro-benzyl)-piperazin-1-yl]-quinazoline-2,4-diamine

Title compound was prepared via Resin Method using 5-piperazin-1-yl-quinazoline-2,4-diamine (50 mg; 0.2 mmol) and 4-Chlorobenzyl Chloride (59.6 mg; 0.37 mmol) to obtain 49.5 mg. (67% yield). $^1$H NMR (400 MHz, DMSO-$d_6$) δ 12.8 (s, 1H), 9.94 (s, 1H), 8.88 (s, 1H), 7.69 (m, 2H), 7.38 (m, 4H), 7.25 (d, J=8.0 Hz, 1H), 7.21 (d, J=8.4 Hz, 1H), 3.57 (s, 2H), 3.03 (br d, J=10.8 Hz, 3H), 2.91 (m, 3H), 2.29 (m, 2H). ESIMS+369.2 m/z

Example 174

5-[4-(2,4-Dichloro-benzyl)-piperazin-1-yl]-quinazoline-2,4-diamine

Title compound was prepared via Resin Method using 5-piperazin-1-yl-quinazoline-2,4-diamine (50 mg; 0.2 mmol) and 2,4-Dichlorobenzyl Chloride (72.3 mg; 0.37 mmol) to obtain 48.3 mg. (60% yield). $^1$H NMR (400 MHz, DMSO-$d_6$) δ 9.71 (s, 1H), 8.49 (s, 1H), 7.60 (m, 3H), 7.44 (m, 1H), 7.16 (m, 2H), 3.66 (s, 2H), 3.02 (br d, J=10.8 Hz, 3H), 2.90 (m, 4H), 2.41 (m, 2H). ESIMS+403.5 m/z

Example 175

5-[4-(3,4-Dichloro-benzyl)-piperazin-1-yl]-quinazoline-2,4-diamine

Title compound was prepared via Resin Method using 5-piperazin-1-yl-quinazoline-2,4-diamine (50 mg; 0.2 mmol) and 3,4-Dichlorobenzyl Chloride (72.3 mg; 0.37 mmol) to obtain 55.8 mg. (69% yield). $^1$H NMR (400 MHz, DMSO-$d_6$) δ 9.70 (s, 1H), 8.50 (s, 1H), 7.61 (m, 3H), 7.35 (dd, J=8.4, 1.4 Hz, 1H), 7.16 (m, 4H), 3.59 (s, 2H), 3.02 (br d, J=10.8 Hz, 3H), 2.90 (m, 3H), 2.31 (m, 2H). ESIMS+403.5 m/z

Example 176

5-[4-(2-Fluoro-benzyl)-piperazin-1-yl]-quinazoline-2,4-diamine

Title compound was prepared via Resin Method using 5-piperazin-1-yl-quinazoline-2,4-diamine (50 mg; 0.2 mmol) and 2-fluorobenzyl bromide (69.9 mg; 0.37 mmol) to obtain 35.3 mg. (50% yield). $^1$H NMR (400 MHz, DMSO-$d_6$) δ 12.5 (s, 1H), 10.0 (s, 1H), 8.99 (s, 1H), 7.72 (m, 2H), 7.46 (t, J=6.8 Hz, 1H), 7.33 (m, 5H), 3.64 (s, 2H), 3.03 (br d, J=10.8 Hz, 3H), 2.91 (m, 3H), 2.34 (m, 2H). ESIMS+353.6 m/z

Example 177

5-[4-(2,4-Difluoro-benzyl)-piperazin-1-yl]-quinazoline-2,4-diamine

Title compound was prepared via Resin Method using 5-piperazin-1-yl-quinazoline-2,4-diamine (50 mg; 0.2 mmol) and 2,4-Difluorobenzyl bromide (76.6 mg; 0.37 mmol) to obtain 65 mg. (88% yield). $^1$H NMR (400 MHz, DMSO-$d_6$) δ 9.95 (s, 1H), 8.87 (s, 1H), 7.67 (m, 3H), 7.48 (m, 1H), 7.24 (m, 3H), 7.09 (m, 1H), 3.61 (s, 2H), 3.02 (br d, J=10.8 Hz, 2H), 2.89 (m, 4H), 2.33 (m, 2H). ESIMS+371.5 m/z

Example 178

5-[4-(2-Trifluoromethoxy-benzyl)-piperazin-1-yl]-quinazoline-2,4-diamine

Title compound was prepared via Resin Method using 5-piperazin-1-yl-quinazoline-2,4-diamine (50 mg; 0.2 mmol) and 2-(trifluoromethoxy)benzyl bromide (94.4 mg; 0.37 mmol) to obtain 45.5 mg. (54% yield). $^1$H NMR (400 MHz, DMSO-$d_6$) δ 12.4 (br s, 1H), 10.0 (br s, 1H), 8.94 (br s, 1H), 7.69 (m, 3H), 7.42 (m, 3H), 7.27 (d, J=7.6 Hz, 1H), 7.23

(d, J=8.4 Hz, 1H), 3.65 (s, 2H), 3.04 (d, J=10.4 Hz, 2H), 2.89 (m, 4H), 2.36 (t, J=11.2 Hz, 2H). ESIMS+419.5 m/z

Example 179

5-[4-(4-Trifluoromethoxy-benzyl)-piperazin-1-yl]-quinazoline-2,4-diamine

Title compound was prepared via Resin Method using 5-piperazin-1-yl-quinazoline-2,4-diamine (50 mg; 0.2 mmol) and 4-(trifluoromethoxy)benzyl bromide (94.4 mg; 0.37 mmol) to obtain 17.2 mg. (21% yield). $^1$H NMR (400 MHz, DMSO-$d_6$) δ 12.6 (br s, 1H), 10.0 (br s, 1H), 9.01 (br s, 1H), 7.72 (m, 2H), 7.47 (m, 2H), 7.28 (m, 4H), 3.60 (s, 2H), 3.04 (d, J=10.4 Hz, 2H), 2.89 (m, 4H), 2.36 (m, 2H). ESIMS+ 419.8 m/z

Example 180

5-[4-(3-Trifluoromethoxy-benzyl)-piperazin-1-yl]-quinazoline-2,4-diamine

Title compound was prepared via Resin Method using 5-piperazin-1-yl-quinazoline-2,4-diamine (50 mg; 0.2 mmol) and 3-(trifluoromethoxy)benzyl bromide (94.4 mg; 0.37 mmol) to obtain 58.9 mg. (70% yield). $^1$H NMR (400 MHz, DMSO-$d_6$) δ 10.0 (br s, 1H), 8.97 (br s, 1H), 7.72 (m, 2H), 7.50 (m, 2H), 7.28 (m, 1H), 7.29 (m, 4H), 3.64 (s, 2H), 3.04 (d, J=10.4 Hz, 2H), 2.93 (m, 4H), 2.32 (m, 2H). ESIMS+ 419.8 m/z

Example 181

5-(4-Naphthalen-1-ylmethyl-piperazin-1-yl)-quinazoline-2,4-diamine

Title compound was prepared via Resin Method using 5-piperazin-1-yl-quinazoline-2,4-diamine (50 mg; 0.2 mmol) and 1-(chloromethyl)naphthalene (65.4 mg; 0.37 mmol) to obtain 44.7 mg. (58% yield). $^1$H NMR (400 MHz, DMSO-$d_6$) δ 10.0 (br s, 1H), 8.95 (br s, 1H), 8.30 (d, J=8.4 Hz, 1H), 7.92 (m, 2H), 7.69 (m, 1H), 7.55 (m, 1H), 7.49 (m, 5H), 7.23 (d, J=8.0 Hz, 1H), 7.19 (d, J=8.0 Hz, 1H), 3.99 (s, 2H), 3.0 (m, 6H), 2.38 (m, 2H). ESIMS+385.7 m/z

Example 182

5-(4-Benzo[1,3]dioxol-5-ylmethyl-piperazin-1-yl)-quinazoline-2,4-diamine

Title compound was prepared via Resin Method using 5-piperazin-1-yl-quinazoline-2,4-diamine (50 mg; 0.2 mmol) and 3,4-methylenedioxybenzyl chloride (63.1 mg; 0.37 mmol) to obtain 37.5 mg. (50% yield). $^1$H NMR (400 MHz, DMSO-$d_6$) δ 9.34 (s, 1H), 7.92 (s, 1H), 7.51 (t, J=8.0 Hz, 1H), 7.04 (m, 2H), 6.85 (m, 3H), 6.65 (s, 2H), 6.0 (s, 2H), 3.47 (s, 2H), 2.99 (d, J=12.0 Hz, 2H), 2.85 (m, 4H), 2.24 (t, J=11.2 Hz, 2H).
ESIMS+379.7 m/z

Example 183

5-[4-(2-Fluoro-3-methyl-benzyl)-piperazin-1-yl]-quinazoline-2,4-diamine

In an 8 mL vial with stir bar, triethylamine (40 mg; 0.4 mmol) was added to a mixture of 5-piperazin-1-yl-quinazoline-2,4-diamine (50 mg; 0.2 mmol) and 2-fluoro-3-methyl-benzyl bromide (54 mg; 0.27 mmol) in dimethylformamide and heated to 60° C. for 16 hours. Mixture was quenched with 1 mL of 1N NaOH and after 1.5 hours solids were collected by filtration and triturated with ethanol to obtain 37 mg of title compound. (51% yield). $^1$H NMR (400 MHz, DMSO-$d_6$) δ 8.86 (s, 1H), 7.2 (m, 3H), 7.07 (t, J=7.6 Hz, 1H), 6.95 (dd, J=8.4, 0.8 Hz, 1H), 6.84 (dd, J=7.6, 0.8 Hz, 1H), 5.90 (br s, 2H), 3.59 (s, 2H), 2.98 (d, J=11.2 Hz, 2H), 2.89 (d, J=12.0 Hz, 2H), 2.81 (t, J=9.6 Hz, 2H), 2.313 (t, J=9.2 Hz, 2H), 2.24 (s, 3H). ESIMS+367.6 m/z

Example 184

[4-(2,4-Diamino-quinazolin-5-yl)-piperazin-1-yl]-phenyl-methanone

Title compound was prepared via Resin Method using 5-piperazin-1-yl-quinazoline-2,4-diamine (50 mg; 0.2 mmol) and benzoyl chloride (57.6 mg; 0.41 mmol) to obtain 21.3 mg. (31% yield). $^1$H NMR (400 MHz, DMSO-$d_6$) δ 8.78 (s, 1H), 7.46 (m, 5H), 7.39 (t, J=6.0 Hz, 1H), 7.14 (br s, 1H), 6.98 (d, J=6.4 Hz, 1H), 6.86 (d, J=5.6 Hz, 1H), 5.92 (br s, 2H), 4.59 (br s, 1H), 3.66 (br s, 1H), 3.44 (m, 1H), 3.13 (m, 3H), 2.77 (m, 2H).
ESIMS+349.7 m/z

Example 185

[4-(2,4-Diamino-quinazolin-5-yl)-piperazin-1-yl]-p-tolyl-methanone

Title compound was prepared via Resin Method using 5-piperazin-1-yl-quinazoline-2,4-diamine (50 mg; 0.2 mmol) and p-toluoyl chloride (63.4 mg; 0.41 mmol) to obtain 29.5 mg. (41% yield). $^1$H NMR (400 MHz, DMSO-$d_6$) δ 8.78 (s, 1H), 7.37 (m, 2H), 7.26 (m, 3H), 7.14 (br s, 1H), 6.98 (d, J=6.4 Hz, 1H), 6.86 (d, J=5.6 Hz, 1H), 5.92 (br s, 2H), 4.58 (br s, 1H), 4.35 (br s, 1H), 3.66 (br s, 1H), 3.44 (m, 1H), 3.11 (m, 3H), 2.77 (m, 2H), 2.35 (s, 3H). ESIMS+363.8 m/z

Example 186

[4-(2,4-Diamino-quinazolin-5-yl)-piperazin-1-yl]-m-tolyl-methanone

Title compound was prepared via Resin Method using 5-piperazin-1-yl-quinazoline-2,4-diamine (50 mg; 0.2 mmol) and p-toluoyl chloride (63.4 mg; 0.41 mmol) to obtain 24.6 mg. (34% yield). $^1$H NMR (500 MHz, DMSO-$d_6$) δ 8.79 (br s, 1H), 7.38 (m, 3H), 7.26 (d, J=8.0 Hz, 2H), 7.13 (br s, 1H), 6.98 (d, J=8.0 Hz, 1H), 6.86 (d, J=7.5 Hz, 1H), 5.92 (br s, 2H), 4.5 (br s, 1H), 3.7 (br s, 1H), 3.08 (br s, 4H), 2.76 (m, 2H), 2.35 (s, 3H).
ESIMS+363.8 m/z

Example 187

(2-Chloro-phenyl)-[4-(2,4-diamino-quinazolin-5-yl)-piperazin-1-yl]-methanone

Title compound was prepared via Resin Method using 5-piperazin-1-yl-quinazoline-2,4-diamine (50 mg; 0.2 mmol) and 2-chlorobenzoyl chloride (71.8 mg; 0.41 mmol) to obtain 34.1 mg. (45% yield). $^1$H NMR (500 MHz, DMSO-$d_6$) δ 8.78 (s, 1H), 7.50 (m, 3H), 7.41 (m, 2H), 7.15 (br s, 1H), 6.98 (d, J=8.5 Hz, 1H), 6.86 (d, J=8.0 Hz, 1H), 5.92 (br s, 2H), 4.57 (br s, 1H), 3.45 (m, 2H), 3.02 (m, 3H), 2.78 (m, 2H). ESIMS+384.3 m/z Example 188

(4-Chloro-phenyl)-[4-(2,4-diamino-quinazolin-5-yl)-piperazin-1-yl]-methanone

Title compound was prepared via Resin Method using 5-piperazin-1-yl-quinazoline-2,4-diamine (50 mg; 0.2 mmol) and 4-chlorobenzoyl chloride (71.8 mg; 0.41 mmol) to obtain 40.4 mg. (53% yield). $^1$H NMR (400 MHz, DMSO-$d_6$) δ 8.77 (s, 1H), 7.53 (m, 4H), 7.39 (t, J=8.0 Hz, 1H), 7.15 (br s, 1H), 6.98 (d, J=8.5 Hz, 1H), 6.85 (d, J=8.0 Hz, 1H), 5.92 (br s, 2H), 4.56 (br s, 1H), 3.64 (m, 1H), 3.09 (m, 4H), 2.77 (m, 2H) ESIMS+384.1 m/z Example 189

[4-(2,4-Diamino-quinazolin-5-yl)-piperazin-1-yl]-(2,4-dichloro-phenyl)-methanone Title compound was prepared via Resin Method using 5-piperazin-1-yl-quinazoline-2,4-diamine (50 mg; 0.2 mmol) and 2,4-Dichlorobenzoyl chloride (85.9 mg; 0.41 mmol) to obtain 48.1 mg. (58% yield). $^1$H NMR (400 MHz, DMSO-$d_6$) δ 8.67 (br d, 1H), 7.76 (s, 1H), 7.54 (s, 2H), 7.41 (m, 2H), 7.07 (br d, 1H), 6.98 (br d, 1H), 6.83 (t, J=7.6 Hz, 1H), 4.58 (br d, 1H), 3.42 (m, 2H), 3.16 (m, 2H), 2.99 (m, 1H), 2.74 (m, 2H). ESIMS+419.3 m/z Example 190

[4-(2,4-Diamino-quinazolin-5-yl)-piperazin-1-yl]-(3,4-dichloro-phenyl)-methanone Title compound was prepared via Resin Method using 5-piperazin-1-yl-quinazoline-2,4-diamine (50 mg; 0.2 mmol) and 3,4-Dichlorobenzoyl chloride (85.9 mg; 0.41 mmol) to obtain 52.5 mg. (63% yield). $^1$H NMR (400 MHz, DMSO-$d_6$) δ 8.77 (br s, 1H), 7.75 (m, 2H), 7.47 (m, 1H), 7.4 (t, J=8.0 Hz, 1H), 7.18 (br s, 1H), 6.98 (dd, J=8.4, 0.8 Hz, 1H), 6.85 (dd, J=7.6, 0.8 Hz, 1H), 5.93 (s, 2H), 4.55 (br s, 1H), 3.61 (br s, 1H), 3.45 (br s, 1H), 3.14 (m, 3H), 2.79 (m, 2H). ESIMS+419.3 m/z Example 191

[4-(2,4-Diamino-quinazolin-5-yl)-piperazin-1-yl]-(2-fluoro-phenyl)-methanone

Title compound was prepared via Resin Method using 5-piperazin-1-yl-quinazoline-2,4-diamine (50 mg; 0.2 mmol) and 2-fluorobenzoyl chloride (65 mg; 0.41 mmol) to obtain 40.2 mg. (55% yield). $^1$H NMR (500 MHz, DMSO-$d_6$) δ 8.72 (s, 1H), 7.50 (m, 2H), 7.34 (m, 3H), 7.09 (br s, 1H), 6.98 (d, J=8.0 Hz, 1H), 6.83 (d, J=8.0 Hz, 1H), 5.93 (br s, 2H), 4.60 (br d, J=13.5 Hz, 1H), 3.46 (br s, 2H), 3.17 (m, 2H), 3.02 (m, 1H), 2.72 (m, 2H). ESIMS+368.0 m/z Example 192

[4-(2,4-Diamino-quinazolin-5-yl)-piperazin-1-yl]-(4-fluoro-phenyl)-methanone

Title compound was prepared via Resin Method using 5-piperazin-1-yl-quinazoline-2,4-diamine (50 mg; 0.2 mmol) and 4-fluorobenzoyl chloride (65 mg; 0.41 mmol) to obtain 26 mg. (36% yield). $^1$H NMR (400 MHz, DMSO-$d_6$) δ 8.78 (s, 1H), 7.54 (m, 2H), 7.39 (t, J=8.0 Hz, 1H), 7.30 (m, 2H), 7.16 (br s, 1H), 6.98 (d, J=8.0 Hz, 1H), 6.85 (d, J=8.0 Hz, 1H), 5.93 (br s, 2H), 4.55 (br s, 1H), 3.67 (br s, 1H), 3.37 (m, 2H), 3.08 (m, 2H), 2.77 (m, 2H). ESIMS+367.5 m/z Example 193

[4-(2,4-Diamino-quinazolin-5-yl)-piperazin-1-yl]-(2,3-difluoro-phenyl)-methanone Title compound was prepared via Resin Method using 5-piperazin-1-yl-quinazoline-2,4-diamine (50 mg; 0.2 mmol) and 2,3-difluorobenzoyl chloride (72.4 mg; 0.41 mmol) to obtain 27.6 mg. (36% yield). $^1$H NMR (400 MHz, DMSO-$d_6$) δ 8.71 (s, 1H), 7.54 (m, 1H), 7.34 (m, 3H), 7.11 (br s, 1H), 6.98 (d, J=8.0 Hz, 1H), 6.84 (d, J=8.0 Hz, 1H), 5.93 (br s, 2H), 4.60 (br d, 1H), 3.50 (br s, 2H), 3.18 (m, 2H), 3.02 (m, 1H), 2.73 (m, 2H).
ESIMS+385.9 m/z Example 194

4-(2,4-Diamino-quinazolin-5-yl)-piperazin-1-yl]-(2,4-difluoro-phenyl)-methanone

Title compound was prepared via Resin Method using 5-piperazin-1-yl-quinazoline-2,4-diamine (50 mg; 0.2 mmol) and 2,4-difluorobenzoyl chloride (72.4 mg; 0.41 mmol) to obtain 33.5 mg. (44% yield). $^1$H NMR (400 MHz, DMSO-$d_6$) δ 8.72 (s, 1H), 7.55 (m, 1H), 7.41 (m, 2H), 7.21 (m, 1H), 7.11 (br s, 1H), 6.98 (d, J=8.0 Hz, 1H), 6.83 (d, J=8.0 Hz, 1H), 5.93 (br s, 2H), 4.58 (br d, 1H), 3.49 (m, 2H), 3.17 (m, 2H), 3.02 (m, 1H), 2.71 (m, 2H). ESIMS+385.6 m/z Example 195

[4-(2,4-Diamino-quinazolin-5-yl)-piperazin-1-yl]-naphthalen-1-yl-methanone

Title compound was prepared via Resin Method using 5-piperazin-1-yl-quinazoline-2,4-diamine (50 mg; 0.2 mmol) and 1-Naphthoyl chloride (78.2 mg; 0.41 mmol) to obtain 22.1 mg. (28% yield). $^1$H NMR (400 MHz, DMSO-$d_6$) δ 8.86 (s, 1H), 8.0 (d, J=7.6 Hz, 2H), 7.75 (br d, 1H), 7.59 (m, 3H), 7.45 (m, 2H), 7.30 (br s, 1H), 6.98 (d, J=8.0 Hz, 1H), 6.89 (dd, J=17.6, 7.6 Hz, 1H), 6.11 (br s, 2H), 4.78 (br t, 1H), 3.42 (m, 2H), 3.24 (m, 3H), 2.89 (m, 2H). ESIMS+400.0 m/z Example 196

[4-(2,4-Diamino-quinazolin-5-yl)-piperazin-1-yl]-naphthalen-2-yl-methanone

Title compound was prepared via Resin Method using 5-piperazin-1-yl-quinazoline-2,4-diamine (50 mg; 0.2 mmol) and 2-Naphthoyl chloride (78.2 mg; 0.41 mmol) to obtain 61.6 mg. (77% yield). $^1$H NMR (500 MHz, DMSO-$d_6$) δ 9.06 (s, 1H), 8.59 (s, 1H), 8.02 (m, 8H), 7.6 (m, 5H), 7.5 (t, J=8.0 Hz, 1H), 7.09 (d, J=8.5 Hz, 1H), 6.99 (d, J=7.5 Hz, 1H), 6.67 (br s, 2H), 4.64 (br s, 1H), 3.76 (br s, 1H), 3.42 (m, 4H), 2.85 (m, 2H).
ESIMS+399.6 m/z

Example 197

Benzo[1,3]dioxol-5-yl-[4-(2,4-diamino-quinazolin-5-yl)-piperazin-1-yl]-methanone Title compound was prepared via Resin Method using 5-piperazin-1-yl-quinazoline-2,4-diamine (50 mg; 0.2 mmol) and piperonyloyl chloride (75.7 mg; 0.41 mmol) to obtain 42.5 mg. (54% yield). $^1$H NMR (400 MHz, DMSO-$d_6$) δ 8.79 (s, 1H), 7.39 (t, J=8.0 Hz, 1H), 7.15 (br s, 1H), 7.03 (s, 1H), 6.99 (m, 3H), 6.89 (dd, J=7.6, 0.8 Hz, 1H), 6.08 (s, 2H), 5.93 (br s, 2H), 3.27 (m, 4H), 3.06 (m, 2H), 2.76 (m, 2H). ESIMS+394.2 m/z

Example 198

5-[4-(Toluene-3-sulfonyl)-piperazin-1-yl]-quinazoline-2,4-diamine

Title compound was prepared via Resin Method using 5-piperazin-1-yl-quinazoline-2,4-diamine (50 mg; 0.2 mmol) and m-toluenesulfonyl chloride (78.2 mg; 0.41 mmol) to obtain 32.3 mg. (41% yield). $^1$H NMR (400 MHz, DMSO-$d_6$) δ 8.37 (s, 1H), 7.58 (m, 4H), 7.38 (t, J=8.0 Hz, 1H), 6.96 (d, J=8.0 Hz, 1H), 6.84 (d, J=7.6 Hz, 1H), 5.92 (br s, 2H), 3.74 (br d, J=11.6 Hz, 2H), 3.44 (m, 1H), 3.1 (br d, J=12 Hz, 2H), 2.85 (m, 2H), 2.53 (m, 4H). ESIMS+399.6 m/z

Example 199

5-[4-(Naphthalene-2-sulfonyl)-piperazin-1-yl]-quinazoline-2,4-diamine

Title compound was prepared via Resin Method using 5-piperazin-1-yl-quinazoline-2,4-diamine (50 mg; 0.2 mmol) and 2-naphthalene-sulfonyl chloride (79.8 mg; 0.41 mmol) to obtain 50.0 mg. (58% yield). $^1$H NMR (400 MHz, DMSO-$d_6$) δ 8.52 (s, 1H), 8.31 (br s, 1H), 8.23 (m, 2H), 8.13 (m, 1H), 7.84 (m, 1H), 7.77 (m, 2H), 7.37 (m, 1H), 6.96 (d, J=8.0 Hz, 1H), 6.83 (m, 2H), 5.90 (br s, 2H), 3.82 (br d, J=11.2 Hz, 2H), 3.11 (br d, J=12.0 Hz, 2H), 2.87 (m, 2H), 2.64 (m, 2H). ESIMS+436.0 m/z

Example 200

5-[4-(4-Chloro-benzenesulfonyl)-piperazin-1-yl]-quinazoline-2,4-diamine

Title compound was prepared via Resin Method using 5-piperazin-1-yl-quinazoline-2,4-diamine (50 mg; 0.2 mmol) and 4-chlorobenzene-sulfonyl chloride (86.5 mg; 0.41 mmol) to obtain 25.5 mg. (30% yield). $^1$H NMR (400 MHz, DMSO-$d_6$) δ 8.34 (s, 1H), 7.78 (m, 4H), 7.38 (t, J=8.0 Hz, 1H), 6.96 (d, J=8.0 Hz, 1H), 6.92 (br s, 1H), 6.83 (d, J=7.6 Hz, 1H), 5.92 (br s, 2H), 3.73 (br d, J=11.6 Hz, 2H), 3.11 (br d, J=12.0 Hz, 2H), 2.84 (m, 2H), 2.62 (m, 2H). ESIMS+420.5 m/z

Example 201

5-[4-(4-Fluoro-benzenesulfonyl)-piperazin-1-yl]-quinazoline-2,4-diamine

Title compound was prepared via Resin Method using 5-piperazin-1-yl-quinazoline-2,4-diamine (50 mg; 0.2 mmol) and 4-fluorobenzene-sulfonyl chloride (79.8 mg; 0.41 mmol) to obtain 33.2 mg. (41% yield). $^1$H NMR (500 MHz, DMSO-$d_6$) δ 8.35 (s, 1H), 7.89 (m, 2H), 7.54 (t, J=8.5 Hz, 2H), 7.38 (t, J=7.5 Hz, 1H), 6.97 (d, J=8.5 Hz, 1H), 6.93 (s, 1H), 6.83 (d, J=8.0 Hz, 1H), 5.92 (br s, 2H), 3.73 (d, J=11.5 Hz, 2H), 3.11 (d, J=12.0 Hz, 2H), 2.85 (t, J=11.5 Hz, 1H), 2.59 (t, J=11.5 Hz, 2H). ESIMS+404.4.5 m/z

Example 202

5-[4-(Naphthalene-1-sulfonyl)-piperazin-1-yl]-quinazoline-2,4-diamine

Title compound was prepared via Resin Method using 5-piperazin-1-yl-quinazoline-2,4-diamine (50 mg; 0.2 mmol) and 1-Naphthalene-sulfonyl chloride (92.9 mg; 0.41 mmol) to obtain 33.7 mg. (39% yield). $^1$H NMR (400 MHz, DMSO-$d_6$) δ 8.69 (d, J=8.4 Hz, 1H), 8.38 (br s, 1H), 8.32 (d, J=8.4 Hz, 1H), 8.21 (d, J=7.2 Hz, 1H), 8.14 (d, J=7.6 Hz, 1H), 7.73 (m, 3H), 7.36 (t, J=7.6 Hz, 1H), 6.95 (d, J=8.0 Hz, 1H), 6.91 (br s, 1H), 6.77 (d, J=7.2 Hz, 1H), 5.91 (br s, 2H), 3.83 (d, J=12 Hz, 2H), 3.10 (d, J=12.0 Hz, 2H), 2.90 (t, J=11.5 Hz, 1H), 2.75 (t, J=11.5 Hz, 2H). ESIMS+436.0 m/z

Example 203

5-[4-(Toluene-2-sulfonyl)-piperazin-1-yl]-quinazoline-2,4-diamine

Title compound was prepared via Resin Method using 5-piperazin-1-yl-quinazoline-2,4-diamine (50 mg; 0.2 mmol) and o-toluenesulfonyl chloride (78.2 mg; 0.41 mmol) to obtain 29.3 mg. (37% yield). $^1$H NMR (400 MHz, DMSO-$d_6$) δ 8.49 (br s, 1H), 7.86 (d, J=8.0 Hz, 1H), 7.61 (m, 1H), 7.73 (m, 3H), 7.47 (m, 2H), 7.38 (t, J=8.0 Hz, 1H), 6.99 (m, 2H), 6.82 (d, J=7.2 Hz, 1H), 5.93 (br s, 2H), 3.67 (d, J=12 Hz, 2H), 3.12 (d, J=12.0 Hz, 2H), 2.94 (t, J=11.5 Hz, 1H), 2.78 (t, J=11.5 Hz, 2H), 2.62 (s, 3H). ESIMS+400.2 m/z

Example 204

5-(4-Naphthalen-2-ylmethyl-piperazin-1-yl)-quinazoline-2,4-diamine hydrochloride In a 20 mL vial with stir bar, triethylamine (40 mg; 0.4 mmol) was added to a mixture of 5-piperazin-1-yl-quinazoline-2,4-diamine (50 mg; 0.2 mmol) and 2-(bromomethyl)naphthalene (59 mg; 0.26 mmol) in N,N-dimethylformamide and heated to 60° C. for 72 hours. Mixture was quenched with 1 mL of 1N NaOH and after 1.5 hours solids were collected by filtration and triturated with ethanol. Solids were stirred at room temperature with 4M HCl in Dioxane (2 eq). Solids were collected and dried to 60 mg of title compound. (71% yield). $^1$H NMR (500 MHz, DMSO-$d_6$) δ 12.8 (s, 1H), 11.7 (s, 1H), 9.38 (s, 1H), 9.07 (s, 1H), 8.16 (s, 1H), 8.00 (m, 3H), 7.85 (dd, J=8.5, 1.0 Hz, 1H), 7.75 (t, J=8.0 Hz, 1H), 7.61 (m, 2H), 7.27 (d, J=8.5 Hz, 1H), 7.18 (d, J=8.5 Hz, 1H), 4.54 (s, 2H), 3.58 (m, 2H), 3.43 (d, J=11.5 Hz, 2H), 3.32 (t, J=12.0 Hz, 2H), 3.25 (d, J=12.0 Hz, 2H). ESIMS+385.8 m/z

Example 205

4-[2-(2,4-Diamino-quinazolin-5-yloxy)-ethyl]-piperazine-1-carboxylic Acid tert-butyl Ester 4-[2-(2-Cyano-3-fluoro-phenoxy)-ethyl]-piperazine-1-carboxylic Acid tert-butyl Ester t-butyl 4-(2-hydroxyethyl)piperazine-1-carboxylate (0.6 g; 2.6 mmol) was added to a suspension of sodium hydride (125 mg; 3.1 mmol) in 5 mL of anhydrous dimethylformamide at 0° C. Mixture was then heated to 40° C. for 2 hours. Anion was cooled to room temperature and added to a 0° C. mixture of 2,6-difluorobenzonitrile in 5 mL of dimethylformamide. After 16 hours at room temperature, reaction was quenched over 20 g of ice, mixture was extracted 4×50 mL with ethyl acetate. Combined organics was washed with 6×40 mLs water, brine and dried over MgSO$_4$. Crude oil was obtained after filtration and concentration. Material was purified by flash chromatography using 2-3.5% methanol/dichloromethane gradient to obtain 660 mg of title compound. (73% yield).

4-[2-(2,4-Diamino-quinazolin-5-yloxy)-ethyl]-piperazine-1-carboxylic Acid tert-butyl Ester Reaction was carried out using (Method A) 4-[2-(2-Cyano-3-fluoro-phenoxy)-ethyl]-piperazine-1-carboxylic acid tert-butyl ester (0.65 g; 1.9 mmol) to obtain 136 mg of title compound after purification via flash chromatography 5-10% methanol/dichloromethane gradient. (18% yield). $^1$H NMR (400 MHz, DMSO-d$_6$) δ 7.99 (br s, 1H), 11.7 (s, 1H), 7.31 (m, 2H), 6.76 (dd, J=8.4, 1.2 Hz, 1H), 6.55 (d, J=7.6 Hz, 1H), 5.94 (br s, 2H), 4.20 (t, J=5.2 Hz, 2H), 3.35 (m, 2H), 2.76 (t, J=5.2 Hz, 2H), 2.54 (d, J=1.6 Hz, 2H), 2.41 (t, J=4.8 Hz, 4H), 1.40 (s, 9H). ESIMS+389.1 m/z Example 206

5-{2-[4-(2-Fluoro-benzenesulfonyl)-piperazin-1-yl]-ethoxy}-quinazoline-2,4-diamine 5-(2-piperazin-1-yl-ethoxy)-quinazoline-2,4-diamine trifluoroacetate In a 100 mL round bottom flask 4-[2-(2,4-Diamino-quinazolin-5-yloxy)-ethyl]-piperazine-1-carboxylic acid tert-butyl ester (2.3 g; 5.9 mmol) was magnetically stirred in 20 mL of dichloromethane and trifluoroacetic acid (3 mL) was added dropwise at room temperature. After 16 hours, solids were filtered and rinsed with 10 mls of dichloromethane. Title compound was obtained 2.1 g (88% yield).

5-{2-[4-(2-Fluoro-benzenesulfonyl)-piperazin-1-yl]-ethoxy}-quinazoline-2,4-diamine (Method B)

In an 8 mL vial triethylamine (40 mg; 0.4 mmol) was added to a mixture of 5-(2-piperazin-1-yl-ethoxy)-quinazoline-2,4-diamine trifluoroacetate (50 mg; 0.1 mmol) in 1.5 mL of tetrahydrofuran. 2-Fluorobenzene-sulfonyl chloride was added and reaction stirred at room temperature for 16 hours. Reaction was purified by reprecipitation with ethanol and (0.5:1) 1N NaOH. Solids were filtered to obtain 14 mg of title compound. (310% yield). $^1$H NMR (400 MHz, DMSO-d$_6$) δ 7.77 (m, 3H), 7.48 (m, 2H), 7.32 (t, J=8.4 Hz, 1H), 7.18 (br s, 1H), 6.74 (d, J=8.4 Hz, 1H), 6.50 (d, J=7.6 Hz, 1H), 5.87 (br s, 2H), 4.16 (t, J=5.2 Hz, 2H), 3.17 (br s, 4H), 2.77 (t, J=5.2 Hz, 2H), 2.52 (m, 4H).
ESIMS+448.4 m/z Example 207

{4-[2-(2,4-Diamino-quinazolin-5-yloxy)-ethyl]-piperazin-1-yl}-(2,4-difluoro-phenyl)-methanone Title compound was carried out via (Method B) with 2,4-difluorobenzoyl chloride (24 mg; 0.14 mmol). Reaction was purified via flash chromatography followed by reprecipitation using ethanol and 1N NaOH (0.5:1). (9.1 mg; 21% yield). $^1$H NMR (400 MHz, DMSO-d$_6$) δ 7.97 (br s, 1H), 7.46 (m, 1H), 7.35 (m, 2H), 7.26 (br s, 1H), 7.19 (d, J=8.8 Hz, 1H), 6.75 (d, J=8.4 Hz, 1H), 6.53 (d, J=7.6 Hz, 1H), 5.88 (br s, 2H), 4.20 (t, J=5.2 Hz, 2H), 3.69 (br s, 2H), 3.27 (br s, 2H), 2.79 (t, J=5.2 Hz, 2H), 2.43 (br s, 2H).
ESIMS+430.2 m/z Example 208

Benzo[1,3]dioxol-5-yl-{4-[2-(2,4-diamino-quinazolin-5-yloxy)-ethyl]-piperazin-1-yl}-methanone Title compound was carried out via Resin Method with 5-(2-piperazin-1-yl-ethoxy)-quinazoline-2,4-diamine trifluoroacetate (50 mg; 0.1 mmol) and piperonyloyl chloride (46.1 mg; 0.25 mmol) in 3 mL of tetrahydrofuran to obtain 21.8 mg. (50% yield). $^1$H NMR (400 MHz, DMSO-d$_6$) δ 8.0 (br s, 1H), 7.34 (t, J=8.0 Hz, 1H), 7.24 (br s, 1H), 6.94 (m, 2H), 6.88 (m, 1H), 6.75 (dd, J=8.4, 0.8 Hz, 1H), 6.54 (d, J=8.0 Hz, 1H), 6.07 (s, 2H), 5.88 (br s, 2H), 4.20 (t, J=5.2 Hz, 2H), 3.52 (m, 4H), 2.79 (t, J=5.2 Hz, 2H), 2.49 (m, 4H). ESIMS+ 438.2 m/z Example 209

5-[2-(4-Benzenesulfonyl-piperazin-1-yl)-ethoxy]-quinazoline-2,4-diamine

Title compound was carried out via Resin Method with 5-(2-piperazin-1-yl-ethoxy)-quinazoline-2,4-diamine trifluoroacetate (50 mg; 0.1 mmol) and benzenesulfonyl chloride (44.2 mg; 0.25 mmol) in 3 mL of tetrahydrofuran to obtain 21.0 mg. (43% yield). $^1$H NMR (400 MHz, DMSO-d$_6$) δ 7.77 (m, 3H), 7.65 (m, 2H), 7.57 (br s, 1H), 7.31 (t, J=8.0 Hz, 1H), 7.04 (br s, 1H), 6.73 (d, J=8.4 Hz, 1H), 6.47 (d, J=8.0 Hz, 1H), 5.87 (br s, 2H), 4.13 (t, J=5.2 Hz, 2H), 2.99 (br s, 4H), 2.74 (m, 2H), 2.52 (m, 4H).
ESIMS+430.4 m/z Example 210

5-{2-[4-(2,4-Difluoro-benzenesulfonyl)-piperazin-1-yl]-ethoxy}-quinazoline-2,4-diamine Title compound was carried out via Resin Method with 5-(2-piperazin-1-yl-ethoxy)-quinazoline-2,4-diamine trifluoroacetate (50 mg; 0.1 mmol) and 2,4-difluorobenzenesulfonyl chloride (53.2 mg; 0.25 mmol) in 3 mL of tetrahydrofuran to obtain 30.1 mg. (65% yield). $^1$H NMR (400 MHz, DMSO-d$_6$) δ 7.85 (m, 1H), 7.75 (br s, 1H), 7.61 (m, 1H), 7.32 (m, 2H), 7.22 (br s, 1H), 6.74 (dd, J=8.4, 0.4 Hz, 1H), 6.5 (d, J=8.0 Hz, 1H), 5.86 (br s, 2H), 4.16 (t, J=5.2 Hz, 2H), 3.15 (br s, 4H), 2.77 (t, J=5.2 Hz, 2H), 2.53 (m, 4H). ESIMS+466.3 m/z Example 211

5-{2-[4-(3,4-Dichloro-benzenesulfonyl)-piperazin-1-yl]-ethoxy}-quinazoline-2,4-diamine Title compound was carried out via Resin Method with 5-(2-piperazin-1-yl-ethoxy)-quinazoline-2,4-diamine trifluoroacetate (50 mg; 0.1 mmol) and 3,4-dichlorobenzenesulfonyl chloride (61.4 mg; 0.25 mmol) in 3 mL of tetrahydrofuran to obtain 24.1 mg. (50% yield). $^1$H NMR (400 MHz, DMSO-d$_6$) δ 7.95 (m, 2H), 7.71 (m, 2H), 7.32 (m, 1H), 7.18 (br s, 1H), 6.73 (m, 1H), 6.49 (d, J=8.0 Hz, 1H), 5.86 (br s, 2H), 4.15 (t, J=5.2 Hz, 2H), 3.07 (br s, 4H), 2.77 (t, J=5.2 Hz, 2H), 2.52 (m, 4H). ESIMS+498.4 m/z Example 212

{4-[2-(2,4-Diamino-quinazolin-5-yloxy)-ethyl]-piperazin-1-yl}-(3,4-dichloro-phenyl)-methanone Title compound was carried out via Resin Method with 5-(2-piperazin-1-yl-ethoxy)-quinazoline-2,4-diamine trifluoroacetate (50 mg; 0.1 mmol) and 3,4-dichlorobenzoyl chloride (52.4 mg; 0.25 mmol) in 3 mL of tetrahydrofuran to obtain 19 mg. (41% yield).
$^1$H NMR (400 MHz, DMSO-d$_6$) δ 8.00 (br s, 1H), 7.72 (m, 1H), 7.66 (m, 1H), 7.38 (m, 2H), 7.23 (br s, 1H), 6.76 (d, J=8.0 Hz, 1H), 6.54 (d, J=8.0 Hz, 1H), 5.90 (br s, 2H), 4.21 (t, J=5.2 Hz, 2H), 3.66 (br s, 2H), 3.36 (br s, 2H), 2.79 (t, J=5.2 Hz, 2H), 2.54 (m, 2H). ESIMS+462.2 m/z

Example 213

{4-[2-(2,4-Diamino-quinazolin-5-yloxy)-ethyl]-piperazin-1-yl}-phenyl-methanone

Title compound was carried out via Resin Method with 5-(2-piperazin-1-yl-ethoxy)-quinazoline-2,4-diamine trifluoroacetate (50 mg; 0.1 mmol) and benzoyl chloride (35.1 mg; 0.25 mmol) in 3 mL of tetrahydrofuran to obtain 23.9 mg. (61% yield). $^1$H NMR (400 MHz, DMSO-$d_6$) δ 7.99 (br s, 1H), 7.45 (m, 3H), 7.37 (m, 3H), 7.24 (br s, 1H), 6.75 (d, J=8.4 Hz, 1H), 6.53 (d, J=8.0 Hz, 1H), 5.88 (br s, 2H), 4.20 (t, J=5.2 Hz, 2H), 3.67 (br s, 2H), 3.37 (br s, 2H), 2.79 (t, J=5.2 Hz, 2H), 2.54 (m, 4H). ESIMS+393.6 m/z

Example 214

(4-Chloro-phenyl)-{4-[2-(2,4-diamino-quinazolin-5-yloxy)-ethyl]-piperazin-1-yl}-methanone Title compound was carried out via Resin Method with 5-(2-piperazin-1-yl-ethoxy)-quinazoline-2,4-diamine trifluoroacetate (50 mg; 0.1 mmol) and 3-chlorobenzoyl chloride (46 uL; 0.35 mmol) in 3 mL of tetrahydrofuran to obtain 24.2 mg. (57% yield). $^1$H NMR (400 MHz, DMSO-$d_6$) δ 8.0 (br s, 1H), 7.53 (m, 3H), 7.35 (m, 2H), 7.23 (br s, 1H), 6.76 (d, J=8.4 Hz, 1H), 6.54 (d, J=8.0 Hz, 1H), 5.88 (br s, 2H), 4.20 (t, J=5.2 Hz, 2H), 3.66 (br s, 2H), 3.35 (br s, 2H), 2.79 (t, J=5.2 Hz, 2H), 2.54 (m, 4H). ESIMS+427.0 m/z

Example 215

{4-[2-(2,4-Diamino-quinazolin-5-yloxy)-ethyl]-piperazin-1-yl}-(2-fluoro-phenyl)-methanone Title compound was carried out via Resin Method with 5-(2-piperazin-1-yl-ethoxy)-quinazoline-2,4-diamine trifluoroacetate (50 mg; 0.1 mmol) and 2-fluorobenzoyl chloride (43 uL; 0.35 mmol) in 3 mL of tetrahydrofuran to obtain 26.2 mg. (64% yield). $^1$H NMR (400 MHz, DMSO-$d_6$) δ 7.98 (br s, 1H), 7.49 (m, 1H), 7.49 (m, 2H), 7.3 (m, 3H), 6.75 (d, J=8.4 Hz, 1H), 6.53 (d, J=8.0 Hz, 1H), 5.88 (br s, 2H), 4.20 (t, J=5.2 Hz, 2H), 3.70 (br s, 2H), 3.35 (t, J=4.4 Hz, 2H), 2.79 (t, J=5.2 Hz, 2H), 2.54 (t, J=4.4 Hz, 2H), 2.43 (br s, 2H). ESIMS+411.8 m/z

Example 216

5-{2-[4-(2-Fluoro-benzyl)-piperazin-1-yl]-ethoxy}-quinazoline-2,4-diamine

Title compound was carried out via Resin Method with 5-(2-piperazin-1-yl-ethoxy)-quinazoline-2,4-diamine trifluoroacetate (50 mg; 0.1 mmol) and 2-fluorobenzyl bromide (43 uL; 0.35 mmol) in 3 mL of tetrahydrofuran to obtain 20 mg. (50% yield). $^1$H NMR (400 MHz, DMSO-$d_6$) δ 7.87 (br s, 1H), 7.40 (m, 1H), 7.30 (m, 2H), 7.15 (m, 3H), 6.75 (d, J=8.4 Hz, 1H), 6.52 (d, J=8.0 Hz, 1H), 5.87 (br s, 2H), 4.17 (t, J=5.2 Hz, 2H), 3.52 (s, 2H), 2.74 (s, 2H), 2.45 (m, 8H). ESIMS+397.6 m/z

Example 217

5-{2-[4-(2,4-Difluoro-benzyl)-piperazin-1-yl]-ethoxy}-quinazoline-2,4-diamine

Title compound was carried out via Resin Method with 5-(2-piperazin-1-yl-ethoxy)-quinazoline-2,4-diamine trifluoroacetate (50 mg; 0.1 mmol) and 2,4-difluorobenzyl bromide (46 uL; 0.35 mmol) in 3 mL of tetrahydrofuran to obtain 17.1 mg. (41% yield). $^1$H NMR (400 MHz, DMSO-$d_6$) δ 7.87 (br s, 1H), 7.42 (m, 1H), 7.33 (m, 1H), 7.18 (m, 2H), 7.06 (m, 1H), 6.75 (d, J=8.4 Hz, 1H), 6.52 (d, J=8.0 Hz, 1H), 5.86 (br s, 2H), 4.17 (t, J=5.2 Hz, 2H), 3.50 (s, 2H), 2.73 (s, 2H), 2.44 (m, 8H). ESIMS+415.8 m/z

Example 218

5-{2-[4-(3-Chloro-benzyl)-piperazin-1-yl]-ethoxy}-quinazoline-2,4-diamine

Title compound was carried out via Resin Method with 5-(2-piperazin-1-yl-ethoxy)-quinazoline-2,4-diamine trifluoroacetate (50 mg; 0.1 mmol) and 3-chlorobenzyl bromide (47 uL; 0.35 mmol) in 3 mL of tetrahydrofuran to obtain 17.3 mg. (42% yield). $^1$H NMR (400 MHz, DMSO-$d_6$) δ 7.87 (br s, 1H), 7.65 (m, 2H), 7.58 (m, 2H), 7.35 (m, 3H), 6.75 (d, J=8.4 Hz, 1H), 6.52 (d, J=8.0 Hz, 1H), 5.86 (br s, 2H), 4.17 (t, J=5.2 Hz, 2H), 3.48 (s, 2H), 2.75 (t, J=5.2 Hz, 2H), 2.43 (m, 8H). ESIMS+413.6 m/z

Example 222

3-[4-(2,4-Diamino-quinazolin-5-yloxymethyl)-piperidin-1-ylmethyl]-benzoic acid $^1$HNMR (400 MHz, DMSO-$d_6$) δ 7.77 (s, 1H), 7.69 (m, 1H), 7.33 (t, J=8.0 Hz, 1H), 7.27 (br s, 1H), 7.20 (br s, 1H), 7.14 (d, J=1.2 Hz, 2H), 6.76 (d, J=7.6 Hz, 1H), 6.52 (d, J=7.6 Hz, 1H), 5.94 (s, 2H), 3.99 (d, J=6.0 Hz, 2H), 3.44 (s, 2H), 2.85 (br d, J=11.2 Hz, 2H), 1.97 (t, J=10.8 Hz, 2H), 1.86 (m, 1H), 1.73 (d, J=12.8 Hz, 2H), 1.39 (q, J=12.0 Hz, 2H).

Example 223

4-[4-(2,4-Diamino-quinazolin-5-yloxymethyl)-piperidin-1-ylmethyl]-benzoic Acid $^1$HNMR (400 MHz, DMSO-$d_6$) δ 13.00 (s, 1H), 8.82 (s, 1H), 8.24 (s, 1H), 8.01 (d, J=8.0 Hz, 2H), 7.82 (d, J=8.0 Hz, 2H), 7.69 (t, J=8.4 Hz, 1H), 7.03 (d, J=8.4 Hz, 1H), 7.00 (d, J=8.0 Hz, 1H), 4.35 (d, J=5.2 Hz, 2H), 4.17 (d, J=6.4 Hz, 2H), 3.88 (s, 2H), 3.64 (br s, 2H), 2.94 (m, 2H), 2.20 (m, 1H), 1.98 (m, 2H), 1.80 (m, 2H).

Example 224

5-{1-[1-(2,6-Dichloro-benzyl)-piperidin-4-yl]-1-methyl-ethoxy}-quinazoline-2,4-diamine $^1$HNMR (400 MHz, DMSO-$d_6$) δ 7.45 (d, J=8.0 Hz, 2H), 7.32 (m, 3H), 7.19 (br s, 1H), 6.82 (d, J=8.4 Hz, 1H), 6.67 (d, J=7.6 Hz, 1H), 5.93 (s, 2H), 3.66 (s, 2H), 2.88 (d, J=11.2 Hz, 2H), 2.14 (t, J=10.8 Hz, 2H), 1.99 (m, 1H), 1.66 (d, J=12.0 Hz, 2H), 1.35 (s, 6H), 1.30 (m, 2H).

Example 225

5-{1-[1-(2-Chloro-6-fluoro-benzyl)-piperidin-4-yl]-1-methyl-ethoxy}-quinazoline-2,4-diamine $^1$HNMR (400 MHz, DMSO-$d_6$) δ 7.33 (m, 4H), 7.21 (m, 2H), 6.81 (d, J=8.4 Hz, 1H), 6.66 (d, J=8.0 Hz, 1H), 5.92 (s, 2H), 3.58 (s, 2H), 2.89 (d, J=10.8 Hz, 2H), 2.05 (t, J=11.2 Hz, 2H), 1.95 (m, 1H), 1.66 (d, J=12.8 Hz, 2H), 1.35 (s, 6H), 1.32 (m, 2H).

Example 226

5-[1-(2-Fluoro-benzyl)-2,6-dimethyl-piperidin-4-ylmethoxy]-quinazoline-2,4-diamine $^1$HNMR (400 MHz, DMSO-$d_6$) δ 7.68 (t, J=7.6 Hz, 1H), 7.34 (t, J=8.0 Hz, 1H), 7.20 (m, 4H), 7.09 (t, J=9.6 Hz, 1H), 6.77 (d, J=8.4 Hz, 1H), 6.53 (d, J=8.0 Hz, 1H), 5.94 (s, 2H), 3.97 (d, J=6.0 Hz, 2H), 3.74 (s, 2H), 2.59 (m, 2H), 2.04 (m, 1H), 1.73 (d, J=13.2 Hz, 2H), 1.13 (q, J=12.0 Hz, 2H), 0.97 (d, J=6.4 Hz, 6H).

Example 227

5-[1-(2-Chloro-6-fluoro-benzyl)-2,6-dimethyl-piperidin-4-ylmethoxy]-quinazoline-2,4-diamine $^1$HNMR (400 MHz, DMSO-d$_6$) δ 7.34 (t, J=8.0 Hz, 1H), 7.26 (m, 2H), 7.20 (br s, 2H), 7.13 (t, J=8.8 Hz, 1H), 6.76 (d, J=8.0 Hz, 1H), 6.53 (d, J=8.0 Hz, 1H), 5.95 (br s, 2H), 3.96 (d, J=6.4 Hz, 2H), 3.86 (s, 2H), 2.60 (m, 2H), 2.06 (m, 1H), 1.62 (d, J=12.4 Hz, 2H), 1.19 (q, J=12.4 Hz, 2H), 1.01 (d, J=6.4 Hz, 6H).

All compounds were screened using an in vitro based SMN2 promoter assay. We used NSC-34 cells, a hybrid cell line between mouse spinal cord cells and mouse neuroblastoma cells. NSC-34 cells harbor an expression plasmid containing a 3.4 kb promoter fragment of the SMN2 gene driving β-lactamase expression.

For biological evaluation the NSC-34 cells are incubated (60,000 cells/well) with 10 and 50 μM of compound for 19 hours. Following the incubation, the cells are further incubated for three hours with the β-lactamase substrate CCF2-AM (Invitrogen) (Zlokarnik et. al., 1998. Science vol. 279, pp. 84). CCF2-AM diffuses across the plasma membrane and is converted into an active β-lactamase substrate by cytoplasmic esterase. Excitation at 409 nM leads to fluorescence resonance energy transfer and reemission of green light at 520 nM. Hydrolysis by the β-lactamase of the active substrate leads to emission at 447 nM following excitation at 409 nM. Fold induction is therefore determined by comparing the 447/520 ratios for a compound versus DMSO control (negative control). The fold induction is proportional to the extent of β-lactamase produced and in turn proportional to SMN2 promoter activation for a given compound relative to vehicle (DMSO) control. Compounds that give 1.2 to 2-fold induction at 10 uM are further tested using 12 point dose curve to obtain a EC$_{50}$ value using the NSC-34 promoter assay as described above—(dose range –30 uM to 0.0002 μM). Average of 3-6 different dose curve experiments are used to obtain an average EC$_{50}$ value and the fold induction at maximum stimulation. These values are used to rank activities of the compounds and derive structure activity relationship. The promoter assay data for various of these examples is shown in Tables 1-6. Compounds with EC$_{50}$<1 uM are designated "1"; compounds with EC$_{50}$ 1-5 uM are designated "2"; compounds with EC$_{50}$ 5-10 μM are designated "3"; compounds with EC$_{50}$ 10-20 μM are designated "4".

Human DHFR assay data is also presented for various compounds in Tables 1-5. The assay is an adaptation for 96-well plate format from Appleman et al. (Appleman, J R; Howell, E E; Kraut, J; Kuhl, M and Blakley, R L (1988) *J. Biol. Chem.* 263, 9187-9198). Human, recombinant dihydrofolate reductase (Sigma, D6566) was incubated along with test compounds (119 μM-125 μM) and NADPH (Sigma, N-7505) in 96-well plates. After a 10 min. pre-incubation at room temperature, dihydrofolic acid (Sigma, D7006) was added and the kinetic traces at 340 nm measured on a Spectra Max 190 plate reader at room temperature. Reaction rates were determined from the slopes of the linear portions of the progress curves. The final assay conditions were 0.014 units DHFR, 300 μM NADPH, 30 μM Dihydrofolic acid, 50 mM TRIS, pH 7.6, 100 mM NaCl and 1.25% DMSO. Each compound was measured in duplicates on every assay plate. Each assay plate contained 12 positive controls (DMSO only) and 12 negative controls (no dihydrofolic acid). All data was percent normalized with respect to controls and presented as percent inhibition. Inhibition data was analyzed using Prism and fit to a standard 4-parameter logistic equation to calculate IC50 values.

In Tables 1-6, "X" or "X1" in the sub-structures under the column heading "Q+R1" is the point of attachment to the respective core structure.

TABLE 1

| Example No. | Q + R1 | Promoter Assay EC$_{50}$<br>1 = <1 μM, 2 = 1-5 μM<br>3 = 5-10 μM, 4 = 10-20 μM | hDHFR IC50<br>A < 20 μM, B = 20-100 μM, C > 100 μM |
|---|---|---|---|
| Example-001 | 2-F-benzyl-X$_1$ | 1 | B |
| Example-002 | 3-Cl-benzyl-X$_1$ | 1 | A |

TABLE 1-continued
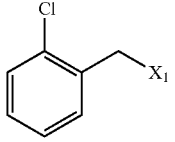
| Example No. | Q + R1 | Promoter Assay EC$_{50}$ 1 = <1 μM, 2 = 1-5 μM 3 = 5-10 μM, 4 = 10-20 μM | hDHFR IC50 A < 20 μM, B = 20-100 μM, C > 100 μM |
|---|---|---|---|
| Example-003 | 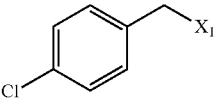 | 1 | B |
| Example-004 | 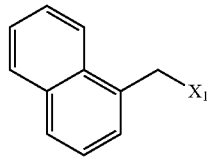 | 1 | |
| Example-005 | 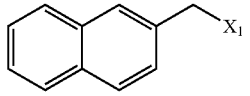 | 1 | |
| Example-006 | 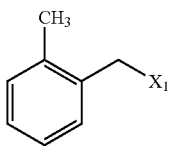 | 1 | |
| Example-007 | 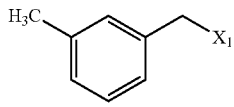 | 1 | B |
| Example-008 | 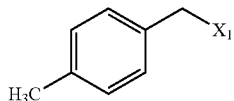 | 1 | C |
| Example-009 | 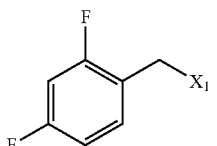 | 1 | C |
| Example-010 | | 1 | B |

TABLE 1-continued

[Structure: 2,4-diaminoquinazoline with 5-O-CH2-(piperidin-4-yl), N-Q-R1]

| Example No. | Q + R1 | Promoter Assay EC$_{50}$ 1 = <1 μM, 2 = 1-5 μM, 3 = 5-10 μM, 4 = 10-20 μM | hDHFR IC50 A < 20 μM, B = 20-100 μM, C > 100 μM |
|---|---|---|---|
| Example-011 | 3,4-difluorobenzyl-X$_1$ | 1 | |
| Example-012 | 2,3-difluorobenzyl-X$_1$ | 1 | B |
| Example-013 | 2-fluorobenzoyl-X$_1$ | 1 | |
| Example-014 | 3-chlorobenzoyl-X$_1$ | 1 | C |
| Example-015 | 2-chlorobenzoyl-X$_1$ | 1 | B |
| Example-016 | 4-chlorobenzoyl-X$_1$ | 1 | C |

TABLE 1-continued
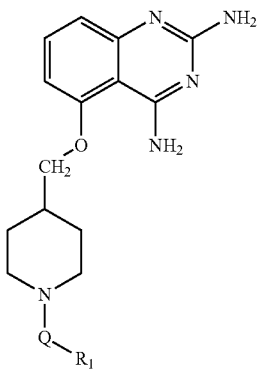
| Example No. | Q + R1 | Promoter Assay EC$_{50}$ 1 = <1 μM, 2 = 1-5 μM 3 = 5-10 μM, 4 = 10-20 μM | hDHFR IC50 A < 20 μM, B = 20-100 μM, C > 100 μM |
|---|---|---|---|
| Example-017 | 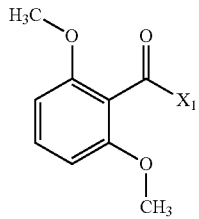 | 1 | |
| Example-018 | 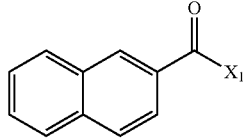 | 1 | |
| Example-019 | 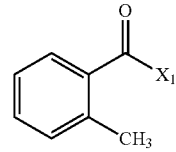 | 1 | |
| Example-020 | 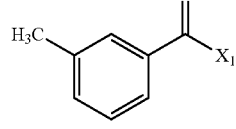 | 1 | |
| Example-021 | 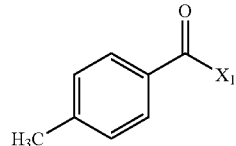 | 1 | |
| Example-022 | 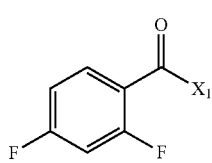 | 1 | |

TABLE 1-continued
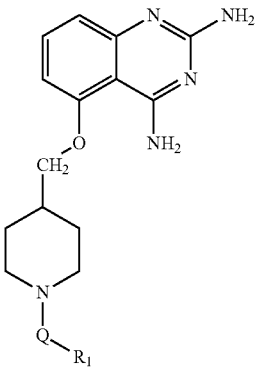
| Example No. | Q + R1 | Promoter Assay EC$_{50}$ 1 = <1 μM, 2 = 1-5 μM 3 = 5-10 μM, 4 = 10-20 μM | hDHFR IC50 A < 20 μM, B = 20-100 μM, C > 100 μM |
|---|---|---|---|
| Example-023 | 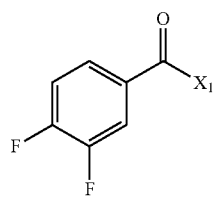 | 1 | |
| Example-024 | 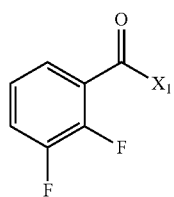 | 1 | B |
| Example-025 | 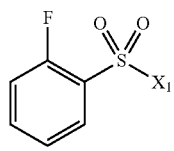 | 1 | B |
| Example-026 | 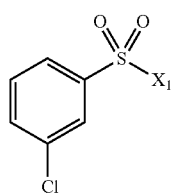 | 1 | |
| Example-027 | 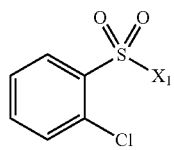 | 1 | |
| Example-028 | 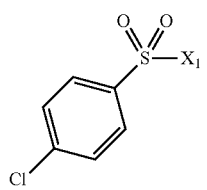 | 1 | |

TABLE 1-continued

| Example No. | Q + R1 | Promoter Assay EC$_{50}$ 1 = <1 µM, 2 = 1-5 µM 3 = 5-10 µM, 4 = 10-20 µM | hDHFR IC50 A < 20 µM, B = 20-100 µM, C > 100 µM |
|---|---|---|---|
| Example-029 | 1-naphthylsulfonyl-X$_1$ | 1 | |
| Example-030 | 2-naphthylsulfonyl-X$_1$ | 1 | |
| Example-031 | 2-methylphenylsulfonyl-X$_1$ | 1 | |
| Example-032 | 3-methylphenylsulfonyl-X$_1$ | 1 | |
| Example-033 | 4-methylphenylsulfonyl-X$_1$ | 1 | |
| Example-034 | 2,4-difluorophenylsulfonyl-X$_1$ | 1 | |

TABLE 1-continued

[Structure: quinazoline-2,4-diamine with 5-O-CH2-piperidine-N-Q-R1]

| Example No. | Q + R1 | Promoter Assay EC$_{50}$ 1 = <1 µM, 2 = 1-5 µM 3 = 5-10 µM, 4 = 10-20 µM | hDHFR IC50 A < 20 µM, B = 20-100 µM, C > 100 µM |
|---|---|---|---|
| Example-035 | 3,4-difluorophenylsulfonyl-X$_1$ | 1 | |
| Example-036 | X$_1$—H | 1 | |
| Example-037 | tert-butoxycarbonyl-X$_1$ | 1 | |
| Example-038 | 3,4-dichlorobenzyl-X$_1$ | 1 | A |
| Example-039 | 3-iodobenzoyl-X$_1$ | 1 | C |
| Example-040 | 4-iodobenzoyl-X$_1$ | 1 | |
| Example-041 | 2-iodobenzoyl-X$_1$ | 1 | |

TABLE 1-continued

[Structure: 2,4-diaminoquinazoline with 5-O-CH2-piperidine-N-Q-R1]

| Example No. | Q + R1 | Promoter Assay EC$_{50}$ 1 = <1 µM, 2 = 1-5 µM 3 = 5-10 µM, 4 = 10-20 µM | hDHFR IC50 A < 20 µM, B = 20-100 µM, C > 100 µM |
|---|---|---|---|
| Example-042 | 2-iodobenzoyl–X$_1$ | 1 | |
| Example-043 | 3-iodobenzyl–X$_1$ | 1 | A |
| Example-044 | 4-iodobenzyl–X$_1$ | 1 | |
| Example-045 | (4-methoxyphenyl)acetyl–X$_1$ | 2 | |
| Example-046 | 3-fluorobenzoyl–X$_1$ | 1 | |
| Example-047 | 4-(methylsulfonyl)benzyl–X$_1$ | 1 | |
| Example-048 | pivaloyl (2,2-dimethylpropanoyl)–X$_1$ | 1 | |

TABLE 1-continued

| Example No. | Q + R1 | Promoter Assay EC$_{50}$ 1 = <1 μM, 2 = 1-5 μM 3 = 5-10 μM, 4 = 10-20 μM | hDHFR IC50 A < 20 μM, B = 20- 100 μM, C > 100 μM |
|---|---|---|---|
| Example-049 | 4-methylcyclohexyl-C(O)-X$_4$ | 1 | |
| Example-050 | cyclopropyl-C(O)-X$_1$ | 1 | C |
| Example-051 | 6-chloropyridin-3-yl-C(O)-X$_1$ | 1 | |
| Example-052 | 2,5-difluorophenyl-C(O)-X$_1$ | 1 | |
| Example-053 | norbornyl-CH$_2$-C(O)-X$_1$ | 1 | C |
| Example-054 | 3,5-dichlorophenyl-C(O)-X$_1$ | 1 | |
| Example-055 | thiophen-2-yl-C(O)-X$_1$ | 1 | |

TABLE 1-continued

[Structure: 2,4-diaminoquinazoline with 5-O-CH2-(piperidin-4-yl), piperidine N substituted with Q-R1]

| Example No. | Q + R1 | Promoter Assay EC$_{50}$ 1 = <1 μM, 2 = 1-5 μM 3 = 5-10 μM, 4 = 10-20 μM | hDHFR IC50 A < 20 μM, B = 20-100 μM, C > 100 μM |
|---|---|---|---|
| Example-056 | 4-methoxybenzoyl (H5C-O-C6H4-C(=O)-X1) | 1 | |
| Example-057 | furan-2-carbonyl | 1 | |
| Example-058 | naphthalene-1-carbonyl | 1 | B |
| Example-059 | 5-methylisoxazole-3-carbonyl | 1 | |
| Example-060 | 2,4-dichlorobenzoyl | 1 | |
| Example-061 | 2-(trifluoromethoxy)benzoyl | 1 | |

TABLE 1-continued

[Structure: quinazoline-2,4-diamine with 5-O-CH2-piperidine-N-Q-R1]

| Example No. | Q + R1 | Promoter Assay EC$_{50}$ 1 = <1 μM, 2 = 1-5 μM 3 = 5-10 μM, 4 = 10-20 μM | hDHFR IC50 A < 20 μM, B = 20-100 μM, C > 100 μM |
|---|---|---|---|
| Example-062 | 4-F-C6H4-C(O)-X1 | 1 | |
| Example-063 | 4-(OCF3)-C6H4-C(O)-X1 | 1 | |
| Example-064 | 4-(CH2CH3)-C6H4-C(O)-X1 | 1 | |
| Example-065 | 3-(OCF3)-C6H4-C(O)-X1 | 1 | B |
| Example-066 | cyclobutyl-C(O)-X1 | 1 | C |
| Example-067 | (CH3CH2)2CH-C(O)-X1 | 1 | C |

TABLE 1-continued
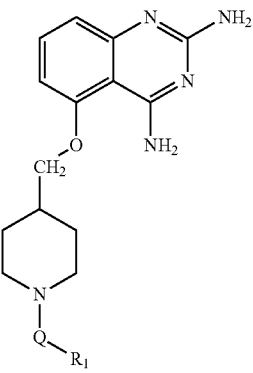
| Example No. | Q + R1 | Promoter Assay EC$_{50}$ 1 = <1 µM, 2 = 1-5 µM 3 = 5-10 µM, 4 = 10-20 µM | hDHFR IC50 A < 20 µM, B = 20- 100 µM, C > 100 µM |
|---|---|---|---|
| Example-068 | 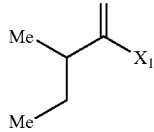 | 1 | C |
| Example-069 | 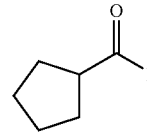 | 1 | C |
| Example-070 | 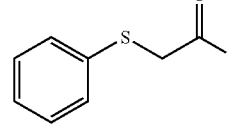 | 1 | |
| Example-071 | 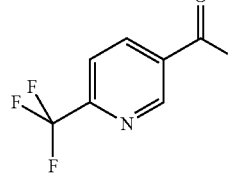 | 1 | |
| Example-072 | 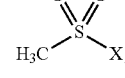 | 1 | |
| Example-073 | 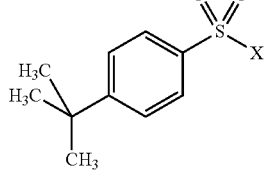 | 1 | |
| Example-074 | 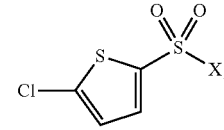 | 1 | |

TABLE 1-continued
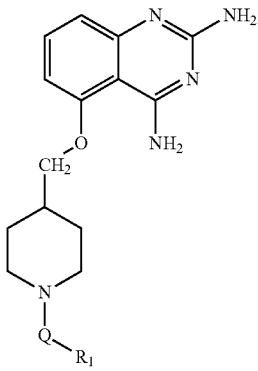
| Example No. | Q + R1 | Promoter Assay EC$_{50}$ 1 = <1 μM, 2 = 1-5 μM 3 = 5-10 μM, 4 = 10-20 μM | hDHFR IC50 A < 20 μM, B = 20- 100 μM, C > 100 μM |
|---|---|---|---|
| Example-075 | thiophene-2-sulfonyl-X$_1$ | 1 | |
| Example-076 | 3,5-dimethylisoxazole-4-sulfonyl-X$_1$ | 1 | |
| Example-077 | 3-fluorobenzenesulfonyl-X$_1$ | 1 | |
| Example-078 | 2,3-dichlorobenzenesulfonyl-X$_1$ | 1 | |
| Example-079 | 5-fluoro-2-methylbenzenesulfonyl-X$_1$ | 1 | |
| Example-080 | 5-chloro-2-methoxybenzenesulfonyl-X$_1$ | 1 | |

TABLE 1-continued
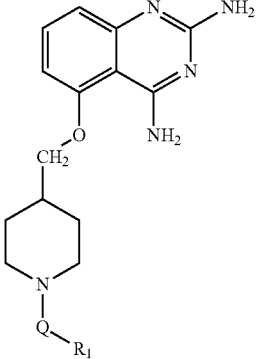
| Example No. | Q + R1 | Promoter Assay EC$_{50}$ 1 = <1 μM, 2 = 1-5 μM 3 = 5-10 μM, 4 = 10-20 μM | hDHFR IC50 A < 20 μM, B = 20-100 μM, C > 100 μM |
|---|---|---|---|
| Example-081 | 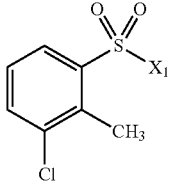 | 1 | |
| Example-082 | 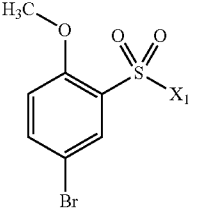 | 1 | |
| Example-083 | 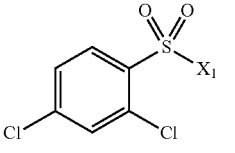 | 1 | |
| Example-084 | 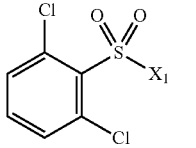 | 1 | |
| Example-085 | 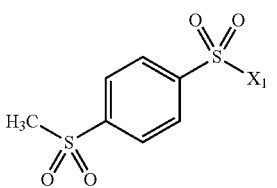 | 1 | |
| Example-086 |  | 1 | |

TABLE 1-continued
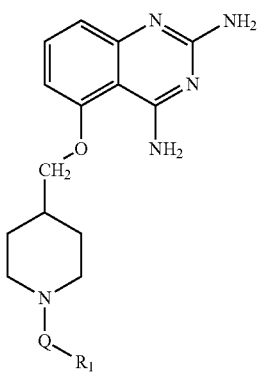
| Example No. | Q + R1 | Promoter Assay EC$_{50}$ 1 = <1 µM, 2 = 1-5 µM 3 = 5-10 µM, 4 = 10-20 µM | hDHFR IC50 A < 20 µM, B = 20-100 µM, C > 100 µM |
|---|---|---|---|
| Example-087 | 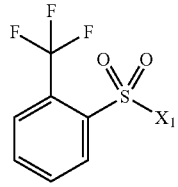 | 1 | |
| Example-088 | 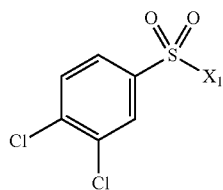 | 1 | |
| Example-089 | 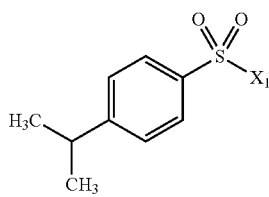 | 1 | |
| Example-090 | 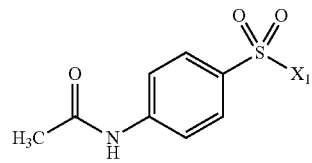 | 1 | |
| Example-091 | 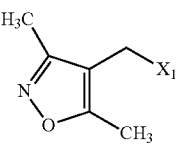 | 1 | |
| Example-092 | 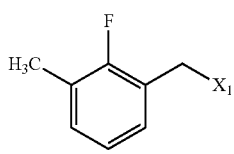 | 1 | C |

TABLE 1-continued
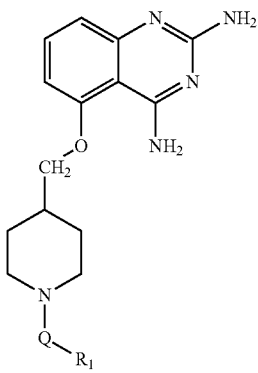
| Example No. | Q + R1 | Promoter Assay EC$_{50}$ 1 = <1 μM, 2 = 1-5 μM 3 = 5-10 μM, 4 = 10-20 μM | hDHFR IC50 A < 20 μM, B = 20-100 μM, C > 100 μM |
|---|---|---|---|
| Example-093 | | 1 | |
| Example-094 | | 1 | |
| Example-095 | | 1 | C |
| Example-096 | | 1 | |
| Example-097 | | 1 | A |
| Example-098 | | 1 | B |
| Example-099 | | 1 | B |
| Example-100 | | 1 | B |

TABLE 1-continued
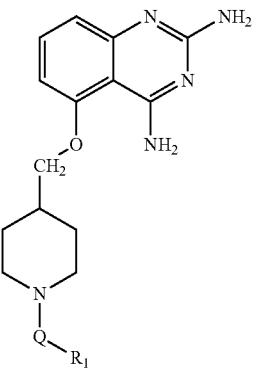
| Example No. | Q + R1 | Promoter Assay EC$_{50}$ 1 = <1 μM, 2 = 1-5 μM 3 = 5-10 μM, 4 = 10-20 μM | hDHFR IC50 A < 20 μM, B = 20-100 μM, C > 100 μM |
|---|---|---|---|
| Example-101 | 2-(trifluoromethoxy)benzyl-X$_1$ | 1 | |
| Example-102 | 4-(trifluoromethoxy)benzyl-X$_1$ | 1 | |
| Example-103 | 3-(trifluoromethoxy)benzyl-X$_1$ | 1 | |
| Example-104 | 2,4-dichlorobenzyl-X$_1$ | 1 | |
| Example-105 | benzo[d][1,3]dioxole-5-carbonyl-X$_1$ | 1 | |
| Example-106 | benzoyl-X$_1$ | 1 | |
| Example-107 | 2,6-difluorobenzoyl-X$_1$ | 1 | |

TABLE 1-continued
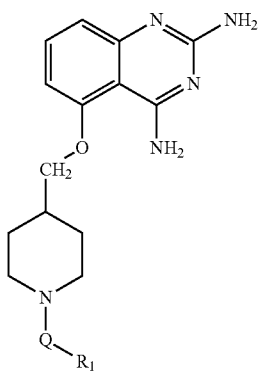
| Example No. | Q + R1 | Promoter Assay EC$_{50}$ 1 = <1 μM, 2 = 1-5 μM 3 = 5-10 μM, 4 = 10-20 μM | hDHFR IC50 A < 20 μM, B = 20-100 μM, C > 100 μM |
|---|---|---|---|
| Example-108 | 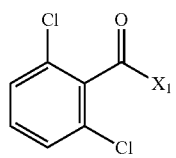 | 1 | |
| Example-109 | 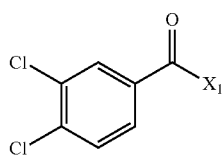 | 1 | |
| Example-110 | 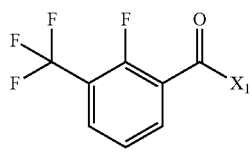 | 1 | |
| Example-111 | 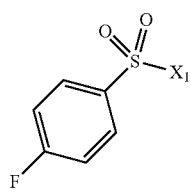 | 1 | |
| Example-112 | 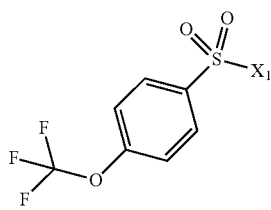 | 1 | |
| Example-113 | 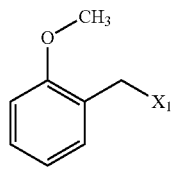 | 1 | C |

TABLE 1-continued

[Structure: quinazoline-2,4-diamine with 5-O-CH2-piperidine-N-Q-R1 substituent]

| Example No. | Q + R1 | Promoter Assay EC$_{50}$ 1 = <1 μM, 2 = 1-5 μM 3 = 5-10 μM, 4 = 10-20 μM | hDHFR IC50 A < 20 μM, B = 20-100 μM, C > 100 μM |
|---|---|---|---|
| Example-114 | 3-methoxybenzyl-X | 1 | |
| Example-115 | 3-(dimethylamino)benzoyl-X$_1$ | 1 | C |
| Example-116 | 3,5-dichlorobenzyl-X$_1$ | 1 | |
| Example-117 | H$_3$C-X$_1$ | 1 | C |
| Example-118 | pyridin-2-ylmethyl-X$_1$ | 1 | |
| Example-119 | pyridin-4-ylmethyl-X$_1$ | 1 | |
| Example-120 | pyridin-3-ylmethyl-X$_1$ | 1 | C |
| Example-121 | cyclobutylmethyl-X$_1$ | 1 | C |
| Example-122 | 3-fluoro-4-methoxybenzyl-X$_1$ | 1 | |

TABLE 1-continued

[Structure: 2,4-diamino-quinazoline with 5-O-CH2-(piperidin-4-yl), piperidine N substituted with Q-R1]

| Example No. | Q + R1 | Promoter Assay EC$_{50}$ 1 = <1 µM, 2 = 1-5 µM, 3 = 5-10 µM, 4 = 10-20 µM | hDHFR IC50 A < 20 µM, B = 20-100 µM, C > 100 µM |
|---|---|---|---|
| Example-123 | 4-(trifluoromethyl)benzyl–X1 | 1 | |
| Example-124 | 4-methoxybenzyl–X1 | 1 | |
| Example-125 | (tetrahydro-2H-pyran-2-yl)methyl–X1 | 2 | C |
| Example-126 | pyrrolidine-1-carbonyl–X1 | 1 | C |
| Example-127 | morpholine-4-carbonyl–X1 | 1 | C |
| Example-128 | (tetrahydrofuran-2-yl)methyl–X1 | 2 | C |
| Example-129 | 4-tert-butylbenzyl–X1 | 1 | |
| Example-130 | 3-(trifluoromethyl)benzyl–X1 | 1 | |

TABLE 1-continued

[Structure: quinazoline-2,4-diamine with 5-O-CH₂-(piperidin-4-yl), N-substituted with Q-R₁]

| Example No. | Q + R1 | Promoter Assay EC₅₀ 1 = <1 μM, 2 = 1-5 μM 3 = 5-10 μM, 4 = 10-20 μM | hDHFR IC50 A < 20 μM, B = 20-100 μM, C > 100 μM |
|---|---|---|---|
| Example-131 | 2-(trifluoromethyl)benzyl | 1 | |
| Example-132 | 3-fluorobenzyl | 1 | |
| Example-133 | 3,5-dimethoxybenzyl | 1 | |
| Example-134 | 3-(dimethylamino)benzyl | 1 | B |
| Example-135 | thiophen-2-ylmethyl | 1 | |
| Example-136 | (1,3-dimethyl-1H-pyrazol-5-yl)methyl | 1 | |
| Example-137 | 3,5-difluorobenzyl | 1 | |

TABLE 1-continued
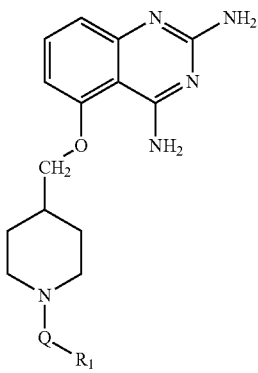
| Example No. | Q + R1 | Promoter Assay EC$_{50}$ 1 = <1 μM, 2 = 1-5 μM 3 = 5-10 μM, 4 = 10-20 μM | hDHFR IC50 A < 20 μM, B = 20-100 μM, C > 100 μM |
|---|---|---|---|
| Example-138 | (CH₃)₂CHCH₂—X₁ | 1 | C |
| Example-139 | (CH₃)₂CHCH₂CH₂—X₁ | 1 | C |
| Example-140 | 2,3-dichlorobenzyl—X₁ | 1 | |
| Example-141 | cyclohexylmethyl—X₁ | 1 | C |
| Example-142 | 2,6-dichlorobenzyl—X₁ | 1 | C |
| Example-143 | 2,5-difluorobenzyl—X₁ | 1 | B |
| Example-144 | H₃C(CH₂)₄CH₂—X₁ | 1 | C |
| Example-145 | thiophen-3-ylmethyl—X₁ | 1 | |

TABLE 1-continued

| Example No. | Q + R1 | Promoter Assay EC$_{50}$ 1 = <1 µM, 2 = 1-5 µM 3 = 5-10 µM, 4 = 10-20 µM | hDHFR IC50 A < 20 µM, B = 20-100 µM, C > 100 µM |
|---|---|---|---|
| Example-146 | 2,5-dimethylbenzyl-X$_1$ | 1 | |
| Example-147 | 2,6-difluorobenzyl-X$_1$ | 1 | C |
| Example-148 | 3,4,5-trifluorobenzyl-X$_1$ | 1 | |
| Example-149 | 4-fluorobenzyl-X$_1$ | 1 | |
| Example-150 | 2,4,5-trifluorobenzoyl-X$_1$ | 1 | |
| Example-151 | piperidin-4-ylmethyl-X$_1$ | 1 | C |
| Example-152 | (1-methylimidazol-2-yl)methyl-X$_1$ | 2 | |

TABLE 1-continued
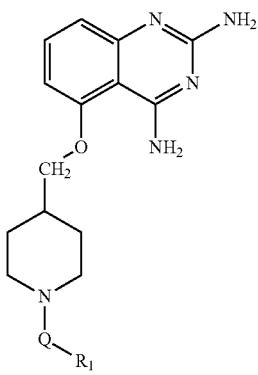
| Example No. | Q + R1 | Promoter Assay EC$_{50}$ 1 = <1 μM, 2 = 1-5 μM, 3 = 5-10 μM, 4 = 10-20 μM | hDHFR IC50 A < 20 μM, B = 20-100 μM, C > 100 μM |
|---|---|---|---|
| Example-222 | 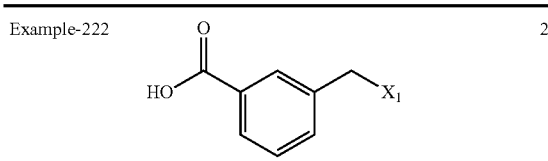 | 2 | |
| Example-223 | 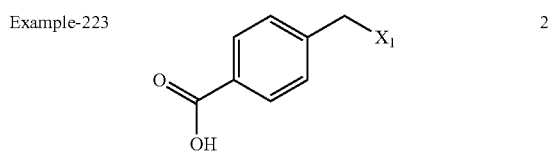 | 2 | |
TABLE 2
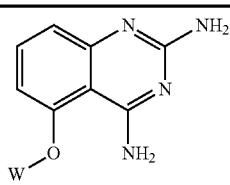
| Example No. | W | Promoter Assay EC50 1 = <1 μM, 2 = 1-5 μM, 3 = 5-10 μM, 4 = 10-20 μM | hDHFR IC50 A < 20 μM, B = 20-100 μM, C > 100 μM |
|---|---|---|---|
| Example-153 | 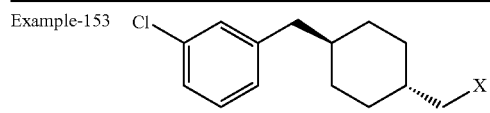 | 1 | A |
| Example-154 | 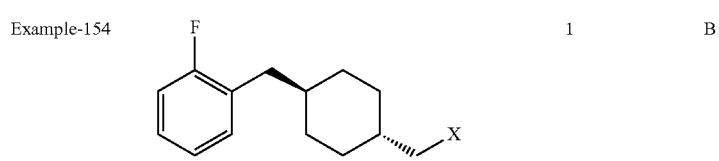 | 1 | B |
| Example-164 | 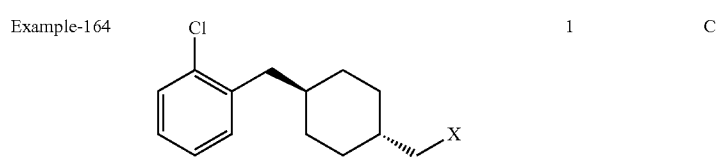 | 1 | C |

TABLE 2-continued
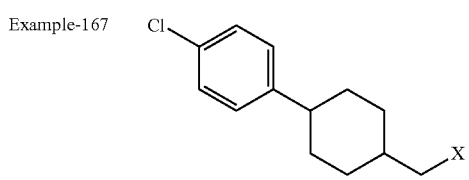
| Example No. | W | Promoter Assay EC50 1 = <1 μM, 2 = 1-5 μM, 3 = 5-10 μM, 4 = 10-20 μM | hDHFR IC50 A < 20 μM, B = 20-100 μM, C > 100 μM |
|---|---|---|---|
| Example-167 | 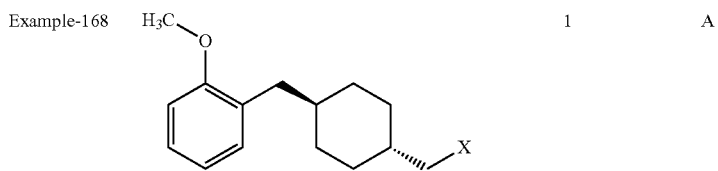 | | |
| Example-168 | | 1 | A |
TABLE 3
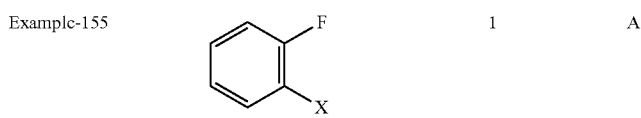
| Example No. | Q + R1 | Promoter Assay EC50 1 = <1 μM, 2 = 1-5 μM, 3 = 5-10 μM, 4 = 10-20 μM | hDHFR IC50 A < 20 μM, B = 20-100 μM, C > 100 μM |
|---|---|---|---|
| Example-155 | 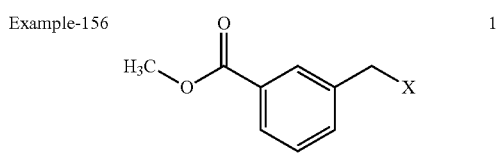 | 1 | A |
| Example-156 | | 1 | |

TABLE 3-continued
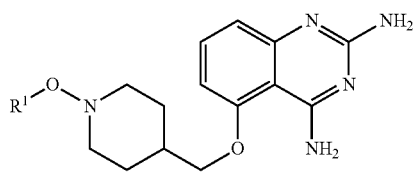
| Example No. | Q + Rl | Promoter Assay EC50 1 = <1 µM, 2 = 1-5 µM, 3 = 5-10 µM, 4 = 10-20 µM | hDHFR IC50 A < 20 µM, B = 20-100 µM, C > 100 µM |
|---|---|---|---|
| Example-157 | 4-(methoxycarbonyl)benzyl-X | 1 | |
| Example-158 | 2,6-dimethylbenzyl-X | 1 | C |
| Example-159 | 2,2-difluoroethyl-X | 1 | C |
| Example-160 | 2-fluoro-6-(trifluoromethyl)benzyl-X | 1 | C |
| Example-161 | 2-chloro-6-fluorobenzyl-X | 1 | C |
| Example-163 | 2-chlorophenyl-X | 1 | |
| Example-165 | 2,2,2-trifluoroethyl-X | 1 | C |

TABLE 4
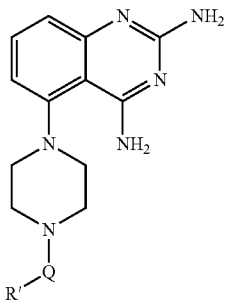
| Example No. | Q + Rl | Promoter Assay EC50 for 2391.003C(P) 1 = <1 μM, 2 = 1-5 μM, 3 = 5-10 μM, 4 = 10-20 μM | hDHFR IC50 A < 20 μM, B = 20-100 μM, C > 100 μM |
|---|---|---|---|
| Example-219 | (CH3)3C-O-C(=O)-X | 2 | |
| Example-220 | H | 1 | |
| Example-169 | benzyl-X | 2 | |
| Example-170 | 2-methylbenzyl-X | | |
| Example-171 | 2-chlorobenzyl-X | | |
| Example-172 | 3-chlorobenzyl-X | | |
| Example-173 | 4-chlorobenzyl-X | 1 | |
| Example-174 | 2,4-dichlorobenzyl-X | | |

TABLE 4-continued
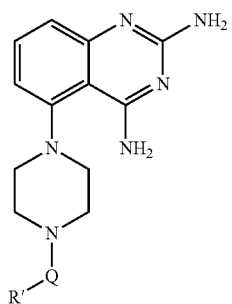
| Example No. | Q + Rl | Promoter Assay EC50 for 2391.003C(P) 1 = <1 μM, 2 = 1-5 μM, 3 = 5-10 μM, 4 = 10-20 μM | hDHFR IC50 A < 20 μM, B = 20-100 μM, C > 100 μM |
|---|---|---|---|
| Example-175 | 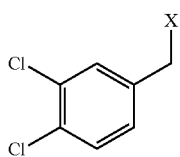 | | |
| Example-176 | 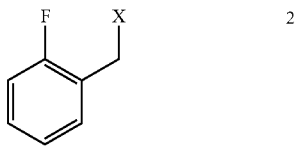 | 2 | |
| Example-177 | 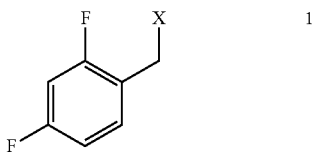 | 1 | |
| Example-178 | 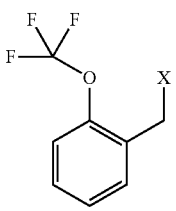 | | |
| Example-179 | 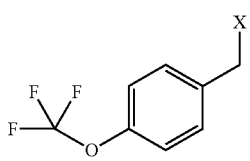 | | |
| Example-180 | 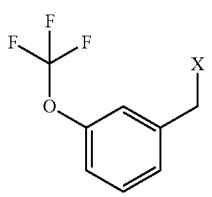 | | |

TABLE 4-continued
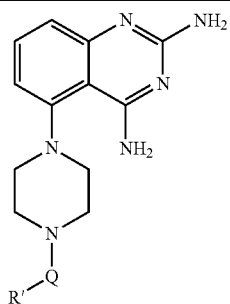
| Example No. | Q + R1 | Promoter Assay<br>EC50 for 2391.003C(P)<br>1 = <1 μM, 2 = 1-5 μM,<br>3 = 5-10 μM,<br>4 = 10-20 μM | hDHFR<br>IC50<br>A < 20 μM,<br>B = 20-100 μM,<br>C > 100 μM |
|---|---|---|---|
| Example-181 | 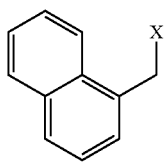 | | |
| Example-182 | 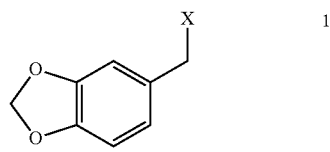 | 1 | |
| Example-183 | 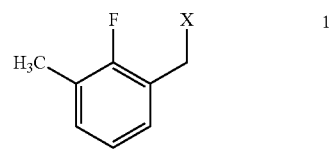 | 1 | |
| Example-184 | 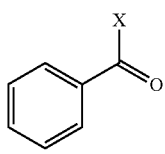 | | |
| Example-185 | 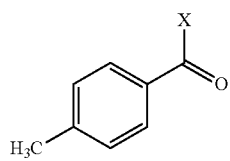 | | |
| Example-186 | 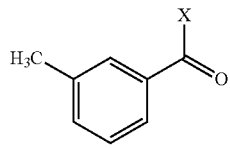 | | |
| Example-187 | 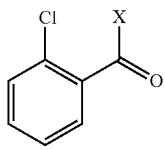 | | |

TABLE 4-continued
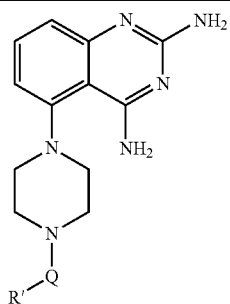
| Example No. | Q + Rl | Promoter Assay EC50 for 2391.003C(P) 1 = <1 µM, 2 = 1-5 µM, 3 = 5-10 µM, 4 = 10-20 µM | hDHFR IC50 A < 20 µM, B = 20-100 µM, C > 100 µM |
|---|---|---|---|
| Example-188 | 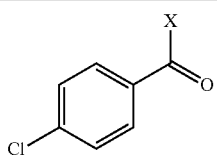 | | |
| Example-189 | 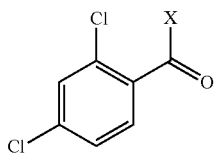 | | |
| Example-190 | 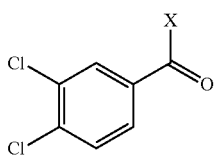 | | |
| Example-191 | 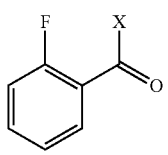 | | |
| Example-192 | 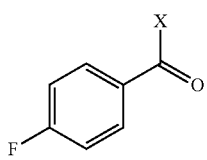 | | |
| Example-193 | 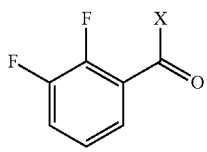 | | |
| Example-194 | 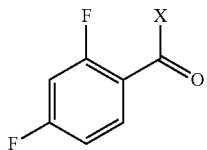 | | |

TABLE 4-continued
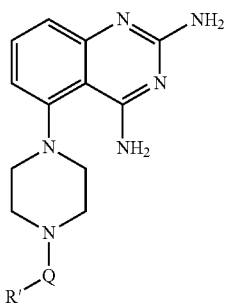
| Example No. | Q + Rl | Promoter Assay EC50 for 2391.003C(P) 1 = <1 μM, 2 = 1-5 μM, 3 = 5-10 μM, 4 = 10-20 μM | hDHFR IC50 A < 20 μM, B = 20-100 μM, C > 100 μM |
|---|---|---|---|
| Example-195 | 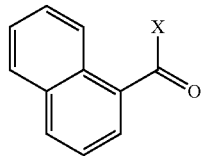 | | |
| Example-196 | 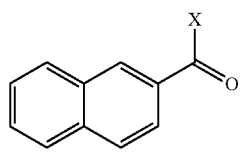 | | |
| Example-197 | 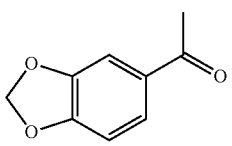 | | |
| Example-198 | 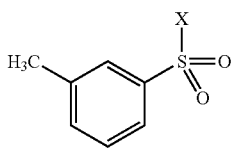 | | |
| Example-199 | 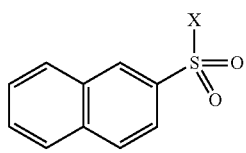 | | |
| Example-200 | 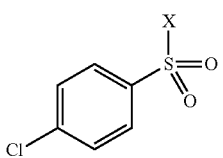 | | |
| Example-201 | 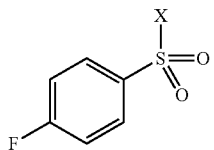 | | |

TABLE 4-continued
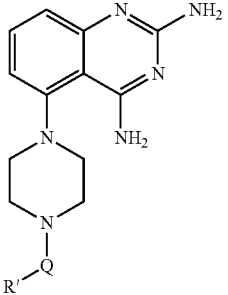
| Example No. | Q + Rl | Promoter Assay EC50 for 2391.003C(P) 1 = <1 μM, 2 = 1-5 μM, 3 = 5-10 μM, 4 = 10-20 μM | hDHFR IC50 A < 20 μM, B = 20-100 μM, C > 100 μM |
|---|---|---|---|
| Example-202 | 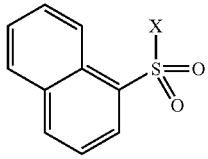 | | |
| Example-203 | 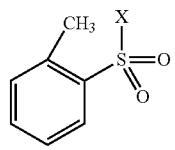 | | |
| Example-204 | 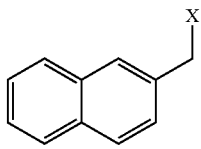 | 2 | |
TABLE 5
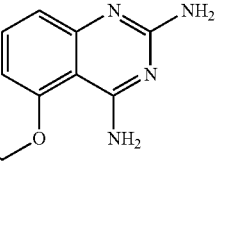
| Example No. | Q + Rl | Promoter Assay EC50 1 = <1 μM, 2 = 1-5 μM, 3 = 5-10 μM, 4 = 10-20 μM | hDHFR IC50 A < 20 μM, B = 20-100 μM, C > 100 μM |
|---|---|---|---|
| Example-205 | 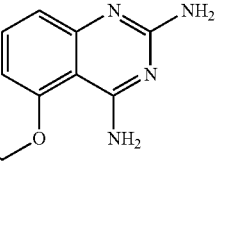 | 1 | A |

TABLE 5-continued

[Structure: quinazoline-2,4-diamine with 5-O-CH₂CH₂-piperazine-N-piperazine-O-R¹]

| Example No. | Q + Rl | Promoter Assay EC50<br>1 = <1 µM, 2 = 1-5 µM,<br>3 = 5-10 µM,<br>4 = 10-20 µM | hDHFR IC50<br>A < 20 µM,<br>B = 20-100 µM,<br>C > 100 µM |
|---|---|---|---|
| Example-206 | 2-fluorophenylsulfonyl-X | 1 | A |
| Example-207 | 2,4-difluorobenzoyl-X | 1 | B |
| Example-208 | benzo[d][1,3]dioxole-5-carbonyl-X | 1 | A |
| Example-209 | phenylsulfonyl-X | 1 | A |
| Example-210 | 2,4-difluorophenylsulfonyl-X | 1 | A |
| Example-211 | 3,4-dichlorophenylsulfonyl-X | 1 | A |
| Example-212 | 3,4-dichlorobenzoyl-X | 1 | A |
| Example-213 | benzoyl-X | 1 | A |

TABLE 5-continued

[Structure: quinazoline-2,4-diamine with 5-O-CH2CH2-piperazine-N-O-R1]

| Example No. | Q + Rl | Promoter Assay EC50  1 = <1 μM, 2 = 1-5 μM, 3 = 5-10 μM, 4 = 10-20 μM | hDHFR IC50  A < 20 μM, B = 20-100 μM, C > 100 μM |
|---|---|---|---|
| Example-214 | 3-chlorobenzoyl-X | 1 | A |
| Example-215 | 2-fluorobenzoyl-X | 1 | A |
| Example-216 | 2-fluorobenzyl-X | 1 | B |
| Example-217 | 2,4-difluorobenzyl-X | 1 | B |
| Example-218 | 3-chloro-2-fluorobenzyl-X | 1 | B |

TABLE 6

| Example No. | Structure | Promoter Assay EC50 1 = <1 μM, 2 = 1-5 μM, 3 = 5-10 μM, 4 = 10-20 μM |
|---|---|---|
| Example-221 | [2-fluorobenzyl N-oxide piperidine-4-methyloxy-quinazoline-2,4-diamine] | 2 |

TABLE 6-continued

| Example No. | Structure | Promoter Assay EC50 1 = <1 μM, 2 = 1-5 μM, 3 = 5-10 μM, 4 = 10-20 μM |
|---|---|---|
| Example-224 | (structure) | 1 |
| Example-225 | (structure) | 1 |
| Example-226 | (structure) | 1 |
| Example-227 | (structure) | 1 |

The present invention includes compounds of formula I (e.g., any of the compounds of Examples 1-227), in the form of salts, in particular acid addition salts. Suitable salts include those formed with both organic and inorganic acids. Such acid addition salts will normally be pharmaceutically acceptable, although non-pharmaceutically acceptable salts may be of utility in the preparation and purification of the compound in question. Thus, preferred salts include those formed from hydrochloric, hydrobromic, sulphuric, citric, tartaric, phosphoric, lactic, pyruvic, acetic, succinic, oxalic, fumaric, maleic, oxaloacetic, methanesulphonic, ethanesulphonic, p-toluenesulphonic, benzenesulphonic and isethionic acids. Salts of the compounds of the invention can be made by reacting the appropriate compound in the form of the free base with the appropriate acid.

While it may be possible for the compounds of formula I to be administered as the raw chemical, it is preferable to present them as a pharmaceutical composition. According to a further aspect, the present invention provides a pharmaceutical composition comprising a compound of formula I, II, or III, or a pharmaceutically acceptable salt or solvate thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association a compound of the invention or a pharmaceutically acceptable salt or solvate thereof ("active ingredient") with the carrier, which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent.

Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

Formulations for parenteral administration include aqueous and non-aqueous sterile injection solutions, which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

Preferred unit dosage formulations are those containing an effective dose, as hereinbelow recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

The compounds of the invention may be administered at a dose from 0.01 to 250 mg/kg per day. The dose range for adult humans is generally from 0.05 mg to 10 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg. The precise amount of compound administered to a patient will be the responsibility of the attendant physician. The dose employed will depend on a number of factors, including the age and sex of the patient and the severity of the disorder. Also, the route of administration may vary depending on the condition and its severity.

Combination therapy is possible with any combination of agents that improve SMA; those that operate by a mechanism independent of promotion of SMN2 may offer additional advantages. Combination therapy can be achieved by administering two or more agents, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. While in many cases it is desirable that the two or more agents used in a combination therapy be present in within the patient's body at the same time, this need not be so. Combination therapy can also include two or more administrations of one or more of the agents used in the combination. For example, if agent X and agent Y are used in a combination, one could administer them sequentially in any combination one or more times, e.g., in the order X—Y—X, X—X—Y, Y—X—Y, Y—Y—X, X—X—Y—Y, etc.

Examples of drugs that improve SMA include, but are not limited to valproic acid, hydroxybutyrate, phenylbutyrate, phenylbutyrate derivatives, histone deacetylase (HDAC) inhibitors and methylase inhibitors. Exemplary HDAC inhibitors include, but are not limited to, valproic acid, hydroxybutyrate, phenylbutyrate, phenylbutyrate derivatives, trichostatin A (TSA) and suberoylanilide hydroxamic acid (SAHA). An exemplary methylase inhibitor is 5-azacytidine. Other HDAC and methylase inhibitors would be obvious to one of ordinary skill. Effects of the quinazoline derivatives of formula I on SMN2 promoter induction are additive and/or synergistic with HDAC inhibitors and with methylese inhibitors.

Each of the patents, patent applications, patent publications, and references mentioned herein is hereby incorporated by reference in its entirety.

We claim:
1. A 2,4-diaminoquinazoline compound of formula (I):

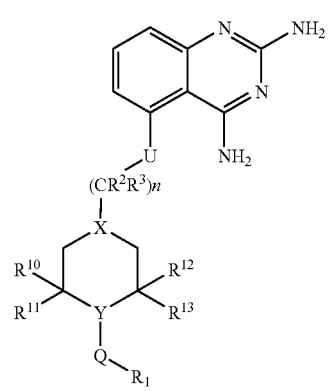

or a pharmaceutically acceptable salt thereof;
wherein
U is —O—;
$R^2$ and $R^3$ are independently selected in each occurrence from H and lower alkyl;
n is 0, 1, 2, or 3;
X is selected from the group consisting of N and CH;
Y is selected from the group consisting of N, CH, C(OH) and N→O;
$R^{10}$, $R^{11}$, $R^{12}$ and $R^{13}$ are independently selected from H and lower alkyl, or, taken together, $R^{10}$ and $R^{11}$ or $R^{12}$ and $R^{13}$ are =O;
Q is selected from the group consisting of —CH$_2$—, —C(=O)—, —CH$_2$(C=O)—, —SO$_2$—, —CR$^{14}$R$^{15}$—, —C(=O)CH$_2$S— and a direct bond, wherein $R^{14}$ and $R^{15}$ are independently selected from hydrogen and lower alkyl; and
$R^1$ is selected from the group consisting of H, alkyl, alkoxy, carbocycle, heterocyclyl, fluoroalkyl, alkoxyalkyl, substituted carbocycle and substituted heterocyclyl;
wherein substituted carbocycle or heterocyclyl refers to a carbocycle or heterocyclyl wherein up to three H atoms are replaced with a substituent independently selected from the group consisting of halogen, haloalkyl, hydroxy, loweralkoxy, carboxy, carboalkoxy, carboxamido, cyano, carbonyl, nitro, amino, alkylamino, dialkylamino, mercapto, alkylthio, sulfoxide, sulfone, acylamino, amidino, phenyl, benzyl, halobenzyl, heteroaryl, phenoxy, benzyloxy, heteroaryloxy, benzoyl, halobenzoyl, and loweralkylhydroxy.

2. A compound according to claim 1, or a pharmaceutically acceptable salt thereof, wherein X is CH and Y is N.

3. A compound according to claim 2, or a pharmaceutically acceptable salt thereof, wherein $R^{10}$, $R^{11}$, $R^{12}$ and $R^{13}$ are H, $R^2$ and $R^3$ are H and n is 1.

4. A compound according to claim 2, or a pharmaceutically acceptable salt thereof, wherein $R^{10}$ and $R^{11}$ together are =O and $R^{12}$ and $R^{13}$ are hydrogen.

5. A compound according to claim 2, or a pharmaceutically acceptable salt thereof, wherein $R^{10}$ and $R^{11}$ together are =O and $R^{12}$ and $R^{13}$ together are =O.

6. A compound according to claim 1, or a pharmaceutically acceptable salt thereof, wherein $R^2$ and $R^3$ are H.

7. A compound according to claim 6, or a pharmaceutically acceptable salt thereof, wherein n is 1 or 2.

8. A compound according to claim 7, or a pharmaceutically acceptable salt thereof, wherein X and Y are both CH.

9. A compound according to claim 8, or a pharmaceutically acceptable salt thereof, wherein $R^{10}$, $R^{11}$, $R^{12}$ and $R^{13}$ are H.

10. A compound according to claim 9, or a pharmaceutically acceptable salt thereof, wherein Q is $CH_2$ or a direct bond.

11. A compound according to claim 10, or a pharmaceutically acceptable salt thereof, wherein $R^1$ is carbocycle, substituted carbocycle, or fluoroalkyl.

12. A compound according to claim 11, or a pharmaceutically acceptable salt thereof, wherein $R^1$ is substituted carbocycle and the substituted carbocycle is monosubstituted or disubstituted phenyl.

13. A compound according to claim 1, or a pharmaceutically acceptable salt thereof, wherein Q is a direct bond or $CH_2$ and $R^1$ is carbocycle, substituted carbocycle or fluoroalkyl, with the proviso that the compound is not 5-[1-(3,4-dichlorobenzyl)-piperidin-4-ylmethoxy]-quinazoline-2,4-diamine.

14. A compound according to claim 1, or a pharmaceutically acceptable salt thereof, wherein X and Y are N.

15. A compound according to claim 14, or a pharmaceutically acceptable salt thereof, wherein $R^{10}$, $R^{11}$, $R^{12}$ and $R^{13}$ are H.

16. A 2,4-diaminoquinazoline compound according to claim 1 of formula (II):

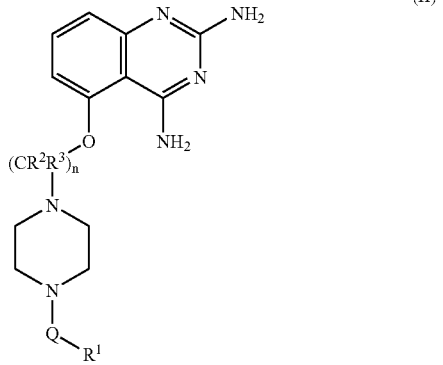

or a pharmaceutically acceptable salt thereof;
wherein
Q is selected from the group consisting of: —$CH_2$—; —C(=O)—; —$SO_2$—; —$CH_2$C(=O); —C(=O)$CH_2$S—; and a direct bond;
$R^1$ is selected from the group consisting of H, alkyl, alkoxy, carbocycle, heterocyclyl, substituted carbocycle, substituted heterocyclyl and fluoroalkyl;
$R^2$ and $R^3$ are independently selected from the group consisting of H and lower alkyl; and
n is 2 or 3.

17. A compound according to claim 16, or a pharmaceutically acceptable salt thereof, wherein n is 2.

18. A compound according to claim 17, or a pharmaceutically acceptable salt thereof, wherein $R^2$ and $R^3$ are H.

19. A compound according to claim 17, or a pharmaceutically acceptable salt thereof, wherein $R^2$ is H and $R^3$ is H or $CH_3$.

20. A compound according to either claim 18 or claim 19, or a pharmaceutically acceptable salt thereof, wherein Q is $CH_2$ or —C(=O)—.

21. A compound according to claim 20, or a pharmaceutically acceptable salt thereof, wherein $R^1$ is carbocycle or substituted carbocycle.

22. A compound according to claim 21, or a pharmaceutically acceptable salt thereof, wherein $R^1$ is other than phenyl or halophenyl.

23. A compound according to claim 16, or a pharmaceutically acceptable salt thereof, wherein Q is —$SO_2$— or —C(=O)—.

24. A compound according to claim 23, or a pharmaceutically acceptable salt thereof, wherein $R^2$ and $R^3$ are H and n is 2.

25. A compound according to claim 16, or a pharmaceutically acceptable salt thereof, wherein $R^1$ is carbocycle or substituted carbocycle.

26. A compound according to claim 25, or a pharmaceutically acceptable salt thereof, wherein $R^1$ is substituted carbocycle and the substituted carbocycle is monosubstituted or disubstituted phenyl.

27. A 2,4-diaminoquinazoline compound according to claim 1 of formula (III):

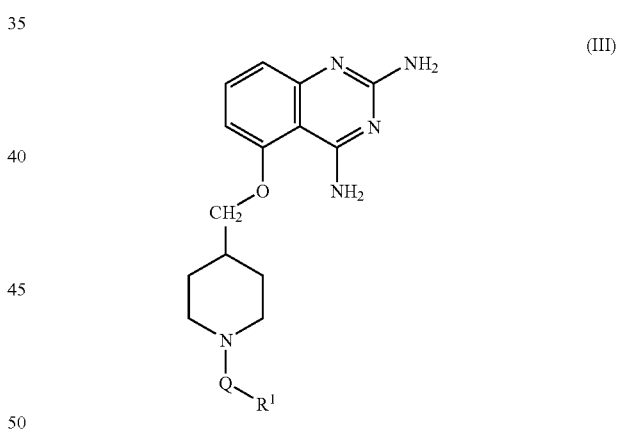

or a pharmaceutically acceptable salt thereof;
wherein
Q is selected from the group consisting of —$CH_2$—, —C(=O)—, —$SO_2$—, —$CH_2$C(=O)— and —$SCH_2$C(=O)—;
$R^1$ is selected from the group consisting of H, alkyl, alkoxy, carbocycle, heterocyclyl, substituted carbocycle and substituted heterocyclyl, with the proviso that when $R^1$ is substituted carbocycle it is not a 3,4-dichlorophenyl.

28. A compound according to claim 27, or a pharmaceutically acceptable salt thereof, wherein $R^1$ is carbocycle selected from the group consisting aryl and cycloalkyl, or substituted carbocycle selected from the group consisting of substituted cycloalkyl and substituted aryl.

29. A 2,4-diaminoquinazoline compound according to claim 1 of formula (III):

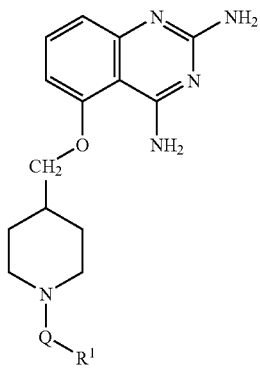

or a pharmaceutically acceptable salt thereof;
wherein
Q is selected from the group consisting of —CH$_2$—, —C(=O)—, —SO$_2$—, —CH$_2$C(=O)— and —SCH$_2$C(=O)—;
R$^1$ is selected from the group consisting of H, alkyl, alkoxy, carbocycle, heterocyclyl, substituted carbocycle and substituted heterocyclyl,
with the proviso that when R$^1$ is a substituted carbocycle it is a monosubstituted phenyl or a 2,6-dihalo substituted phenyl.

30. A compound according to claim 29, or a pharmaceutically acceptable salt thereof, wherein Q is —CH$_2$— and R$^1$ is selected from the group consisting of alkyl, carbocycle, substituted carbocycle, heteroaryl and substituted heteroaryl.

31. A compound according to claim 30, or a pharmaceutically acceptable salt thereof, wherein R$^1$ is substituted carbocycle.

32. A compound according to claim 31, or a pharmaceutically acceptable salt thereof, wherein the R$^1$ is other than 3-halo substituted phenyl.

33. A compound according to claim 31, or a pharmaceutically acceptable salt thereof, wherein the substituted carbocycle is 2-halo substituted phenyl or 2,6-dihalo substituted phenyl.

34. A 2,4-diaminoquinazoline compound according to claim 1 of formula (III):

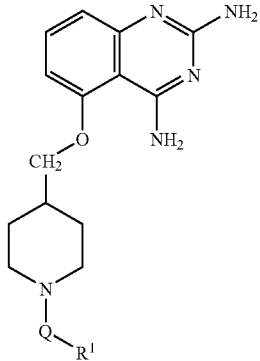

or a pharmaceutically acceptable salt thereof;
wherein
Q is selected from the group consisting of —CH$_2$—, —C(=O)—, —SO$_2$—, —CH$_2$C(=O)— and —SCH$_2$C(=O)—;

R$^1$ is selected from the group consisting of H, alkyl, alkoxy, carbocycle, heterocyclyl, and substituted heterocyclyl.

35. A compound according to claim 34, or a pharmaceutically acceptable salt thereof, wherein Q is CH$_2$ and R$^1$ is selected from the group consisting of alkyl, carbocycle, heteroaryl and substituted heteroaryl.

36. A compound according to claim 35, or a pharmaceutically acceptable salt thereof, wherein R$^1$ is heteroaryl or substituted heteroaryl and the heteroaryl is pyridine.

37. A compound according to claim 1, or a pharmaceutically acceptable salt thereof, with the proviso that the compound is not chosen from among the following compounds:
5-[1-(3,4-dichlorobenzyl)-piperidin-4-ylmethoxy]-quinazoline-2,4-diamine;
5-(Cyclohexylmethoxy)quinazoline-2,4-diamine;
5-(1-Cyclohexyl-ethoxy)-quinazoline-2,4-diamine;
5-(1-Cyclohexylpropoxy)-quinazoline-2,4-diamine;
5-(1-Cyclohexyl-butoxy)-quinazoline-2,4-diamine;
5-(Piperidin-1-yl)quinazoline-2,4-diamine;
5-(Piperidin-4-ylmethoxy)-quinazoline-2,4-diamine;
4-(2,4-diamino-quinazolin-5-yloxymethyl)-piperidin-1-carboxylic acid tert-butyl ester;
(4-Chlorophenyl)-[4-(2,4-diamino-quinazolin-5-yloxymethyl)piperidin-1-yl]-methanone;
(2-Chlorophenyl)-[4-(2,4-diamino-quinazolin-5-yloxymethyl)piperidin-1-yl]-methanone;
(3-Chlorophenyl)-[4-(2,4-diamino-quinazolin-5-yloxymethyl)piperidin-1-yl]-methanone;
[4-(2,4-Diaminoquinazolin-5-ylmethoxymethyl)piperidin-1-yl]-(3-iodophenyl)methanone;
[4-(2,4-Diaminoquinazolin-5-ylmethoxymethyl)piperidin-1-yl]-(4-iodophenyl)methanone; and
[4-(2,4-Diaminoquinazolin-5-ylmethoxymethyl)piperidin-1-yl]-(2-iodophenyl)methanone
and pharmaceutically acceptable salts thereof.

38. A pharmaceutical composition for treating spinal muscular atrophy comprising a pharmaceutically acceptable carrier and a therapeutically effective amount of a 2,4-diaminoquinazoline compound according to claim 1, or a pharmaceutically acceptable salt thereof.

39. A method for treating spinal muscular atrophy comprising administering to a patient in need thereof a therapeutically effective amount of a 2,4-diaminoquinazoline compound according to claim 1, or a pharmaceutically acceptable salt thereof.

40. A method according to claim 39, wherein the compound is:
5-[(1-(2-Fluorobenzyl)piperidin-4-ylmethoxy]quinazoline-2,4-diamine;
or a pharmaceutically acceptable salt thereof.

41. A method according to claim 39, wherein the compound is:
5-[1-(2-Chloro-6-fluorobenzyl)piperidin-4-ylmethoxy]quinazoline-2,4-diamine;
or a pharmaceutically acceptable salt thereof.

42. A method according to claim 39, wherein the compound is:
5-[1-(2,6-dichlorobenzyl)piperidin-4-ylmethoxy]quinazoline-2,4-diamine;
or a pharmaceutically acceptable salt thereof.

43. A compound selected from the group consisting of:
5-[4-(2-Chlorobenzyl)cyclohexylmethoxy]quinazoline-2,4-diamine;
5-[4-(3-Chlorobenzyl)cyclohexylmethoxy]quinazoline-2,4-diamine;
5-[4-(2-Fluorobenzyl)cyclohexylmethoxy]quinazoline-2,4-diamine;
5-[4-(4-Chlorophenyl)cyclohexylmethoxy]quinazoline-2,4-diamine;
5-{2-[4-(2-Fluoro-benzenesulfonyl)-piperazin-1-yl]-ethoxy}-quinazoline-2,4-diamine;

5-{2-[4-(2,4-Difluoro-benzenesulfonyl)-piperazin-1-yl]-
  ethoxy}-quinazoline-2,4-diamine;
5-{2-[4-(3,4-Dichloro-benzenesulfonyl)-piperazin-1-yl]-
  ethoxy}-quinazoline-2,4-diamine;
Benzo[1,3]dioxol-5-yl-{4-[2-(2,4-diamino-quinazolin-5-
  yloxy)-ethyl]-piperazin-1-yl}-methanone; and
5-[(1-(Pyridine-3-ylmethyl)piperidin-4-ylmethoxy]
  quinazoline-2,4-diamine;
and pharmaceutically acceptable salts thereof.

44. A compound according to claim 43, wherein the compound is selected from the group consisting of:
5-[4-(2-Chlorobenzyl)cyclohexylmethoxy]quinazoline-2,4-diamine;
5-[4-(3-Chlorobenzyl)cyclohexylmethoxy]quinazoline-2,4-diamine;
5-[4-(2-Fluorobenzyl)cyclohexylmethoxy]quinazoline-2,4-diamine; and
5-[4-(4-Chlorophenyl)cyclohexylmethoxy]quinazoline-2,4-diamine;
and pharmaceutically acceptable salts thereof.

45. A compound according to claim 43, or a pharmaceutically acceptable salt thereof, wherein the compound is selected from the group consisting of:
5-{2-[4-(2-Fluoro-benzenesulfonyl)-piperazin-1-yl]-
  ethoxy}-quinazoline-2,4-diamine;
5-{2-[4-(2,4-Difluoro-benzenesulfonyl)-piperazin-1-yl]-
  ethoxy}-quinazoline-2,4-diamine; and
5-{2-[4-(3,4-Dichloro-benzenesulfonyl)-piperazin-1-yl]-
  ethoxy}-quinazoline-2,4-diamine;
and pharmaceutically acceptable salts thereof.

46. A compound according to claim 43, or a pharmaceutically acceptable salt thereof, wherein the compound is Benzo[1,3]dioxol-5-yl-{4-[2-(2,4-diamino-quinazolin-5-yloxy)-ethyl]-piperazin-1-yl}-methanone or a pharmaceutically acceptable salt thereof.

47. A compound according to claim 43, wherein the compound is
5-[(1-(pyridine-3-ylmethyl)piperidin-4-ylmethoxy]
  quinazoline-2,4-diamine or a pharmaceutically acceptable salt thereof.

48. A compound selected from the group consisting of:
5-[(1-(2-Fluorobenzyl)piperidin-4-ylmethoxy]quinazoline-2,4-diamine;
5-[1-(2-Chloro-6-fluorobenzyl)piperidin-4-ylmethoxy]
  quinazoline-2,4-diamine; and
5-[1-(2,6-dichlorobenzyl)piperidin-4-ylmethoxy]
  quinazoline-2,4-diamine;
and pharmaceutically acceptable salts thereof.

49. A compound according to claim 48, wherein the compound is:
5-[(1-(2-Fluorobenzyl)piperidin-4-ylmethoxy]quinazoline-2,4-diamine;
or a pharmaceutically acceptable salt thereof.

50. A compound according to claim 48, wherein the compound is:
5-[1-(2-Chloro-6-fluorobenzyl)piperidin-4-ylmethoxy]
  quinazoline-2,4-diamine;
or a pharmaceutically acceptable salt thereof.

51. A compound according to claim 48, wherein the compound is:
5-[1-(2,6-dichlorobenzyl)piperidin-4-ylmethoxy]
  quinazoline-2,4-diamine;
or a pharmaceutically acceptable salt thereof.

52. A compound selected from the group consisting of:
5-[1-(2-fluorobenzyl)piperidin-4-ylmethoxy]quinazoline-2,4-diamine;
5-[1-(3-chlorobenzyl)piperidin-4-ylmethoxy]quinazoline-2,4-diamine;
5-[1-(2-chlorobenzyl)piperidin-4-ylmethoxy]quinazoline-2,4-diamine;
5-[1-(4-chlorobenzyl)piperidin-4-ylmethoxy]quinazoline-2,4-diamine;
5-[1-(1-naphthalen-1-ylmethyl)piperidin-4-ylmethoxy]
  quinazoline-2,4-diamine;
5-[1-(2-naphthalen-1-ylmethylpiperidin-4-ylmethoxy]
  quinazoline-2,4-diamine;
5-[1-(2-methylbenzyl)piperidin-4-ylmethoxy]quinazoline-2,4-diamine;
5-[1-(3-methylbenzyl)piperidin-4-ylmethoxy]quinazoline-2,4-diamine;
5-[1-(4-methylbenzyl)piperidin-4-ylmethoxy]quinazoline-2,4-diamine;
5-[1-(2,4-difluorobenzyl)piperidin-4-ylmethoxy]
  quinazoline-2,4-diamine;
5-[1-(3,4-difluorobenzyl)piperidin-4-ylmethoxy]
  quinazoline-2,4-diamine;
5-[1-(2,3-difluorobenzyl)piperidin-4-ylmethoxy]
  quinazoline-2,4-diamine;
[4-(2,4-diaminoquinazolin-5-yloxymethyl)piperidin-1-yl](2-fluorophenyl)methanone;
(3-chlorophenyl)-[4-(2,4-diaminoquinazolin-5-yloxymethyl)piperidin-1-yl]methanone;
(2-chlorophenyl)-[4-(2,4-diaminoquinazolin-5-yloxymethyl)piperidin-1-yl]methanone;
(4-chlorophenyl)-[4-(2,4-diaminoquinazolin-5-yloxymethyl)piperidin-1-yl]methanone;
[4-(2,4-diaminoquinazolin-5-yloxymethyl)piperidin-1-yl](2,6-dimethoxyphenyl)methanone;
[4-(2,4-diaminoquinazolin-5-yloxymethyl)piperidin-1-yl]naphthalen-2-yl-methanone;
[4-(2,4-diaminoquinazolin-5-yloxymethyl)piperidin-1-yl]-o-tolylmethanone;
[4-(2,4-diaminoquinazolin-5-yloxymethyl)piperidin-1-yl]-m-tolylmethanone;
[4-(2,4-diaminoquinazolin-5-yloxymethyl)piperidin-1-yl]-p-tolylmethanone;
[4-(2,4-diaminoquinazolin-5-yloxymethyl)piperidin-1-yl]-(2,4-difluorophenyl)methanone;
[4-(2,4-diaminoquinazolin-5-yloxymethyl)piperidin-1-yl]-(3,4-difluorophenyl)methanone;
[4-(2,4-diaminoquinazolin-5-yloxymethyl)piperidin-1-yl]-(2,3-difluorophenyl)methanone;
5-[1-(2-fluorobenzenesulfonyl)piperidin-4-ylmethoxy]
  quinazoline-2,4-diamine;
5-[1-(3-chlorobenzenesulfonyl)piperidin-4-ylmethoxy]
  quinazoline-2,4-diamine;
5-[1-(2-chlorobenzenesulfonyl)piperidin-4-ylmethoxy]
  quinazoline-2,4-diamine;
5-[1-(4-chlorobenzenesulfonyl)piperidin-4-ylmethoxy]
  quinazoline-2,4-diamine;
5-[1-(naphthalene-1-sulfonyl)piperidin-4-ylmethoxy]
  quinazoline-2,4-diamine;
5-[1-(naphthalene-2-sulfonyl)piperidin-4-ylmethoxy]
  quinazoline-2,4-diamine;
5-[1-(toluene-2-sulfonyl)piperidin-4-ylmethoxy]quinazoline-2,4-diamine;
5-[1-(toluene-3-sulfonyl)piperidin-4-ylmethoxy]quinazoline-2,4-diamine;
5-[1-(toluene-4-sulfonyl)piperidin-4-ylmethoxy]quinazoline-2,4-diamine;
5-[4-(2,4-difluorobenzenesulfonyl)-piperidin-4-ylmethoxy]quinazoline-2,4-diamine;
5-[4-(3,4-difluorobenzenesulfonyl)-piperidin-4-ylmethoxy]quinazoline-2,4-diamine;
5-(Piperidin-4-ylmethoxy)quinazoline-2,4-diamine;
tert-butyl 4-((2,4-diaminoquinazolin-5-yloxy)methyl)piperidine-1-carboxylate;
5-[1-(3,4-dichlorobenzyl)piperidin-4-ylmethoxy]
  quinazoline-2,4-diamine;
[4-(2,4-diaminoquinazolin-5-yloxymethyl)piperidin-1-yl](3-iodophenyl)-methanone;
[4-(2,4-diaminoquinazolin-5-yloxymethyl)piperidin-1-yl](4-iodophenyl)-methanone;

[4-(2,4-diaminoquinazolin-5-yloxymethyl)piperidin-1-yl](2-iodophenyl)-methanone;
5-[1-(2-iodobenzyl)piperidin-4-ylmethoxy]quinazoline-2,4-diamine;
5-[1-(3-iodobenzyl)piperidin-4-ylmethoxy]quinazoline-2,4-diamine;
5-[1-(4-iodobenzyl)piperidin-4-ylmethoxy]quinazoline-2,4-diamine;
1-(4-((2,4-diaminoquinazolin-5-yloxy)methyl)piperidin-1-yl)-2-(4-methoxyphenyl)ethanone;
[4-(2,4-diaminoquinazolin-5-yloxymethyl)piperidin-1-yl](3-fluorophenyl)-methanone;
5-({1-[4-(methylsulfonyl)benzyl]piperidin-4-yl}methoxy)quinazoline-2,4-diamine;
1-(4-((2,4-diaminoquinazolin-5-yloxy)methyl)piperidin-1-yl)-2,2-dimethylpropan-1-one;
(4-((2,4-diaminoquinazolin-5-yloxy)methyl)piperidin-1-yl)(4-methylcyclohexyl)methanone;
(cyclopropyl){4-[(2,4-diaminoquinazolin-5-yloxy)methyl]piperidin-1-yl}methanone;
(2-chloro-pyridin-5-yl) {4-[(2,4-diaminoquinazolin-5-yloxy)methyl]piperidin-1-yl}methanone;
{4-[(2,4-diaminoquinazolin-5-yloxy)methyl]piperidin-1-yl}(2,5-difluorophenyl)methanone;
2-(bicyclo[2.2.1]heptan-2-yl)-1-(4-((2,4-diamino-quinazolin-5-yloxy)methyl)piperidin-1-yl)ethanone;
{4-[(2,4-diaminoquinazolin-5-yloxy)methyl]piperidin-1-yl}(3,5-dichlorophenyl)methanone;
(4-((2,4-diaminoquinazolin-5-yloxy)methyl)piperidin-1-yl)(thiophen-2-yl)methanone;
{4-[(2,4-diaminoquinazolin-5-yloxy)methyl]piperidin-1-yl}(4-methoxyphenyl)methanone;
{4-[(2,4-diaminoquinazolin-5-yloxy)methyl]piperidin-1-yl}(furan-2-yl)methanone;
{-4-[(2,4-diaminoquinazolin-5-yloxy)methyl]piperidin-1-yl}(naphthalen-1yl)methanone;
(4-((2,4-diaminoquinazolin-5-yloxy)methyl)piperidin-1-yl)(5-methylisoxazol-3-yl)methanone;
{4-[(2,4-diaminoquinazolin-5-yloxy)methyl]piperidin-1-yl}(2,4-dichlorophenyl)methanone;
{4-[(2,4-diaminoquinazolin-5-yloxy)methyl]piperidin-1-yl}(2-trifluoromethoxyphenyl)methanone;
{4-[(2,4-diaminoquinazolin-5-yloxy)methyl]piperidin-1-yl}(4-fluorophenyl)methanone;
{4-[(2,4-diaminoquinazolin-5-yloxy)methyl]piperidin-1-yl}(4-trifluoromethoxyphenyl)methanone;
{4-[(2,4-diaminoquinazolin-5-yloxy)methyl]piperidin-1-yl}(4-ethylphenyl)methanone;
{4-[(2,4-diaminoquinazolin-5-yloxy)methyl]piperidin-1-yl}(3-trifluoromethoxyphenyl)methanone;
(cyclobutyl){4-[(2,4-diaminoquinazolin-5-yloxy)methyl]piperidin-1-yl}methanone;
1-(4-((2,4-diaminoquinazolin-5-yloxy)methyl)piperidin-1-yl)-2-ethylbutan-1-one;
1-(4-((2,4-diaminoquinazolin-5-yloxy)methyl)piperidin-1-yl)-2-methylbutan-1-one;
(cyclopentyl){4-[(2,4-diaminoquinazolin-5-yloxy)methyl]piperidin-1-yl}methanone;
1-(4-((2,4-diaminoquinazolin-5-yloxy)methyl)piperidin-1-yl)-2-(phenylthio)ethanone;
{4-[(2,4-diaminoquinazolin-5-yloxy)methyl]piperidin-1-yl}(2-trifluoromethylpyridin-5-yl)methanone;
5-((1-(methylsulfonyl)piperidin-4-yl)methoxy)quinazoline-2,4-diamine;
5-[1-(4-t-butylbenzenesulfonyl)piperidin-4-ylmethoxy]quinazoline-2,4-diamine;
5-((1-(5-chlorothiophen-2-ylsulfonyl)piperidin-4-yl)methoxy)quinazoline-2,4-diamine;
5-((1-(thiophen-2-ylsulfonyl)piperidin-4-yl)methoxy)quinazoline-2,4-diamine;
5-((1-(3,5-dimethylisoxazol-4-ylsulfonyl)piperidin-4-yl)methoxy)quinazoline-2,4-diamine;
5-[1-(3-fluorobenzenesulfonyl)piperidin-4-ylmethoxy]quinazoline-2,4-diamine;
5-[1-(2,3-dichlorobenzenesulfonyl)piperidin-4-ylmethoxy]quinazoline-2,4-diamine;
5-[1-(5-fluoro-2-methylbenzenesulfonyl)piperidin-4-ylmethoxy]quinazoline-2,4-diamine;
5-[1-(5-chloro-2-methoxybenzenesulfonyl)piperidin-4-ylmethoxy]quinazoline-2,4-diamine;
5-[1-(3-chloro-2-methylbenzenesulfonyl)piperidin-4-ylmethoxy]quinazoline-2,4-diamine;
5-[1-(4-trifluoromethylbenzenesulfonyl)piperidin-4-ylmethoxy]quinazoline-2,4-diamine;
5-[1-(5-bromo-2-methoxybenzenesulfonyl)piperidin-4-ylmethoxy]quinazoline-2,4-diamine;
5-[1-(2,4-dichlorobenzenesulfonyl)piperidin-4-ylmethoxy]quinazoline-2,4-diamine;
5-[1-(2,6-dichlorobenzenesulfonyl)piperidin-4-ylmethoxy]quinazoline-2,4-diamine;
5-[1-(4-methanesulfonylbenzenesulfonyl)piperidin-4-ylmethoxy]quinazoline-2,4-diamine;
5-[1-(2-trifluoromethylbenzenesulfonyl)piperidin-4-ylmethoxy]quinazoline-2,4-diamine;
5-[1-(3,4-dichlorobenzenesulfonyl)piperidin-4-ylmethoxy]quinazoline-2,4-diamine;
5-[1-(4-isopropylbenzenesulfonyl)piperidin-4-ylmethoxy]quinazoline-2,4-diamine;
N-(4-(4-((2,4-diaminoquinazolin-5-yloxy)methyl)piperidin-1-ylsulfonyl)phenyl)-2,2,2-trifluoroacetamide;
5-((1-((3,5-dimethylisoxazol-4-yl)methyl)piperidin-4-yl)methoxy)quinazoline-2,4-diamine;
5-((1-(2-fluoro-3-methylbenzyl)piperidin-4-yl)methoxy)quinazoline-2,4-diamine;
5-((1-((2,6-dimethylpyridin-4-yl)methyl)piperidin-4-yl)methoxy)quinazoline-2,4-diamine;
N-(4-((4-((2,4-diaminoquinazolin-5-yloxy)methyl)piperidin-1-yl)methyl)thiazol-2-yl)acetamide;
5-((1-(cyclopropylmethyl)piperidin-4-yl)methoxy)quinazoline-2,4-diamine;
5-((1-((2,3-dihydrobenzo[b][1,4]dioxin-2-yl)methyl)piperidin-4-yl)methoxy)quinazoline-2,4-diamine;
5-[1-(benzenesulfonyl)piperidin-4-ylmethoxy]quinazoline-2,4-diamine;
5-((1-benzylpiperidin-4-yl)methoxy)quinazoline-2,4-diamine;
5-((1-(benzo[d][1,3]dioxol-5-ylmethyl)piperidin-4-yl)methoxy)quinazoline-2,4-diamine;
5-((1-((6-chlorobenzo[d][1,3]dioxol-5-yl)methyl)piperidin-4-yl)methoxy)quinazoline-2,4-diamine;
5-((1-(2-(trifluoromethoxy)benzyl)piperidin-4-yl)methoxy)quinazoline-2,4-diamine;
5-((1-(4-(trifluoromethoxy)benzyl)piperidin-4-yl)methoxy)quinazoline-2,4-diamine;
5-((1-(3-(trifluoromethoxy)benzyl)piperidin-4-yl)methoxy)quinazoline-2,4-diamine;
5-((1-(2,4-dichlorobenzyl)piperidin-4-yl)methoxy)quinazoline-2,4-diamine;
benzo[d][1,3]dioxol-5-yl(4-((2,4-diaminoquinazolin-5-yloxy)methyl)piperidin-1-yl)methanone;
(4-((2,4-diaminoquinazolin-5-yloxy)methyl)piperidin-1-yl)(phenyl)methanone;
(4-((2,4-diaminoquinazolin-5-yloxy)methyl)piperidin-1-yl)(2,6-difluorophenyl)methanone;
(4-((2,4-diaminoquinazolin-5-yloxy)methyl)piperidin-1-yl)(2,6-dichlorophenyl)methanone;
(4-((2,4-diaminoquinazolin-5-yloxy)methyl)piperidin-1-yl)(3,4-dichlorophenyl)methanone;
(4((2,4-diaminoquinazolin-5-yloxy)methyl)piperidin-1-yl)(2-fluoro-3-trifluoromethylphenyl)methanone;
5-((1-(4-fluorophenylsulfonyl)piperidin-4-yl)methoxy)quinazoline-2,4-diamine;
5-((1-(4-(trifluoromethoxy)phenylsulfonyl)piperidin-4-yl)methoxy)quinazoline-2,4-diamine;

5-((1-(2-methoxybenzyl)piperidin-4-yl)methoxy)quinazoline-2,4-diamine;
5-((1-(3-methoxybenzyl)piperidin-4-yl)methoxy)quinazoline-2,4-diamine;
(4-((2,4-diaminoquinazolin-5-yloxy)methyl)piperidin-1-yl)(3-(dimethylamino)phenyl)methanone;
5-((1-(3,5-dichlorobenzyl)piperidin-4-yl)methoxy)quinazoline-2,4-diamine;
5-((1-methylpiperidin-4-yl)methoxy)quinazoline-2,4-diamine;
5-((1-(pyridin-2-ylmethyl)piperidin-4-yl)methoxy)quinazoline-2,4-diamine;
5-((1-(pyridin-4-ylmethyl)piperidin-4-yl)methoxy)quinazoline-2,4-diamine;
5-((1-(pyridin-3-ylmethyl)piperidin-4-yl)methoxy)quinazoline-2,4-diamine;
5-((1-(cyclobutylmethyl)piperidin-4-yl)methoxy)quinazoline-2,4-diamine;
5-((1-(3-fluoro-4-methoxybenzyl)piperidin-4-yl)methoxy)quinazoline-2,4-diamine;
5-((1-(4-trifluoromethylbenzyl)piperidin-4-yl)methoxy)quinazoline-2,4-diamine;
5-((1-(4-methoxybenzyl)piperidin-4-yl)methoxy)quinazoline-2,4-diamine;
5-((1-((tetrahydro-2H-pyran-2-yl)methyl)piperidin-4-yl)methoxy)quinazoline-2,4-diamine;
(4-((2,4-diaminoquinazolin-5-yloxy)methyl)piperidin-1-yl)(pyrrolidin-1-yl)methanone;
(4-((2,4-diaminoquinazolin-5-yloxy)methyl)piperidin-1-yl)(morpholino)methanone;
5-((1-((tetrahydrofuran-2-yl)methyl)piperidin-4-yl)methoxy)quinazoline-2,4-diamine;
5-((1-(4-t-butylbenzyl)piperidin-4-yl)methoxy)quinazoline-2,4-diamine;
5-((1-(3-trifluoromethylbenzyl)piperidin-4-yl)methoxy)quinazoline-2,4-diamine;
5-((1-(2-trifluoromethylbenzyl)piperidin-4-yl)methoxy)quinazoline-2,4-diamine;
5-((1-(3-fluoromethylbenzyl)piperidin-4-yl)methoxy)quinazoline-2,4-diamine;
5-((1-(3,5-dimethoxybenzyl)piperidin-4-yl)methoxy)quinazoline-2,4-diamine;
5-((1-(3-dimethylaminobenzyl)piperidin-4-yl)methoxy)quinazoline-2,4-diamine;
5-((1-(thiophen-2-ylmethyl)piperidin-4-yl)methoxy)quinazoline-2,4-diamine;
5-((1-((1,4-dimethyl-1H-pyrrol-2-yl)methyl)piperidin-4-yl)methoxy)quinazoline-2,4-diamine;
5-((1-(3,5-difluorobenzyl)piperidin-4-yl)methoxy)quinazoline-2,4-diamine;
5-((1-isobutylpiperidin-4-yl)methoxy)quinazoline-2,4-diamine;
5-((1-isopentylpiperidin-4-yl)methoxy)quinazoline-2,4-diamine;
5-((1-(2,3-dichlorobenzyl)piperidin-4-yl)methoxy)quinazoline-2,4-diamine;
5-((1-(cyclohexylmethyl)piperidin-4-yl)methoxy)quinazoline-2,4-diamine;
5-((1-(2,6-dichlorobenzyl)piperidin-4-yl)methoxy)quinazoline-2,4-diamine;
5-((1-(2,5-difluorobenzyl)piperidin-4-yl)methoxy)quinazoline-2,4-diamine;
5-((1-hexylpiperidin-4-yl)methoxy)quinazoline-2,4-diamine;
5-((1-(thiophen-3-ylmethyl)piperidin-4-yl)methoxy)quinazoline-2,4-diamine;
5-((1-(2,5-dimethylbenzyl)piperidin-4-yl)methoxy)quinazoline-2,4-diamine;
5-((1-(2,6-difluorobenzyl)piperidin-4-yl)methoxy)quinazoline-2,4-diamine;
5-((1-(3,4,5-trifluorobenzyl)piperidin-4-yl)methoxy)quinazoline-2,4-diamine;
5-((1-(4-fluorobenzyl)piperidin-4-yl)methoxy)quinazoline-2,4-diamine;
5-((1-(2,4,5-trifluorobenzyl)piperidin-4-yl)methoxy)quinazoline-2,4-diamine;
5-((1-(piperidin-4-ylmethyl)piperidin-4-yl)methoxy)quinazoline-2,4-diamine;
5-((1-((1-methyl-1H-imidazol-2-yl)methyl)piperidin-4-yl)methoxy)quinazoline-2,4-diamine;
5-[4-(3-chlorobenzyl)cyclohexylmethoxy]quinazoline-2,4-diamine;
5-[4-(2-fluorobenzyl)cyclohexylmethoxy]quinazoline-2,4-diamine;
5-[1-(2-fluorophenyl)piperidin-4-ylmethoxy]quinazoline-2,4-diamine;
methyl 3-((4-((2,4-diaminoquinazolin-5-yloxy)methyl)piperidin-1-yl)methyl)benzoate;
methyl 4-((4-((2,4-diaminoquinazolin-5-yloxy)methyl)piperidin-1-yl)methyl)benzoate;
5-((1-(2,6-dimethylbenzyl)piperidin-4-yl)methoxy)quinazoline-2,4-diamine;
5-((1-(2,2-difluoroethyl)piperidin-4-yl)methoxy)quinazoline-2,4-diamine;
5-[1-(2-fluoro-6-trifluoromethylbenzyl)piperidin-4-ylmethoxy]quinazoline-2,4-diamine;
5-[1-(2-chloro-6-fluorobenzyl)piperidin-4-ylmethoxy]quinazoline-2,4-diamine;
5-[4-(2,6-difluorophenoxy)cyclohexylmethoxy]-quinazoline-2,4-diamine;
5-[1-(2-chlorophenyl)piperidin-4-ylmethoxy]quinazoline-2,4-diamine;
5-[4-(2-chlorobenzyl)cyclohexylmethoxy]quinazoline-2,4-diamine;
5-((1-(2,2,2-trifluoroethyl)piperidin-4-yl)methoxy)quinazoline-2,4-diamine;
5-[1-(4-trifluoromethylphenyl)piperidin-4-ylmethoxy]quinazoline-2,4-diamine;
5-[4-(4-chlorophenyl)cyclohexylmethoxy]quinazoline-2,4-diamine;
5-[4-(2-Methoxybenzyl)-cyclohexylmethoxy]quinazoline-2,4-diamine;
4-[2-(2,4-diamino-quinazolin-5-yloxy)-ethyl]-piperazine-1-carboxylic acid tert-butyl ester;
5-{2-[4-(2-fluoro-benzenesulfonyl)-piperazin-1-yl]-ethoxy}-quinazoline-2,4-diamine;
{4-[2-(2,4-diamino-quinazolin-5-yloxy)-ethyl]-piperazin-1-yl}-(2,4-difluoro-phenyl)-methanone;
benzo[1,3]dioxol-5-yl-{4-[2-(2,4-diamino-quinazolin-5-yloxy)-ethyl]-piperazin-1-yl}-methanone;
5-[2-(4-benzenesulfonyl-piperazin-1-yl)-ethoxy]-quinazoline-2,4-diamine;
5-{2-[4-(2,4-difluoro-benzenesulfonyl)-piperazin-1-yl]-ethoxy}-quinazoline-2,4-diamine;
5-{2-[4-(3,4-dichloro-benzenesulfonyl)-piperazin-1-yl]-ethoxy}-quinazoline-2,4-diamine;
{4-[2-(2,4-diamino-quinazolin-5-yloxy)-ethyl]-piperazin-1-yl}-(3,4-dichloro-phenyl)-methanone;
{4-[2-(2,4-diamino-quinazolin-5-yloxy)-ethyl]-piperazin-1-yl}-phenyl-methanone;
(4-chloro-phenyl)-{4-[2-(2,4-diamino-quinazolin-5-yloxy)-ethyl]-piperazin-1-yl}-methanone;
{4-[2-(2,4-diamino-quinazolin-5-yloxy)-ethyl]-piperazin-1-yl}-(2-fluoro-phenyl)-methanone;
5-{2-[4-(2-fluoro-benzyl)-piperazin-1-yl]-ethoxy}-quinazoline-2,4-diamine;
5-{2-[4-(2,4-difluoro-benzyl)-piperazin-1-yl]ethoxy}-quinazoline-2,4-diamine;
5-{2-[4-(3-chloro-benzyl)-piperazin-1-yl]-ethoxy}-quinazoline-2,4-diamine; and
4-((2,4-diaminoquinazolin-5-yloxy)methyl)-1-(2-fluorobenzyl)piperidine 1-oxide;
and pharmaceutically acceptable salts thereof.

53. A compound selected from the group consisting of:

3-((4-((2,4-diaminoquinazolin-5-yloxy)methyl)piperidin-1-yl)methyl)benzoic acid;

4-((4-((2,4-diaminoquinazolin-5-yloxy)methyl)piperidin-1-yl)methyl)benzoic acid;

5-{1-[1-(2,6-dichloro-benzyl)-piperidin-4-yl]-1-methyl-ethoxy}-quinazoline-2,4-diamine;

5-{1-[1-(2-chloro-6-fluoro-benzyl)-piperidin-4-yl]-1-methyl-ethoxy}-quinazoline-2,4-diamine;

5-[1-(2-fluoro-benzyl)-2,6-dimethyl-piperidin-4-yl-methoxy]-quinazoline-2,4-diamine; and 5-[1-(2-chloro-6-fluoro-benzyl)-2,6-dimethyl-piperidin-4-ylmethoxy]-quinazoline-2,4-diamine;

and pharmaceutically acceptable salts thereof.

* * * * *

UNITED STATES PATENT AND TRADEMARK OFFICE
CERTIFICATE OF CORRECTION

| | | |
|---|---|---|
| PATENT NO. | : 7,985,755 B2 | Page 1 of 1 |
| APPLICATION NO. | : 11/832255 | |
| DATED | : July 26, 2011 | |
| INVENTOR(S) | : Jasbir Singh | |

It is certified that error appears in the above-identified patent and that said Letters Patent is hereby corrected as shown below:

Column 144, Line 62, Claim 1, delete "loweralkoxy" and insert -- lower alkoxy --

Column 144, Line 67, Claim 1, delete "loweralkylhydroxy" and insert -- lower alkylhydroxy --

Column 145, Line 20, Claim 10, delete "Q is $CH_2$" and insert -- Q is $-CH_2-$ --

Column 145, Line 30, Claim 13, delete "$CH_2$" and insert -- $-CH_2-$ --

Column 145, Line 60 (approx.), Claim 16, delete "—$CH_2C(=O)$;" and insert -- —$CH_2C(=O)$—; --

Column 146, Lines 9-10 (approx.), Claim 20, delete "Q is $CH_2$" and insert -- Q is $-CH_2-$ --

Column 148, Line 4, Claim 35, delete "Q is $CH_2$" and insert -- Q is $-CH_2-$ --

Column 148, Lines 32-33, Claim 37, delete
"[4-(2,4-Diaminoquinazolin-5-yloxymethyl)piperidin-1-yl]-(2-iodophenyl)methanone" and insert
-- [4-(2,4-Diaminoquinazolin-5-yloxymethyl)piperidin-1-yl]-(2-iodophenyl)methanone; --

Column 149, Lines 30-32 (approx.), Claim 46, delete
"Benzo[1,3]dioxol-5-yl-{4-[2-(2,4-diamino-quinazolin-5-yloxy)-ethyl]-piperazin-1-yl}-methanone"
and insert
-- Benzo[1,3]dioxol-5-yl-{4-[2-(2,4-diamino-quinazolin-5-yloxy)-ethyl]-piperazin-1-yl}-methanone --

Column 151, Line 33-34, Claim 52, delete
"{-4-[(2,4-diaminoquinazolin-5-yloxy)methyl]piperidin-1yl}(naphthalen1-yl)methanone" and insert
-- {4-[(2,4-diaminoquinazolin-5-yloxy)methyl]piperidin-1-yl}(naphthalen-1-yl)methanone --

Signed and Sealed this
Second Day of October, 2012

David J. Kappos
*Director of the United States Patent and Trademark Office*